United States Patent
Stasko et al.

(10) Patent No.: US 10,912,743 B2
(45) Date of Patent: *Feb. 9, 2021

(54) COMPOSITIONS FOR TREATING INFLAMMATION AND METHODS OF TREATING THE SAME

(71) Applicant: Novan, Inc., Morrisville, NC (US)

(72) Inventors: Nathan Stasko, Chapel Hill, NC (US); Ryan Doxey, Raleigh, NC (US); Kimberly McHale, Hillsborough, NC (US); Stanley J. Hollenbach, Raleigh, NC (US)

(73) Assignee: Novan, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/081,708

(22) PCT Filed: Mar. 2, 2017

(86) PCT No.: PCT/US2017/020426
§ 371 (c)(1),
(2) Date: Aug. 31, 2018

(87) PCT Pub. No.: WO2017/151905
PCT Pub. Date: Sep. 8, 2017

(65) Prior Publication Data
US 2019/0015358 A1    Jan. 17, 2019

Related U.S. Application Data

(60) Provisional application No. 62/442,184, filed on Jan. 4, 2017, provisional application No. 62/422,294, filed (Continued)

(51) Int. Cl.
*A61K 9/06* (2006.01)
*A61K 47/06* (2006.01)
(Continued)

(52) U.S. Cl.
CPC .......... *A61K 31/132* (2013.01); *A61K 9/0014* (2013.01); *A61K 9/06* (2013.01);
(Continued)

(58) Field of Classification Search
CPC ...... A61K 31/132; A61K 33/00; A61K 47/06; A61K 9/0014; A61K 9/06; A61P 17/00;
(Continued)

(56) References Cited

U.S. PATENT DOCUMENTS

| 3,754,368 A | 8/1973 | Moore et al. |
| 4,182,827 A | 1/1980 | Jones et al. |

(Continued)

FOREIGN PATENT DOCUMENTS

| CA | 2 594 407 A1 | 8/2006 |
| CN | 101180037 A | 5/2008 |

(Continued)

OTHER PUBLICATIONS

Ignarro et al. (Proc. Natl. Acad. Sci USA 1993;90:8103-8107). (Year: 1993).*

(Continued)

*Primary Examiner* — Ernst V Arnold
(74) *Attorney, Agent, or Firm* — Myers Bigel, P.A.

(57) ABSTRACT

Provided herein are compositions useful for treating inflammation in a subject and methods of decreasing inflammation in the skin, mucosa, and/or eye of a subject comprising applying a pharmaceutical composition that includes an NO-releasing compound to the skin, mucosa, and/or eye of the subject in an amount sufficient to decrease inflammation.

18 Claims, 8 Drawing Sheets

Related U.S. Application Data on Nov. 15, 2016, provisional application No. 62/303,777, filed on Mar. 4, 2016, provisional application No. 62/302,495, filed on Mar. 2, 2016.

(51) Int. Cl.
| | | |
|---|---|---|
| *A61P 17/00* | (2006.01) | |
| *A61K 31/132* | (2006.01) | |
| *A61K 47/14* | (2017.01) | |
| *A61P 17/06* | (2006.01) | |
| *A61P 17/02* | (2006.01) | |
| *A61P 27/16* | (2006.01) | |
| *A61P 29/00* | (2006.01) | |
| *A61K 9/00* | (2006.01) | |
| *A61K 33/00* | (2006.01) | |

(52) U.S. Cl.
CPC .............. *A61K 33/00* (2013.01); *A61K 47/06* (2013.01); *A61K 47/14* (2013.01); *A61P 17/00* (2018.01); *A61P 17/02* (2018.01); *A61P 17/06* (2018.01); *A61P 27/16* (2018.01); *A61P 29/00* (2018.01)

(58) Field of Classification Search
CPC ......... A61P 17/02; A61P 17/06; A61P 27/16; A61P 29/00
See application file for complete search history.

(56) References Cited

U.S. PATENT DOCUMENTS

| | | | |
|---|---|---|---|
| 4,678,666 A | 7/1987 | Nozawa et al. | |
| 4,829,092 A | 5/1989 | Nelson et al. | |
| 4,917,886 A | 4/1990 | Asche et al. | |
| 5,405,919 A | 4/1995 | Keefer | |
| 5,519,020 A | 5/1996 | Smith et al. | |
| 5,691,423 A | 11/1997 | Smith et al. | |
| 5,770,645 A | 6/1998 | Stamler et al. | |
| 5,814,656 A | 9/1998 | Saavedra et al. | |
| 5,814,666 A | 9/1998 | Green et al. | |
| 5,840,759 A | 11/1998 | Mitchell et al. | |
| 5,910,316 A | 6/1999 | Keefer et al. | |
| 5,958,427 A | 9/1999 | Salzman et al. | |
| 5,968,001 A | 10/1999 | Freeman | |
| 5,968,528 A | 10/1999 | Deckner et al. | |
| 6,103,266 A | 8/2000 | Tapolsky et al. | |
| 6,103,275 A | 8/2000 | Seitz et al. | |
| 6,110,453 A | 8/2000 | Keefer et al. | |
| 6,303,141 B1 | 10/2001 | Fischer et al. | |
| 6,319,913 B1 | 11/2001 | Mak et al. | |
| 6,382,526 B1 | 5/2002 | Reneker et al. | |
| 6,465,445 B1 | 10/2002 | Labrie | |
| 6,479,058 B1 | 11/2002 | McCadden | |
| 6,520,425 B1 | 2/2003 | Reneker | |
| 6,695,992 B2 | 2/2004 | Reneker | |
| 6,719,997 B2 | 4/2004 | Hsu et al. | |
| 6,737,447 B1 | 5/2004 | Smith et al. | |
| 6,818,018 B1 | 11/2004 | Sawhney | |
| 6,861,064 B1 | 3/2005 | Laakso et al. | |
| 7,048,951 B1 | 5/2006 | Seitz et al. | |
| 7,704,518 B2 | 4/2010 | Tamarkin et al. | |
| 8,241,650 B2 | 8/2012 | Peters | |
| 8,282,967 B2 | 10/2012 | Schoenfisch et al. | |
| 8,343,945 B2 | 1/2013 | Tamarkin et al. | |
| 8,362,091 B2 | 1/2013 | Tamarkin et al. | |
| 8,399,005 B2 | 3/2013 | Schoenfisch et al. | |
| 8,486,374 B2 | 7/2013 | Tamarkin et al. | |
| 8,486,451 B2 | 7/2013 | Morris et al. | |
| 8,591,876 B2 | 11/2013 | Bauman et al. | |
| 8,617,100 B2 | 12/2013 | Eini et al. | |
| 8,636,982 B2 | 1/2014 | Tamarkin et al. | |
| 8,722,103 B2 | 5/2014 | Morris et al. | |
| 8,795,635 B2 | 8/2014 | Tamarkin et al. | |
| 8,795,693 B2 | 8/2014 | Tamarkin et al. | |
| 8,900,553 B2 | 12/2014 | Tamarkin et al. | |
| 8,937,143 B2 | 1/2015 | Bao et al. | |
| 8,956,658 B2 | 2/2015 | Schoenfisch et al. | |
| 8,962,029 B2 | 2/2015 | Schoenfisch et al. | |
| 9,101,662 B2 | 8/2015 | Tamarkin et al. | |
| 9,161,916 B2 | 10/2015 | Tamarkin et al. | |
| 9,238,038 B2 | 1/2016 | Schoenfisch et al. | |
| 9,265,725 B2 | 2/2016 | Tamarkin et al. | |
| 9,267,006 B2 | 2/2016 | Bao et al. | |
| 9,320,705 B2 | 4/2016 | Tamarkin et al. | |
| 9,403,851 B2 | 8/2016 | Schoenfisch et al. | |
| 9,403,852 B2 | 8/2016 | Schoenfisch et al. | |
| 10,226,483 B2 * | 3/2019 | Doxey | A61K 9/107 |
| 2002/0012816 A1 | 1/2002 | Shimizu et al. | |
| 2002/0013304 A1 | 1/2002 | Wilson et al. | |
| 2002/0028223 A1 | 3/2002 | Vatter et al. | |
| 2002/0082221 A1 | 6/2002 | Herrmann et al. | |
| 2002/0094985 A1 | 7/2002 | Herrmann et al. | |
| 2002/0122771 A1 | 9/2002 | Holland et al. | |
| 2002/0136750 A1 | 9/2002 | Benjamin et al. | |
| 2002/0155174 A1 | 10/2002 | Benjamin et al. | |
| 2003/0077243 A1 | 4/2003 | Fitzhugh | |
| 2003/0159702 A1 | 8/2003 | Lindell et al. | |
| 2003/0175328 A1 | 9/2003 | Shefer et al. | |
| 2003/0205234 A1 | 11/2003 | Bardach et al. | |
| 2003/0235605 A1 | 12/2003 | Lelah et al. | |
| 2004/0009238 A1 | 1/2004 | Miller et al. | |
| 2004/0043068 A1 | 3/2004 | Tedeschi et al. | |
| 2004/0068005 A1 | 4/2004 | Szilvassy et al. | |
| 2004/0171589 A1 | 9/2004 | Herrmann et al. | |
| 2004/0202684 A1 | 10/2004 | Djerassi | |
| 2004/0220260 A1 | 11/2004 | Cals-Grierson | |
| 2004/0265244 A1 | 12/2004 | Rosen | |
| 2005/0038473 A1 | 2/2005 | Tamarkin et al. | |
| 2005/0113409 A1 * | 5/2005 | Connor | A61K 31/415 |
| | | | 514/311 |
| 2005/0232869 A1 | 10/2005 | Tamarkin et al. | |
| 2005/0271596 A1 | 12/2005 | Friedman et al. | |
| 2006/0159734 A1 | 7/2006 | Shudo | |
| 2006/0160897 A1 | 7/2006 | Pelicci et al. | |
| 2006/0173076 A1 | 8/2006 | Vishnupad et al. | |
| 2006/0269620 A1 | 11/2006 | Morris et al. | |
| 2006/0275218 A1 | 12/2006 | Tamarkin et al. | |
| 2007/0166255 A1 | 7/2007 | Gupta | |
| 2007/0243224 A1 | 10/2007 | Ludwig et al. | |
| 2007/0292359 A1 | 12/2007 | Friedman et al. | |
| 2007/0292461 A1 | 12/2007 | Tamarkin et al. | |
| 2008/0031907 A1 | 2/2008 | Tamarkin et al. | |
| 2008/0044444 A1 | 2/2008 | Tamarkin et al. | |
| 2008/0063607 A1 | 3/2008 | Tamarkin et al. | |
| 2008/0069779 A1 | 3/2008 | Tamarkin et al. | |
| 2008/0071206 A1 | 3/2008 | Peters | |
| 2008/0138296 A1 | 6/2008 | Tamarkin et al. | |
| 2008/0152596 A1 | 6/2008 | Friedman et al. | |
| 2008/0166303 A1 | 7/2008 | Tamarkin et al. | |
| 2008/0188446 A1 | 8/2008 | Muldoon et al. | |
| 2008/0206155 A1 | 8/2008 | Tamarkin et al. | |
| 2008/0206159 A1 | 8/2008 | Tamarkin et al. | |
| 2008/0206161 A1 | 8/2008 | Tamarkin et al. | |
| 2008/0253973 A1 | 10/2008 | Tamarkin et al. | |
| 2008/0260655 A1 | 10/2008 | Tamarkin et al. | |
| 2008/0292560 A1 | 11/2008 | Tamarkin et al. | |
| 2008/0299220 A1 | 12/2008 | Tamarkin et al. | |
| 2008/0311163 A1 | 12/2008 | Peters | |
| 2008/0317679 A1 | 12/2008 | Tamarkin et al. | |
| 2009/0041680 A1 | 2/2009 | Tamarkin et al. | |
| 2009/0068118 A1 | 3/2009 | Eini et al. | |
| 2009/0068248 A1 | 3/2009 | Waterhouse et al. | |
| 2009/0130029 A1 | 5/2009 | Tamarkin et al. | |
| 2009/0175799 A1 | 7/2009 | Tamarkin et al. | |
| 2009/0214618 A1 | 8/2009 | Schoenfisch et al. | |
| 2009/0226380 A1 | 9/2009 | Clark et al. | |
| 2009/0297634 A1 | 12/2009 | Friedman et al. | |
| 2010/0015253 A1 | 1/2010 | Benjamin | |
| 2010/0098733 A1 | 4/2010 | Stasko | |
| 2010/0221195 A1 | 9/2010 | Tamarkin et al. | |
| 2010/0239512 A1 | 9/2010 | Morris et al. | |
| 2010/0266510 A1 | 10/2010 | Tamarkin et al. | |
| 2010/0286285 A1 | 11/2010 | Barthez et al. | |

(56) References Cited

U.S. PATENT DOCUMENTS

| | | |
|---|---|---|
| 2010/0310476 A1 | 12/2010 | Tamarkin et al. |
| 2010/0331968 A1 | 12/2010 | Morris et al. |
| 2011/0027369 A1 | 2/2011 | Franke |
| 2011/0045037 A1 | 2/2011 | Tamarkin et al. |
| 2011/0052650 A1 | 3/2011 | Morris et al. |
| 2011/0082167 A1 | 4/2011 | Pisak et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2011/0263526 A1 | 10/2011 | Satyam |
| 2012/0021055 A1 | 1/2012 | Schoenfisch et al. |
| 2012/0114547 A1 | 5/2012 | Smith |
| 2012/0134951 A1* | 5/2012 | Stasko ............ A61K 9/0014 424/78.06 |
| 2012/0136323 A1 | 5/2012 | Stasko et al. |
| 2012/0141384 A1 | 6/2012 | Tamarkin et al. |
| 2012/0156163 A1 | 6/2012 | Bauman et al. |
| 2012/0202841 A1 | 8/2012 | Kriwet et al. |
| 2012/0237453 A1 | 9/2012 | Tamarkin et al. |
| 2013/0059017 A1 | 3/2013 | Perricone et al. |
| 2013/0109756 A1 | 5/2013 | Huber et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2013/0344334 A1 | 12/2013 | Schoenfisch et al. |
| 2014/0017121 A1 | 1/2014 | Schoenfisch et al. |
| 2014/0057001 A1 | 2/2014 | Bauman et al. |
| 2014/0058124 A1 | 2/2014 | Schoenfisch et al. |
| 2014/0065200 A1 | 3/2014 | Schoenfisch et al. |
| 2014/0107071 A1 | 4/2014 | Kougoulos et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0242023 A1 | 8/2014 | Doxey et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0024052 A1 | 1/2015 | Doxey |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0141606 A1 | 5/2015 | Bao et al. |
| 2015/0182543 A1 | 7/2015 | Schoenfisch et al. |
| 2015/0225488 A1 | 8/2015 | Schoenfisch et al. |
| 2016/0008275 A1 | 1/2016 | Doxey et al. |

FOREIGN PATENT DOCUMENTS

| | | |
|---|---|---|
| CN | 102100663 A | 6/2011 |
| EP | 1 300 424 A1 | 4/2003 |
| EP | 1 707 224 A1 | 10/2006 |
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| GB | 2 354 441 | 3/2001 |
| JP | 03-044396 | 2/1991 |
| JP | H07-039748 | 2/1995 |
| JP | 2003-212773 | 7/2003 |
| JP | 2003-286153 | 10/2003 |
| JP | 2012-197300 | 10/2012 |
| WO | WO 93/10754 A1 | 6/1993 |
| WO | WO 94/08603 A1 | 4/1994 |
| WO | WO 96/13164 A1 | 5/1996 |
| WO | WO 96/15797 A1 | 5/1996 |
| WO | WO 98/05689 A1 | 2/1998 |
| WO | WO 00/49993 A2 | 8/2000 |
| WO | WO 01/21148 A1 | 3/2001 |
| WO | WO 01/26702 A2 | 4/2001 |
| WO | WO 01/85013 A2 | 11/2001 |
| WO | WO 02/020026 A2 | 3/2002 |
| WO | WO 02/041902 A1 | 5/2002 |
| WO | WO 02/056864 A2 | 7/2002 |
| WO | WO 03/013489 A1 | 2/2003 |
| WO | WO 03/072039 A2 | 9/2003 |
| WO | WO 03/078437 A1 | 9/2003 |
| WO | WO 03/086282 A2 | 10/2003 |
| WO | WO 03/092763 A1 | 11/2003 |
| WO | WO 2004/012659 A2 | 2/2004 |
| WO | WO 2004/012874 A1 | 2/2004 |
| WO | WO 2004/098538 A2 | 11/2004 |
| WO | WO 2005/003032 A1 | 1/2005 |
| WO | WO 2005/004984 A1 | 1/2005 |
| WO | WO 2005/011575 A2 | 2/2005 |
| WO | WO 2005/037339 A1 | 4/2005 |
| WO | WO 2005/046661 A2 | 5/2005 |
| WO | WO 2006/084910 A2 | 8/2006 |
| WO | WO 2006/084912 A1 | 8/2006 |
| WO | WO 2006/100154 A1 | 9/2006 |
| WO | WO 2006/100692 A2 | 9/2006 |
| WO | WO 2006/128121 A2 | 11/2006 |
| WO | WO 2006/138035 A1 | 12/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/094866 A1 | 8/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/067095 A1 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2010/016686 A2 | 2/2010 |
| WO | WO 2011/005846 A1 | 1/2011 |
| WO | WO 2011/022652 A1 | 2/2011 |
| WO | WO 2011/022680 A2 | 2/2011 |
| WO | WO 2011/061519 A2 | 5/2011 |
| WO | WO 2011/073998 A1 | 6/2011 |
| WO | 2011085484 | 7/2011 |
| WO | WO 2012/001403 A1 | 1/2012 |
| WO | WO 2012/035468 A2 | 3/2012 |
| WO | WO 2012/082976 A1 | 6/2012 |
| WO | WO 2012/100174 A1 | 7/2012 |
| WO | WO 2012/153331 A2 | 11/2012 |
| WO | WO 2013/006608 A1 | 1/2013 |
| WO | WO 2013/006613 A1 | 1/2013 |
| WO | WO 2013/029009 A1 | 2/2013 |
| WO | WO 2013/063354 A1 | 5/2013 |
| WO | WO 2013/138073 A1 | 9/2013 |
| WO | WO 2013/138075 A1 | 9/2013 |
| WO | 2014134502 | 9/2014 |
| WO | WO 2015/021382 A2 | 2/2015 |
| WO | WO 2016/007834 A1 | 1/2016 |
| WO | WO 2016/010988 A1 | 1/2016 |
| WO | WO 2016/022170 A1 | 2/2016 |

OTHER PUBLICATIONS

Schmid-Wendtner et al. (Skin Pharmacol Physiol. 2006;19:296-302) (Year: 2006).*

International Search Report and the Written Opinion of the International Searching Authority corresponding to International Patent Application No. PCT/US2017/020426 (15 pages) (dated May 8, 2017).

(56) References Cited

OTHER PUBLICATIONS

U.S. Appl. No. 14/133,973, Kougoulos et al., Dec. 19, 2013.
U.S. Appl. No. 14/191,958, Doxey, Feb. 27, 2014.
U.S. Appl. No. 14/771,138, Doxey, Aug. 27, 2015.
U.S. Appl. No. 15/156,889, Peters, May 17, 2016.
Al-Sa'Doni et al. "S-Nitrosothiols: a class of nitric oxide-donor drugs" *Clinical Science* 98:507-520 (2000).
Amadeu et al. "Nitric Oxide Donor Improves Healing if Applied on Inflammatory and Proliferative Phase" *Journal of Surgical* Research 149(1):84-93 (2008).
Bohl Masters et al. "Effects of nitric oxide releasing poly(vinyl alcohol) hydrogel dressings on dermal wound healing in diabetic mice" *Wound Repair and Regeneration* 10(5):286-294 (2002).
Boykin et al. "HBO Mediates Increased Nitric Oxide Production Associated With Wound Healing" *Wound Repaid and Regeneration* 12(2):A15 (Abstract 054) (2004).
Butsch et al. "Topical treatment with a two-component gel releasing nitric oxide cures C57BL/6 mice from cutaneous leishmaniasis caused by *Leishmania major*" Experimental Dermatology 25(11):914-916 (2016).
Hetrick et al. "Anti-biofilm efficacy of nitric oxide-releasing silica nanoparticles" *Biomaterials* 30(14):2782-2789 (2009).
Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).
International Preliminary Report on Patentability corresponding to International Patent Application No. PCT/US2017/020426 (12 pages) (dated Sep. 13, 2018).
Kandavilli et al. "Polymers in Transdermal Drug Delivery Systems" *Pharmaceutical Technology* pp. 62-80 (2002).
"Novan Announces Preclinical Data Demonstrating Immunomodulatory Effect *In Vivo* Topical Application of SB414 Inhibited IL-17 in Psoriasis Mouse Model Effect Relates to Multiple Inflammatory Skin Diseases" Press Release (3 pages) (Nov. 16, 2016).
Pulfer et al. "Incorporation of nitric oxide-releasing crosslinked polyethyleneimine microspheres into vascular grafts" *Journal of Biomedical Materials Research* 37:182-189 (1997).
Sangster, James "Octanol-Water Partition Coefficients of Simple Organic Compounds" *Journal of Physical and Chemical Reference Data* 18(3):1111-1227 (1989).
Smith et al. "Transdermal delivery of nitric oxide from diazeniumdiolates" *Journal of Controlled Release* 51:153-159 (1998).
Wang et al. "Nitric Oxide Donors: Chemical Activities and Biological Applications" *Chemical Reviews* 102(4):1091-1134 (2002).
Extended European Search Report corresponding to European Patent Application No. 17760806.4 (7 pages) (dated Sep. 13, 2019).
Keefer, Larry K. "Fifty Years of Diazeniumdiolate Research. From Laboratory Curiosity to Broad-Spectrum Biomedical Advances" ACS Chemical Biology, 6:1147-1155 (2011).

\* cited by examiner

ALL VALUES REPRESENT THE MEAN ± SEM FOR SIX ANIMALS. * P <0.05 VS. VEHICLE CONTROL AFTER 12 DAYS OF ONCE DAILY ADMINISTRATION.

COMPOSITIONS FOR TREATING INFLAMMATION AND METHODS OF TREATING THE SAME

RELATED APPLICATION INFORMATION

This application claims the benefit of U.S. Provisional Patent Application Ser. Nos. 62/302,495, filed Mar. 2, 2016, 62/303,777, filed Mar. 4, 2016, 62/422,294, filed Nov. 15, 2016, and 62/442,184, filed Jan. 4, 2017, the disclosure of each of which is incorporated herein by reference in its entirety.

FIELD

The present invention relates to compositions and methods of treating inflammation, such as, inflammatory skin conditions.

BACKGROUND

Numerous skin diseases or disorders result from inflammation with the associated release of mediators from a variety of inflammatory and resident cells. Neutrophils, mast cells and lymphocytes orchestrate an inflammatory response that results in significant release of inflammatory mediators, and the creation of numerous free radicals. Skin diseases in which inflammation is a significant component include, but are not limited to, acne, rosacea, atopic dermatitis, contact dermatitis, drug eruptions, psoriasis, seborrheic dermatitis, connective tissue diseases (such as lupus and scleroderma), other autoimmune disorders such as the blistering diseases (e.g., bullous pemphigoid and pemphigus), pigmentary diseases (e.g., post inflammatory hyperpigmentation, melasma and vitiligo), urticaria or hives, inflammation associated with skin infections such as tinea corporis or fungal infection of the finger or toenails, among others. Inflammation is an important step to most of these diseases. New compositions for treating inflammatory skin conditions and methods of making and/or using such compositions may be desirable.

For example, in treating psoriasis an escalation approach to treatment is carried out. Topical corticosteroids are typically first line therapies with escalation of strength until the disease state is addressed or, if no strength of corticosteroids is effective at treating the disease, biologics may be used. This escalating therapy strategy is carried out because of the long term side effects of corticosteroids and the potential for severe side effects of biologics, including some forms of cancer. A therapy that treated the inflammation of psoriasis without the side effects of corticosteroids or current biologics may be of benefit in treating the disease.

SUMMARY OF EMBODIMENTS

One aspect of the present invention comprises a method of treating an inflammatory condition of the skin, mucosa, and/or eye in a subject, the method comprising topically administering to the skin, mucosa, and/or eye of said subject a nitric oxide-releasing pharmaceutical composition comprising at least one nitric oxide releasing-compound comprising a diazeniumdiolate functional group in an amount effective to treat said inflammatory condition of the skin, mucosa, and/or eye.

Another aspect of the present invention includes a composition for treating inflammation, the composition comprising a nitric oxide-releasing active pharmaceutical ingredient.

A further aspect of the present invention includes a nitric oxide-releasing pharmaceutical composition comprising a first composition in admixture with a second composition, wherein the first composition comprises: at least one nitric oxide releasing compound comprising a diazeniumdiolate functional group; a hydrophobic base in an amount of about 50% to about 95% by weight of the first composition; an amphiphilic compound in an amount of about 1% to about 20% by weight of the first composition; and an emulsifying agent in an amount of about 1% to about 20% by weight of the first composition; and wherein the second composition comprises: water in an amount of about 50% to about 95% by weight of the second composition; a buffering agent in an amount of about 1% to about 20% by weight of the second composition; a polymer in an amount of about 0.5% to about 5% by weight of the second composition; and a polyhydric alcohol in an amount of about 1% to about 20% by weight of the second composition.

Another aspect of the present invention includes a nitric oxide-releasing pharmaceutical composition comprising a first composition in admixture with a second composition, wherein the first composition comprises: at least one nitric oxide releasing compound comprising a diazeniumdiolate functional group; a hydrophobic base in an amount of about 50% to about 95% by weight of the first composition; an amphiphilic compound in an amount of about 1% to about 20% by weight of the first composition; and a silicon containing compound in an amount of about 1% to about 20% by weight of the first composition; and wherein the second composition comprises: water in an amount of about 50% to about 95% by weight of the second composition; a buffering agent in an amount of about 1% to about 20% by weight of the second composition; a polymer in an amount of about 0.5% to about 5% by weight of the second composition; and a polyhydric alcohol in an amount of about 1% to about 20% by weight of the second composition.

A further aspect of the present invention includes a composition comprising at least one nitric oxide releasing compound comprising a diazeniumdiolate functional group; a hydrophobic base in an amount of about 50% to about 95% by weight of the composition; an amphiphilic compound in an amount of about 1% to about 20% by weight of the composition; and an emulsifying agent in an amount of about 1% to about 20% by weight of the composition.

Another aspect of the present invention includes a composition comprising: at least one nitric oxide releasing compound comprising a diazeniumdiolate functional group; a hydrophobic base in an amount of about 50% to about 95% by weight of the composition; an amphiphilic compound in an amount of about 1% to about 20% by weight of the composition; and a silicon containing compound in an amount of about 1% to about 20% by weight of the composition.

An additional aspect of the present invention includes a composition comprising: water in an amount of about 50% to about 95% by weight of the composition; a buffering agent in an amount of about 1% to about 20% by weight of the composition; a polymer in an amount of about 0.5% to about 5% by weight of the composition; and a polyhydric alcohol in an amount of about 1% to about 20% by weight of the composition.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

The following drawings are provided to illustrate various aspects of the present inventive concepts and are not intended to limit the scope of the present invention unless specified herein.

DETAILED DESCRIPTION OF EMBODIMENTS

Figure 1:
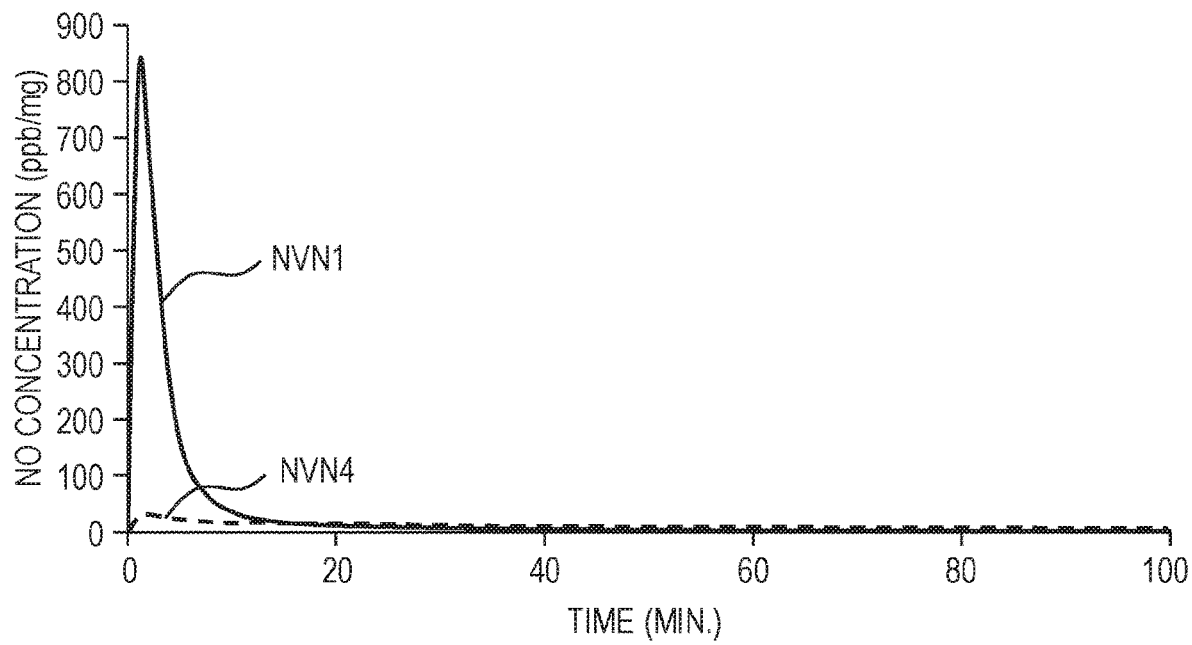
FIG. 1 shows a graph of the release profiles of two types of Nitricil™, NVN1 and NVN4, ointments according to some embodiments of the present invention under physiological conditions.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, 0.5%, or even ±0.1% of X. A range provided herein for a measurable value may include any other range and/or individual value therein.

Provided according to some embodiments of the present invention are compositions that may be useful in treating inflammation in a subject. Further provided are methods of treating inflammation in a subject. In some embodiments, a composition and/or method of the present invention may treat an inflammatory condition of the skin, mucosa, and/or eye in a subject. In some embodiments, a composition and/or method of the present invention may decrease inflammation in the skin, mucosa, and/or eye of a subject. A composition of the present invention may comprise, consist essentially of, or consist of a nitric oxide (NO)-releasing active pharmaceutical ingredient as described herein. A method of the present invention may comprise, consist essentially of, or consist of applying a nitric oxide-releasing pharmaceutical composition as described herein to the skin, mucosa, and/or eye of a subject to treat an inflammatory condition in the skin, mucosa, and/or eye in the subject, such as, but not limited to, by decreasing inflammation in the skin, mucosa, and/or eye of the subject. In some embodiments, a method of the present invention may be carried out in a manner such that the administration (e.g., topical administration) of the nitric oxide-releasing pharmaceutical composition does not produce systemic effects from the administration of nitric oxide. In some embodiments, a composition of the present invention, upon administration to a subject, does not produce systemic effects from the administration of nitric oxide. In some embodiments, a composition of the present invention may be a composition as described in PCT/US2014/050345 and/or PCT/US2015/013043, the contents of which are incorporated herein by reference in their entirety. A composition of the present invention may have a pH of less than about 7. In some embodiments, the composition may have a pH in a range of about 4 to about 7.

Any condition that is associated with inflammation and that may be treated topically to decrease or reduce such inflammation may be treated with a method of the present invention. Example inflammatory conditions include, but are not limited to, acneiform eruptions, alopecia areata, autoinflammatory syndromes, chronic blistering cutaneous conditions, conditions of the mucous membranes, conditions of the skin appendages, conditions of the subcutaneous fat, connective tissue diseases, abnormalities of dermal fibrous and elastic tissue, cutaneous congenital anomalies, dermal and subcutaneous growths, dermatitis, atopic dermatitis, contact dermatitis, eczema, pustular dermatitis, seborrheic dermatitis, disturbances of human pigmentation, drug eruptions, endocrine-related cutaneous conditions, eosinophilic cutaneous conditions, epidermal nevi, neoplasms, cysts, erythemas, genodermatoses, infection-related cutaneous conditions, bacterium-related cutaneous conditions, *mycobacterium*-related cutaneous conditions, mycosis-related cutaneous conditions, parasitic infestations, stings, and bites of the skin, virus-related cutaneous conditions, lichenoid eruptions, lymphoid-related cutaneous conditions, melanocytic nevi and neoplasms, melanoma, monocyte- and macrophage-related cutaneous conditions, mucinoses, neurocutaneous conditions, noninfectious immunodeficiency-related cutaneous conditions, papulosquamous hyperkeratotic cutaneous conditions, palmoplantar keratodermas, pregnancy-related cutaneous conditions, pruritic skin conditions, psoriasis, reactive neutrophilic cutaneous conditions, recalcitrant palmoplantar eruptions, skin conditions resulting from errors in metabolism, skin conditions resulting from physical factors, ionizing radiation-induced cutaneous conditions, urticaria and angioedema, vitiligo, and/or vascular-related cutaneous conditions. In some embodiments, the inflammatory condition is an inflammatory skin condition. In some embodiments, the inflammatory condition is an autoimmune inflammatory skin condition (i.e., an inflammatory skin condition that is caused by and/or related to an autoimmune disease or disorder). In some embodiments, the inflammatory condition is psoriasis and/or atopic dermatitis. In some embodiments, a composition of the present invention may be suitable for, formulated for, and/or used to treat at least two (e.g., 2, 3, 4, 5, or more) inflammatory conditions (e.g., psoriasis and/or atopic dermatitis).

In some embodiments, a method of the present invention may comprise treating acne. Acne may be treated in a subject according to a method of the present invention by decreasing inflammation in the skin of the subject. Accordingly, in some embodiments, a method of the present invention may comprise treating acne in a subject, the method comprising topically applying a nitric oxide-releasing pharmaceutical composition as described herein to the skin of the subject, thereby treating acne in the subject.

An inflammatory condition may be caused by a wound and/or an infection in the skin, mucosa, and/or eye of a subject. Accordingly, in some embodiments, a method of the present invention may comprise treating a wound and/or infection in the skin, mucosa, and/or eye of a subject, the method comprising topically applying a nitric oxide-releasing pharmaceutical composition as described herein to the skin, mucosa, and/or eye of the subject, thereby treating the wound and/or infection in the subject.

In some embodiments, a method of the present invention, such as, e.g., a method of treating an inflammatory condition and/or a method of decreasing inflammation, may comprise applying a nitric oxide-releasing pharmaceutical composition directly and/or indirectly on to the skin, mucosa, and/or eye of the subject. Applying a composition "directly" refers to applying the composition onto the surface of the skin, mucosa, and/or eye such that there are no barriers or intervening elements between the composition comprising the nitric oxide source and the skin, mucosa, and/or eye. Applying a composition "indirectly" refers to application of a nitric oxide source through a substrate, such as a cloth, dressing, membrane, or on top of another medicament, powder, ointment and the like.

While not wishing to be limited to any particular theory regarding the mechanism of action relating to nitric oxide releasing compounds as anti-inflammatory agents, nitric oxide may have an anti-inflammatory effect in acute and/or chronic inflammation. According to some embodiments, a method of the present invention may modulate the activity of one or more components (e.g., enzymes, transcription factors, cytokines, chemokines, second messengers, receptors, cells, adhesion molecules, etc.) in a pathway and/or signaling cascade involved in producing an acute and/or chronic inflammatory response in a subject to thereby decrease inflammation in the subject. For example, a method of the present invention may modulate the amount of one or more components involved in producing an inflammatory response in a subject to decrease inflammation in the subject. Alternatively or in addition, a method of the present invention may modulate the activation of one or more components involved in producing an inflammatory response in a subject, such as, but not limited to, by inhibiting or initiating the activation of the one or more components to decrease inflammation in the subject. In some embodiments, a method of the present invention may modulate a component's interactions (e.g., binding, signaling, etc.) with another component involved in producing an inflammatory response in a subject, such as, but not limited to, by inhibiting or initiating binding with another component, to decrease inflammation in the subject. In some embodiments, a method of the present invention may modulate the phosphorylation of a component, such as, but not limited to, a transcription factor, to decrease inflammation in a subject.

"Modulate," "modulating," and grammatical variations thereof as used herein refer to an increase or reduction in the activity of a component involved in producing acute and/or chronic inflammation in a subject compared to the activity of the component in the absence of a method of the present invention (e.g., the activity of the component prior to a method of the present invention, such as, e.g., prior to administering a composition of the present invention to the subject). As used herein, the terms "increase," "increases," "increased," "increasing" and similar terms (e.g., upregulate) indicate an elevation in activity of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more. As used herein, the terms "reduce," "reduces," "reduced," "reduction" and similar terms (e.g., downregulate, inhibit, etc.) refer to a decrease in activity of at least about 5%, 10%, 15%, 20%, 25%, 30%, 35%, 40%, 45%, 50%, 55%, 60%, 65%, 70%, 75%, 80%, 85%, 90%, 95%, 97% or more.

In some embodiments, a method of the present invention modulates a transcription factor. Example transcription factors include, but are not limited to, nuclear factor-kappa B (NF-kB), activator protein 1 (AP-1), nuclear factors of activated T cells (NF-ATs), signal transducers and activators of transcription (STATs), and any combination thereof. In some embodiments, a method of the present invention modulates NF-kB. Nitric oxide delivered at a site of inflammation may disrupt NF-kb mediated inflammation to modulate an inflammatory response in the skin, mucosa, and/or eye. For example, a method according to embodiments of the present invention may comprise topically administering a nitric oxide-releasing pharmaceutical composition in an amount effective to reduce and/or inhibit one or more of the following: NF-kB phosphorylation and/or degradation, translocation of NF-kB into the nucleus, NF-kB binding to a promoter region, and/or transcription of a cytokine produced and/or activated by NF-kB. In some embodiments, a method of the present invention comprises topically administering a nitric oxide-releasing pharmaceutical composition in an amount effective to down regulate and/or inhibit NK-kB and/or a NK-kB activity in the skin, mucosa, and/or eye of a subject, thereby treating an inflammatory condition, such as, but not limited to, psoriasis, acne, atopic dermatitis, an infection and the like, in the subject. In some embodiments, a method of the present invention may disrupt NK-kB mediated inflammation in the skin, mucosa, and/or eye of a subject, thereby decreasing inflammation in the skin, mucosa, and/or eye of the subject.

In some embodiments, a method of the present invention may modulate a cytokine. Example cytokines include, but are not limited to, Tumor necrosis factor-α (TNF-α), Intereukin-1 (IL-1), IL-2, IL-4, IL-5, IL-6, IL-8, IL-10, IL-12, IL-13, IL-17, IL-17a, IL-17f, IL-22, IL-23, IL-12/IL-23p40, KC/Gro, and any combination thereof. A method of the present invention may modulate (increase or decrease) the amount of a cytokine (e.g., a pro-inflammatory cytokine) present in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the amount of the cytokine present in a subject in the absence of a method of the present invention. In some embodiments, a method of the present invention inhibits the activation of a cytokine and/or reduces (e.g., downregulates) the production of a cytokine (e.g., a pro-inflammatory cytokine). In some embodiments, a method of the present invention activates a cytokine and/or increases (e.g., upregulates) the production of a cytokine. In some embodiments, a method of the present invention may disrupt the activation, production, and/or propagation of a cytokine (e.g., a pro-inflammatory cytokine) locally in the skin and/or may treat inflammation and/or an inflammatory skin disease (e.g., psoriasis), optionally without producing systemic effects from the administration of nitric oxide.

In some embodiments, a method of the present invention may comprise topically applying a nitric oxide-releasing pharmaceutical composition in an amount sufficient to modulate the production of IL-12 and/or IL-23, and/or may be used to treat inflammation and/or an inflammatory skin condition (e.g., psoriasis) in a subject. Alternatively or in addition, topical application of a nitric oxide-releasing compound according to embodiments of the present invention may modulate activation and/or production of TNF-α, IL-1α, IL-1β, IL-4, IL-8 and/or IL-10.

In some embodiments, a method of the present invention may comprise topically applying a nitric oxide-releasing pharmaceutical composition in an amount sufficient to modulate the production of IL-17A, IL-17F, and/or IL-1β, and/or may be used to treat inflammation and/or an inflammatory skin condition (e.g., psoriasis) in a subject. In some embodiments, a method of the present invention inhibits the activation of IL-17A, IL-17F, and/or IL-1β and/or reduces (e.g., downregulates) the production of IL-17A, IL-17F, and/or IL-1β. A method of the present invention may reduce the amount of (e.g., inhibit the activation and/or reduce the production of) IL-17A, IL-17F, and/or IL-1β in a subject by at least about 20%, 25%, 30%, 35%, 40%, 45%, 50%, 55%, 60%, 65%, 70%, 75%, 80%, 85%, 90%, 95%, or more compared to the amount of IL-17A, IL-17F, and/or IL-1β activated, produced, and/or present in a subject in the absence of a method of the present invention. In some embodiments, a method of the present invention may disrupt the activation, production, and/or propagation of IL-17A, IL-17F, and/or IL-1β locally in the skin of a subject and/or may treat inflammation and/or an inflammatory skin disease (e.g., psoriasis) without producing systemic effects from the administration of nitric oxide.

In some embodiments, a method of the present invention may comprise topically applying a nitric oxide-releasing pharmaceutical composition in an amount sufficient to modulate (e.g., reduce) the pro-inflammatory cytokines associated with perturbation of the IL-23/IL-17 axis.

In some embodiments, a method of the present invention may decrease inflammation associated with and/or due to a cytokine induced inflammation process and/or mechanism. In some embodiments, a method of the present invention may comprise topically administering a nitric oxide-releasing pharmaceutical composition in an amount effective to inhibit and/or downregulate the activity of TNFα in producing and/or activating an inflammatory response in a subject, thereby treating an inflammatory condition, such as, but not limited to, psoriasis, atopic dermatitis, acne, an infection and the like, in the subject. In some embodiments, a method of the present invention may comprise topically administering a nitric oxide-releasing pharmaceutical composition in an amount effective to inhibit, down regulate, and/or decrease at least one (e.g., 1, 2, 3, 4, 5, 6, 7, or more) inflammatory cytokine. In some embodiments, a method of the present invention may comprise topically administering a nitric oxide-releasing pharmaceutical composition in an amount effective to inhibit, down regulate, and/or decrease at least one (e.g., 1, 2, 3, 4, 5, 6, 7, or more) cytokine selected from the group consisting of TNFα, IL-1, IL-1α, IL-1β, IL-2, IL-4, IL-5, IL-6, IL-8, IL-10, IL-12, IL-13, IL-17, IL-17a, IL-17f, IL-22, IL-23, IL-12/IL-23p40, KC/Gro, and any combination thereof, thereby treating an inflammatory condition, such as, but not limited to, psoriasis, atopic dermatitis, acne, an infection and the like, in the subject. According to some embodiments, a method of the present invention may inhibit, down regulate, and/or decrease at least one (e.g., 1, 2, 3, 4, or 5) of IL-12/IL-23p40, IL-1β, IL-2, KC/Gro, and IL-6, thereby treating an inflammatory condition, such as, but not limited to, psoriasis, atopic dermatitis, acne, an infection and the like, in the subject. In some embodiments, a method of the present invention may inhibit, downregulate, and/or decrease at least one (e.g., 1, 2, 3, 4, or 5) of IL-1β, IL-6, IL-8, IL-10, IL-12, IL-17, IL-17a, IL-17f, and TNFα, thereby treating an inflammatory condition, such as, but not limited to, psoriasis, atopic dermatitis, acne, an infection and the like, in the subject.

In some embodiments, a method of the present invention may modulate a chemokine to thereby decrease inflammation in the skin, mucosa, and/or eye of the subject. For example, in some embodiments, a method of the present invention may decrease and/or inhibit the level of the chemokine RANTES in the skin, mucosa, and/or eye of a subject to thereby decrease inflammation in the skin, mucosa, and/or eye of the subject. In some embodiments, a method of the present invention may modulate an adhesion molecule, such as by decreasing, inhibiting, and/or down regulating the expression of one or more adhesion molecules in the skin, mucosa, and/or eye of a subject to thereby decrease inflammation in the skin, mucosa, and/or eye of the subject.

As those skilled in the art will recognize, inflammation may be Th1 and/or Th2 mediated. Th1 mediated inflammation may be involved in inflammatory conditions, such as psoriasis, and may produce Th1-type cytokines (e.g., interferon-gamma), which may provide a proinflammatory response. Th2 mediated inflammation may produce Th2-type cytokines (e.g., IL-4, IL-5, and IL-13), which may have an anti-inflammatory response. Th2-type cytokines may respond to counteract a Th1 mediated inflammation response. A method of the present invention may be used to treat Th1 and/or Th2 mediated inflammation. In some embodiments, a method of the present invention may increase Th2-type cytokines, thereby providing an anti-inflammatory response to treat an inflammatory condition. According to some embodiments, a method of the present invention may increase Th1-type cytokines to produce a pro-inflammatory response, and then may increase Th2-type cytokines to produce an anti-inflammatory response, thereby treating an inflammatory condition by decreasing inflammation.

In some embodiments, a method of the present invention may modulate the expression of a receptor, such as, but not limited to, a Toll-like receptor and/or a receptor involved in cell trafficking (e.g., E-selectin, E-cadherin, etc.). Modulation of a receptor's expression may reduce migration of inflammatory cells (e.g., myeloid-derived suppressor cells, basophils, lymphocytes, etc.) in the skin, mucosa, and/or eye of a subject. In some embodiments, topical application of a nitric oxide-releasing compound to the skin, mucosa, and/or eye of a subject may modulate (e.g., increase or decrease) expression of E-selectin or E-cadherin on endothelial cells and/or may modulate lymphocyte tethering and/or migration into the skin, mucosa, and/or eye of the subject. In some embodiments, topical application of a nitric oxide-releasing compound to the skin, mucosa, and/or eye of a subject may reduce the amount of lymphocytes present in the skin, mucosa, and/or eye of the subject.

According to some embodiments, a method of the present invention may modulate the presence of an inflammatory cell in the skin, mucosa, and/or eye of a subject. Example inflammatory cells include, but are not limited to, leukocytes such as neutrophils, basophils, mast cells, eosinophils, monocytes, and macrophages; lymphocytes such as B-lymphocytes and T-lymphocytes; natural killer cells; antigen-presenting cells such as dendritic cells (e.g., Langernah cells) and stromal cells; and any combination thereof. In certain embodiments, a method of the present invention may reduce the presence of an inflammatory cell in the skin, mucosa, and/or eye of a subject, thereby decreasing inflammation in a subject.

In some embodiments, a method of the present invention may decrease and/or inhibit the proliferation of keratinocytes in the skin, mucosa, and/or eye of a subject. Decreasing and/or inhibiting the proliferation of keratinocytes in the skin, mucosa, and/or eye of a subject may decrease inflammation in the skin, mucosa, and/or eye of the subject and may restore and/or initiate a normal healing process.

In some embodiments, a method of the present invention may modulate an oxidative process initiated by .NO$_2$ and/or .OH, such as, but not limited to by reducing or inhibiting the oxidative process. In some embodiments, a topically applied nitric oxide-releasing compound may act as an antioxidant at supraphysiological levels by scavenging peroxynitrite.

A method of the present invention may modulate one or more enzymes that may act in a pathway and/or signaling cascade involved in producing an acute and/or chronic inflammatory response in a subject. Example enzymes include, but are not limited to a matrix metalloproteinase (MMP) such as MMP-1, MMP-3, and MMP-9; a NADPH oxidase, a p450 dependent enzyme, a cyclooxygenase (COX) such as COX-1, COX-2, and COX-3; and any combination thereof. In some embodiments, a method of the present invention modulates NAD(P)H oxidase activity. In some embodiments, a method of the present invention reduces or inhibits a cyclooxygenase, thereby decreasing inflammation. A reduction or inhibition in the activity of a p450 dependent enzyme and/or a cyclooxygenase may decrease and/or inhibit prostaglandin to decrease inflammation in a subject.

A method of the present invention may be used to treat acne, such as, but not limited to, inflammation caused by acne. In some embodiments, a method of treating acne may comprise topically administering a nitric oxide-releasing pharmaceutical composition in an amount effective to decrease NF-kB activation and/or activating protein 1 (AP-1). In some embodiments, a method of treating acne may comprise topically administering a nitric oxide-releasing pharmaceutical composition in an amount effective to decrease production of at least one, such as 2, 3, 4, 5, 6, or more, of TNF-α, IL-1B, IL-8, IL-10, MMP-1, MMP-3, and MMP-9. A method of the present invention may comprise topically administering a nitric oxide-releasing pharmaceutical composition in an amount effective to decrease reactive oxygen species generated by *P. acnes* and/or decrease keratinocyte stimulation, thereby treating acne in a subject. In some embodiments, a method of the present invention may comprise topically administering a nitric oxide-releasing pharmaceutical composition in an amount effective to decrease and/or inhibit cytokine release from a Toll-like receptor (TLR), such as, but not limited to, TLR-2. A method of the present invention may decrease or inhibit a Th-1 mediated inflammation response, thereby treating acne in a subject. Alternatively or in addition, a method of the present invention may decrease or inhibit production and/or activation of IL-12 and/or IL-8 to treat acne in a subject.

During an inflammatory response to dermally-applied oxazolone, inflammatory cytokine production is up-regulated. Specifically, TNF-α levels may increase at the onset of inflammation (likely due to local irritation), followed by increased production of interferon-γ and a small increase in the production of interleukin-4 (likely from the infiltration of lymphocytes).

As a result of oxazolone-induced up-regulation of inflammatory cytokines, the production of peroxynitrite may be initiated. Peroxynitrite spontaneously decomposes to form the highly-reactive and destructive degradation products, .$NO_2$ and .OH. Increased NO production may inhibit the oxidative processes initiated by .$NO_2$ and .OH. Delivery of exogenous nitric oxide from a nitric oxide-releasing compound may, therefore, serve as an anti-inflammatory agent by serving as an anti-oxidant against nitrosative and oxidative species. Additionally, the exogenous release of NO during the inflammatory response to oxazolone may cause the down-regulation of the production of one or more of the above mentioned cytokines.

In some embodiments, a composition and/or method of the present invention may eliminate or reduce an infection in a subject. For example, in some embodiments, a composition and/or method of the present invention may eliminate or reduce a *Staphylococcus aureus* (e.g., methicillin-resistant *Staphylococcus aureus*) infection in the skin, mucosa, and/or eye of a subject. In some embodiments, a composition of the present invention may be antimicrobial. In some embodiments, a composition and/or method of the present invention may eliminate or maintain an infection (e.g., a *Staphylococcus aureus* infection) at a reduced and/or low level in the skin, mucosa, and/or eye of a subject. In some embodiments, a composition and/or method of the present invention may eliminate or reduce the presence of biofilms on the skin, mucosa, and/or eye of a subject. For example, a composition and/or method of the present invention may decrease bacteria and/or a biofilm present on the skin, mucosa, and/or eye of a subject by about 10%, 20%, 30%, 40%, 50%, 60%, 70%, 80%, 90%, 100%, 150%, 200%, 250%, 300%, 400%, 500%, or more. In some embodiments, a composition and/or method of the present invention may decrease bacteria and/or a biofilm present on the skin, mucosa, and/or eye of a subject by about 2, 3, 4-fold or more. In some embodiments, a composition and/or method of the present invention may provide at least a 1, 2, 3, 4, or 5-log reduction in bacterial burden and/or bacterial counts (e.g., *Staphylococcus aureus* bacterial counts) at 1, 2, 3, 4, 5, 6, 7, 8, 9, or 10 days after administration of the composition.

A method of the present invention may decrease the amount of inflammation, the rate of recurrence of inflammation, an inflammatory flare, and/or an infection (e.g., a *Staphylococcus aureus* infection) in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the amount of inflammation, the rate of recurrence of inflammation, the inflammatory flare, and/or the infection (e.g., a *Staphylococcus aureus* infection) in the absence of a method of the present invention. In some embodiments, the amount of inflammation, the rate of recurrence of inflammation, the inflammatory flare, and/or the infection (e.g., a *Staphylococcus aureus* infection) in the subject may be compared to the administration of a treatment not in accordance with the present invention (e.g., compared to the rate of recurrence associated with a topical corticosteroid) or compared to the values (e.g., the amount of inflammation or rate of recurrence) prior to treatment with a method of the present invention. The rate of recurrence may be determined using methods known to those of skill in the art. For example, after a treatment of inflammation, reinfection may be determined after a given period of time to determine the rate of recurrence.

A nitric oxide-releasing pharmaceutical composition as described herein may comprise, consist essentially of, or consist of at least one NO-releasing compound as a nitric oxide-releasing active pharmaceutical ingredient (API). Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 μm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include, but are not limited to, nitrosamine, hydroxyl nitrosamine, hydroxyl amine and hydroxyurea. Any suitable combination of NO donors and/or NO-releasing compounds may also be used in a composition (e.g., an admixture or a hydrophobic composition) as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Pat. No. 8,282,967, 8,962,029 or U.S. Pat. Nos. 8,956,658, 9,403,851, 9,403,852, the disclosures of which are incorporated by reference herein in their entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures" and U.S. Pat. No. 9,238,038; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, U.S. Pat. Nos. 8,937,143, and 9,267,006, the disclosures of which are incorporated herein by reference in their entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In one embodiment of the present invention, the nitric oxide donor may be an N-diazeniumdiolate. In some embodiments of the present invention, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine (e.g., a secondary amine) substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''—(NH—R')_n—Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl) phenethyltrimethoxysilane (AEMP3); [3-(methylamino) propyl]trimethoxysilane (MAP3); N-butylamino-propyltrimethoxysilane(n-BAP3); t-butylamino-propyltrimethoxysilane(t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: $NH [R'—Si(OR)_3]_2$, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl) propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: $R''—N(NONO—X+)—R'—Si(OR)3$, wherein R is alkyl, R' is alkylene or aralkylene, R" is alkyl or alkylamine, and $X^+$ is a cation selected from the group consisting of $Na^+$, $K^+$ and $Li^+$.

The composition of the siloxane network, (e.g., amount or the chemical composition of the aminoalkoxysilane) and the nitric oxide charging conditions (e.g., the solvent and base) may be varied to optimize the amount and/or duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of $R''—N(NONO—X^+)—R'—Si(OR)_3$, wherein: R is alkyl, R' is alkylene or aralkylene, R" is alkyl or alkylamine, and $X^+$ is a cation selected from the group consisting of $Na^+$ and $K^+$.

In certain embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAP3) and tetra methyl orthosilicate (TMOS) and/or a co-condensed silica network comprising diazeniumdiolated methylaminopropyl trimethoxysilane (MAP3) and tetraethyl orthosilicate (TEOS). In some embodiments, a composition of the present invention does not comprise a NO-releasing API comprising a co-condensed silica network comprising diazeniumdiolated methylaminopropyl trimethoxysilane (MAP3) and tetraethyl orthosilicate (TEOS). In some embodiments, the NO-releasing API is a diazeniumdiolate functionalized co-condensed silica particle having a releasable NO content in a range of about 13% to about 17% by weight of the particle. The amount of nitric oxide released may be determined using real time in vitro release testing. In some embodiments, nitric oxide release may be determined using a chemiluminescent nitric oxide analyzer.

In some embodiments of the invention, the particle size of a NO-releasing API may be in a range of about 20 nm to about 20 μm or any range therein, such as, but not limited to, about 100 nm to about 20 μm or about 1 μm to about 20 μm. The particle size may be tailored to minimize or prevent toxicity and/or penetration through the epidermis (or compromised dermis) and into the blood vessels. In some embodiments, the particle size is distributed around a mean particle size of less than 20 μm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 6, 5, 4, 3, 2, or 1 μm. In further embodiments, a NO-releasing API may have a particle size that is distributed around a mean particle size of less than 10 μm, or any range therein, such as, but not limited to about 2 μm to about 10 μm or about 4 μm to about 8 µm. In other embodiments, the particle size may be distributed around a mean particle size of greater than 20 µm, or any range therein, and the size may prevent the particle from entering the follicle. In still further embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

A composition of the present invention may comprise a NO-releasing API and may store and/or release nitric oxide in an amount of about 0.05% to about 10% by weight of the composition, such as, but not limited to, about 0.15% to about 2%, about 0.15% to about 1%, about 0.3% to about 1.2%, about 0.15% to about 6%, about 1% to about 10%, about 3% to about 6%, or about 1% to about 5% by weight of the composition. In certain embodiments, a composition of the present invention may comprise a nitric oxide-releasing active pharmaceutical and may store and/or release nitric oxide in an amount of about 0.15%, 0.3%, 0.6%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or 10% by weight of the composition. The amount of nitric oxide released may be determined using real time in vitro release testing. In some embodiments, nitric oxide release may be determined using a chemiluminescent nitric oxide analyzer.

The compositions described herein may also include one or more additional APIs. Any suitable additional API or combinations, of APIs may be included in the compositions according to embodiments of the invention. Examples of APIs include antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents and mixtures thereof.

Examples of antimicrobial agents include, but are not limited to, penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of topical anti-acne agents include, but are not limited to, adapalene, azelaic acid, benzoyl peroxide, clindamycin and clindamycin phosphate, doxycycline, erythromycin, keratolytics such as salicylic acid and retinoic acid (Retin-A"), norgestimate, organic peroxides, retinoids such as isotretinoin and tretinoin, sulfacetamide sodium, and tazarotene. Particular anti-acne agents include adapalene, azelaic acid, benzoyl peroxide, clindamycin (e.g., clindamycin phosphate), doxycycline (e.g., doxycycline monohydrate), erythromycin, isotretinoin, norgestimate, sulfacetamide sodium, tazarotene, etretinate and acetretin.

Examples of antihistamine agents include, but are not limited to, diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include, but are not limited to, alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include, but are not limited to, nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include, but are not limited to, alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include, but are not limited to, alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include, but are not limited to, thrombin, phytonadione, protamine sulfate, aminocaproic acid, tranexamic acid, carbazochrome, carbaxochrome sodium sulfanate, rutin and hesperidin.

A nitric oxide-releasing pharmaceutical composition as described herein may comprise any suitable pharmaceutical composition comprising at least one NO-releasing compound. Example nitric oxide-releasing pharmaceutical compositions include, but are not limited to, those described in International Publication Nos. WO 2011/022652, WO 2013/063354, WO 2013/006608, WO 2013/138075, WO 2015/021382, and WO 2016/022170, the disclosures of each of which are incorporated herein by reference in their entirety. In addition, a nitric oxide-releasing pharmaceutical composition described herein may be prepared as described in International Publication No. WO 2013/006613, the disclosure of which is incorporated herein by reference in its entirety. In some embodiments, a composition of the present invention does not comprise an alcohol, such as, for example, ethanol and/or isopropyl alcohol.

In some embodiments, a composition (e.g., an ointment) containing nitrosothiol-modified compounds may be kept at a low temperature (e.g, less than about 0° C.) to minimize thermal decomposition and NO release. The cold composition may then be applied to the skin, mucosa, and/or eye and the elevated temperature of the skin, mucosa, and/or eye may allow for the release of NO. In some embodiments, the nitrosothiol may be present in a medicament (e.g., a hydrophilic formulation which may limit NO diffusion) such that it is stable at room temperature due to cage effects, and then releases NO upon application to the skin, mucosa, and/or eye. Light may also be applied to a medicament that includes nitrosothiol modified compounds. The application of light in fluxes may be applied to create fluxes of NO.

According to some embodiments, a nitric oxide-releasing pharmaceutical composition as described herein may comprise an ointment, salve, cream, and/or the like. A nitric oxide-releasing ointment, salve, cream, and/or the like may comprise a hydrophobic base, an amphiphilic compound, and at least one NO-releasing compound. "Hydrophobic base" as used herein refers to a natural and/or synthetic fat, wax, oil, and/or the like. In some embodiments, a hydrophobic base may comprise a hydrophobic polymer. "Amphiphilic compound" as used herein refers to a compound comprising hydrophilic and hydrophobic properties.

In some embodiments, a nitric oxide-releasing pharmaceutical composition, as described herein, comprises a composition as described in International Publication No. WO 2013/138075, WO 2015/021382, and/or WO 2016/022170, the disclosures of each of which are incorporated herein by reference in their entirety. For example, a nitric oxide-releasing pharmaceutical composition may comprise at least one NO-releasing compound present in the composition at a concentration from about 0.1% to about 35% by weight of the composition; a hydrophobic polymer present in the composition at a concentration from about 30% to about 60% by weight of the composition; a mineral oil present in the composition at a concentration from about 1% to about 30% by weight of the composition; an amphiphilic compound present in the composition at a concentration from about 1% to about 20% by weight of the composition; a cosolvent present in the composition at a concentration from about 1% to about 25% by weight of the composition; and a humectant present in the composition at a concentration from about 1% to about 25% by weight of the composition.

In some embodiments, a nitric oxide-releasing pharmaceutical composition of the present invention may comprise two compositions that may be and/or are admixed together, a first composition comprising a hydrophobic composition and a second composition comprising a hydrogel. Thus, in some embodiments, the nitric oxide-releasing pharmaceutical composition is an admixture. The hydrophobic composition may comprise a hydrophobic base and an amphiphilic compound, and may be an ointment. In some embodiments, the hydrophobic composition may comprise a NO-releasing API in an amount of about 0.1% to about 50% by weight of the hydrophobic composition, one or more (e.g., 1, 2, 3, or more) hydrocarbon and/or hydrophobic base(s), each of which may be present in an amount of about 1% to about 90% by weight of the hydrophobic composition, an amphiphilic compound in an amount of about 0% to about 15% by weight of the composition, and optionally one or more (e.g., 1, 2, 3, or more) excipients (e.g., emulsifiers, etc.), each of which may be present in an amount of about 0% to about 30% by weight of the composition. In some embodiments, at least one of the one or more excipients may be a solvent, which may be present in an amount of about 1% to about 15% by weight of the composition.

The hydrogel may comprise water, a buffering agent, a humectant, and/or a viscosity-modifying agent. In some embodiments, the hydrogel may comprise phosphate, such as, for example, a phosphate buffering agent, and/or may comprise cellulose, such as, for example, hydroxyethyl cellulose. In some embodiments, the hydrogel may comprise acetate, such as, for example, an acetate buffering agent, and/or may comprise a cellulose, such as, for example, a carboxymethylcellulose. In some embodiments, a nitric oxide-releasing pharmaceutical composition of the present invention may comprise a hydrogel that comprises acetic acid and an acetate, such as, e.g., sodium acetate. In some embodiments, the hydrogel may have a pH in a range of about 4 to about 5.5.

A nitric oxide-releasing pharmaceutical composition and/or hydrogel of the present invention may comprise one or more buffering agents in an amount of about 5 mmol to about 2 mol of the hydrogel and/or composition. In some embodiments, one or more buffering agents may be present in the hydrogel in an amount of about 1% to about 20% by weight of the hydrogel, such as, for example, about 1% to about 15% or about 2% to about 10% by weight of the hydrogel. In some embodiments, a buffering agent is present in a hydrogel of the present invention in an amount of about 1, 2, 3, 4, 5, 6, 7, 8, 9, 10, 11, 12, 13, 14, 15, 16, 17, 18, 19, or 20% by weight of the hydrogel.

According to some embodiments of the present invention, a nitric oxide-releasing pharmaceutical composition of the present invention (e.g., an admixture as described herein) may be a pH-controlled composition. In some embodiments, a pH-controlled composition of the present invention may have a pH in a range from 4 to 6.5 at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours after administration and/or combination (e.g., where a nitric oxide-releasing pharmaceutical composition comprises at least two compositions that are admixed together, such as a hydrophobic composition and hydrogel). The pH of a composition of the present invention may be measured in vitro at one or more given time points using a pH probe (e.g., a flat end pH probe) and meter and measuring at three different locations within the composition, then averaging these measurements to determine the time point pH value. When a composition is measured in vitro, formation of the composition (e.g., combination of two or more compositions to form an admixture) may be used as equivalent or comparative in time to administration of the composition to a subject.

In some embodiments, a pH-controlled composition of the present invention may have a pH in a range from 4.0 to 6.0, 4.5 to 6.0, 4.5 to 5.5, 5.25 to 5.75, 4.5 to 5.0, 4.5 to 4.75, 4.75 to 5.0, 5.5 to 5.75, or 5.25 to 5.5 at a time point from 1 to 48 hours after administration and/or combination. In some embodiments, a nitric oxide-releasing pharmaceutical composition of the present invention may be a pH-controlled composition and the pH may vary by less than ±0.2 (such as, e.g., less than ±0.2, 0.15, 0.1, 0.05, or 0.01) at two or more different time points between 1 hour after administration and/or combination and 48 hours after administration and/or combination, such as, for example, between 1, 2, 4, or 6 hour(s) after administration and/or combination and 12, 24, or 36 hours after administration and/or combination. In some embodiments, a pH-controlled composition of the present invention may have a pH in a range from 4.0 to 6.5 at 1 hour after administration and/or combination and at 24 hours after administration and/or combination, and the pH value at these time points may vary by less than ±0.2. In some embodiments, a pH-controlled composition of the present invention may have a pH in a range from 4.5 to 6.5 at 1 hour after administration and/or combination and at 24 hours after administration and/or combination, and the pH value at these time points may vary by less than ±0.2.

In some embodiments, a pH-controlled composition of the present invention may maintain a pH in a range from 4.0 to 6.5 for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 consecutive hours or more after administration and/or combination. In some embodiments, a pH-controlled composition of the present invention may maintain the pH in a range from 4.0 to 6.0, 4.5 to 6.0, 4.5 to 5.5, 5.25 to 5.75, 4.5 to 5.0, 4.5 to 4.75, 4.75 to 5.0, 5.5 to 5.75, or 5.25 to 5.5. In some embodiments, a nitric oxide-releasing pharmaceutical composition of the present invention may be a pH-controlled composition and the pH may vary by less than ±0.2 (such as, e.g., less than ±0.2, 0.15, 0.1, 0.05, or 0.01) in a time period between 1 hour after administration and/or combination and 48 hours after administration and/or combination, such as, for example, between 1, 2, 4, or 6 hour(s) after administration and/or combination and 12, 24, or 36 hours after administration and/or combination. In some embodiments, a pH-controlled composition of the present invention may maintain a pH in a range from 4.0 to 6.5 for at least about 23 or 24 hours and may vary during that time by less than ±0.2. In some embodiments, a pH-controlled composition of the present invention may maintain a pH in a range from 4.5 to 6.5 for at least about 23 or 24 hours and may vary during that time by less than ±0.2.

According to some embodiments, a nitric oxide-releasing pharmaceutical composition of the present invention may not have a pH over 6.0, 6.1, 6.2, 6.3, 6.4, 6.5, 6.6, 6.7, 6.8, 6.9, or 7.0 at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hour(s) after administration and/or combination. This may allow for higher concentrations of a NO-releasing active pharmaceutical ingredient (e.g., 2% to 30% of a NO-releasing active pharmaceutical ingredient by weight of the composition) to be administered while maintaining a slightly acidic nature.

According to some embodiments of the present invention provided are nitric oxide-releasing pharmaceutical compositions, which are described in further detail below. In some embodiments, a nitric oxide-releasing pharmaceutical composition of the present invention (e.g., an ointment and/or cream) may comprise an excipient that enhances, increases, and/or improves the spreadability and/or feel of the composition, such as, for example, a silicon containing compound. Example silicon containing compounds include, but are not limited to, silicones (e.g., cyclomethicone), siloxanes (e.g., dimethicone), and/or silicone elastomers (e.g., Dow Corning® ST-Elastomer 10 available from Dow Corning Corporation, which is a combination of a silicone elastomer and a volatile silicone fluid). In some embodiments, a silicon containing compound may be present in a hydrophobic composition of the present invention in an amount of about 1% to about 30% by weight of the hydrophobic composition. In some embodiments, a silicon containing compound may be present in the hydrophobic composition in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% by weight of the hydrophobic composition. In some embodiments, two or more silicon containing compounds may be present in a hydrophobic composition of the present invention, with each being present in an amount of about 1% to about 30% by weight of the hydrophobic composition.

In some embodiments, a hydrophobic composition of the present invention may be a liquid, solution, ointment, and the like. The hydrophobic composition may comprise at least one hydrophobic component, such as, but not limited to, a hydrophobic base. Example hydrophobic compositions include those described in International Application Nos. PCT/US2010/046173 and PCT/US2013/028223, which are each incorporated herein by reference in their entirety. In some embodiments, the hydrophobic composition is an ointment.

At least one hydrophobic base may be present in a hydrophobic composition of the present invention. Any suitable hydrophobic base may be used in a hydrophobic composition of the present invention. In certain embodiments, a hydrophobic composition comprises two or more hydrophobic bases, such as, but not limited to, 2, 3, 4, 5, or more hydrophobic bases. In certain embodiments, a hydrophobic base in addition to having hydrophobic properties, may also have hydrophilic properties and thus may be an amphiphilic base. Example hydrophobic bases include, but are not limited to, branched and unbranched hydrocarbons, branched and unbranched hydrocarbon waxes, vaseline, hydrocarbon gel, liquid paraffin, white petrolatum, petrolatum, microcrystalline wax, andelilla wax, carnauba wax, lanolin (wool wax), wool wax alcohol, esparto grass wax, cork wax, guaruma wax, rice bran wax, sugar cane wax, berry wax, ouricury wax, soy wax, jojoba oil, uropygial grease, ceresine, paraffin waxes, micro waxes, plant oils, animal oils, carnauba wax, beeswax, cacao butter, hard fat, mineral oil, vegetable oil, avocado oil, borage oil, canola oil, castor oil, chamomile oil, coconut oil, corn oil, cottonseed oil, rapeseed oil, evening primrose oil, safflower oil, sunflower oil, soybean oil, sweet almond, palm oil, palm kernel oil, *arctium lappa* seed oil, sesame oil, borgo officialis seed oil, *brassica campestris* oleifera oil, brevoortia oil, bubulum oil, cistus ladaniferus oil, *Elaeis guineensis* oil, almond oil, pine oil, olive oil, peanut oil, wheat germ oil, grape seed oil, thistle oil, lard, tallow, palm olein, illipe butter, shea butter, cocoa butter, kokum butter, sal butter, lecithin, japan wax lanolin, partially hydrogenated vegetable oils, hydrophobic polymers, and any combination thereof.

In some embodiments, a hydrophobic base may comprise a hydrophobic polymer. Any suitable hydrophobic polymer may be used in a hydrophobic composition of the present invention. Example hydrophobic polymers include, but are not limited to hydrocarbon polymers and/or co-polymers, aromatic polyurethanes, silicone rubber, polysiloxanes, polycaprolactone, polycarbonate, polyvinylchloride, polyethylene, polyethylene glycols (6-4000), poly-L-lactide, poly-DL-glycolide, polyetheretherketone (PEEK), polyamide, polyimide and polyvinyl acetate. In certain embodiments, a hydrophobic base may be an amphiphilic base, such as, but not limited to, a polyethylene glycol (6-4000). In particular embodiments of the present invention, a hydrophobic composition of the present invention comprises one or more hydrocarbon polymers and/or co-polymers. In certain embodiments, a hydrophobic composition of the present invention may comprise one or more hydrocarbon polymers and/or co-polymers, such as, but not limited to, those commercially available from Calumet Specialty Products Partners of Indianapolis, Ind. under the trademark Versagel® and/or those commercially available from Croda International Plc of East Yorkshire, United Kingdom under the trade name Crodabase SQ, which comprises mineral oil and polyethylene.

In some embodiments, a hydrophobic composition may comprise at least one hydrophobic base comprising one or more plant and/or mineral oils. Any suitable oil may be used in a hydrophobic composition of the present invention. Example mineral oils include, but are not limited to, light mineral oil, white mineral oil, paraffinic oils, naphtenic oils, aromatic oils, and any combination thereof.

One or more hydrophobic bases may be present in a hydrophobic composition used to form an admixture of the present invention. One or more hydrophobic bases (e.g., 1, 2, 3, 4, 5 or more hydrophobic bases), alone or together, may be present in a hydrophobic composition at a concentration from about 1% to about 99% by weight of the hydrophobic composition or any range and/or individual value therein, such as, but not limited to, from about 2% to about 20% by weight, about 1% to about 10% by weight, about 1% to about 15% by weight, about 15% to about 65% by weight, about 25% to about 98% by weight, about 30% to about 98% by weight, about 35% to about 99% by weight, about 35% to about 90% by weight, about 25% to about 50% by weight, about 25% to about 55% by weight, about 30% to about 50% by weight, about 35% to about 55% by weight, about 40% to about 80% by weight, about 50% to about 90% by weight, about 65% to about 95% by weight, about 70% to about 80% by weight, about 75% to about 95% by weight, about 80% to about 99% by weight, about 90% to about 99% by weight, or about 50% to about 70% by weight of the hydrophobic composition. In certain embodiments, one or more hydrophobic bases, alone or together, may be present in a hydrophobic composition used to form an admixture at a concentration from about 50% to about 90% by weight of the hydrophobic composition. In some embodiments, one or more hydrophobic bases, alone or together, may be present in a hydrophobic composition used to form an admixture at a concentration from about 70% to about 99% by weight of the hydrophobic composition.

At least one amphiphilic compound may be present in a hydrophobic composition of the present invention. An amphiphilic compound may comprise two or more compounds, each of which may provide the hydrophilic property and/or the hydrophobic property. In some embodiments, the amphiphilic compound may comprise one compound having hydrophilic and hydrophobic properties. In some embodiments of the present invention, an amphiphilic compound may absorb moisture without substantially absorbing vaporous moisture. An amphiphilic compound may have a hydrophilic-lipophilic balance (HLB) value of 12 to 20 or any range and/or individual value therein, such as, but not limited to, 15 to 20 or 18 to 20. In certain embodiments of the present invention, an amphiphilic compound may have a HLB value of 19.

Example amphiphilic compounds include, but are not limited to, fatty acid esters. One or more fatty acid ester(s) may be present in an admixture of the present invention, such as 2, 3, 4, or more fatty acid esters. Example fatty acid esters include, but are not limited to, $C_6$-$C_{22}$ alkyl and/or alkenyl fatty acid esters such as methyl laurate, ethyl laurate, ethyl myristate, ethyl palmitate, ethyl linoleate, propyl isobutylate, isopropyl laurate, isopropyl myristate, isopropyl palmitate, oleyl myristate, oleyl stearate, and oleyl oleate; ether-esters such as fatty acid esters of ethoxylated fatty alcohols; polyhydric alcohol esters such as ethylene glycol mono- and di-fatty acid esters, diethylene glycol mono- and di-fatty acid esters; polyethylene glycol (6-2000) fatty acid mono- and/or diesters such as PEG-6-laurate, PEG-6-stearate, PEG-8-dilaurate, PEG-8-distearate, etc.; polyethylene glycol glycerol fatty acid esters such as PEG-20-glyceryl laurate, PEG-20-glyceryl stearate, and PEG-20-glyceryl oleate; propylene glycol mono- and di-fatty acid esters; polypropylene glycol 2000 monooleate; polypropylene glycol 2000 monostearate; ethoxylated propylene glycol monostearate; glyceryl mono- and di-fatty acid esters; polyglycerol fatty acid esters such as polyglyceryl-10 laurate, etc.; ethoxylated glyceryl monostearate; 1,3-butylene glycol monostearate; 1,3-butylene glycol distearate; polyoxyethylene polyol fatty acid ester; sorbitan fatty acid esters including sorbitan trioleate and sorbitan monolaurate; polyethylene glycol sorbitan fatty acid esters such as PEG-6 sorbitan monooleate; polyoxyethylene sorbitan fatty acid esters including polyoxyethylene (20) sorbitan monolaurate; sucrose fatty acid esters such as saccharose monopalmitate and saccharose monostearate; wax esters such as beeswax, spermaceti, myristyl myristate, stearyl stearate and arachidyl behenate; polyethylene glycol alkyl ethers such as PEG-10 oleyl ether or PEG-9 cetyl ether; polyethylene glycol alkyl phenols such as PEG-10-100 nonyl phenol; polyoxyethylene-polyoxypropylene block copolymers such as poloxamer 188; sterol esters such as cholesterol fatty acid esters, and any combination thereof.

In certain embodiments, a fatty acid ester may comprise a polyethylene glycol (PEG) glyceride. The polyethylene glycol portion of a PEG glyceride may provide the hydrophilic property of an amphiphilic compound and may include, but is not limited to, PEG 5-1000 or any range and/or individual value therein, and any combination thereof. The glyceride portion of a PEG glyceride may provide the hydrophobic property of an amphiphilic compound and may include, but is not limited to, a natural and/or hydrogenated oil, such as but not limited to, castor oil, hydrogenated castor oil, vitamin A, vitamin D, vitamin E, vitamin K, a plant oil (e.g., corn oil, olive oil, peanut oil, palm kernel oil, apricot kernel oil, almond oil, etc.), and any combination thereof. Example polyethylene glycol (PEG) glycerides include, but are not limited to, PEG-20 castor oil, PEG-20 hydrogenated castor oil, PEG-20 corn glycerides, PEG-20 almond glycerides; PEG-23 trioleate, PEG-40 palm kernel oil, PEG-8 caprylic/capric glycerides, PEG-6 caprylic/capric glycerides, lauroyl macrogol-32 glyceride, stearoyl macrogol glyceride, tocopheryl PEG-1000 succinate, and any combination thereof. In some embodiments, a fatty acid ester may comprise a PEG 5-30 (i.e., PEG 5, 6, 7, 8, 9, 10, etc.) and a caprylic/capric glyceride. In particular embodiments, an admixture may comprise a PEG-5-caprylic/capric glyceride, a PEG-6-caprylic/capric glyceride, a PEG-7-caprylic/capric glyceride, and/or a PEG-8-caprylic/capric glyceride. In certain embodiments, an admixture may comprise one or more fatty acid esters such as, but not limited to, those commercially available from Sasol of Hamburg, Germany under the trademark SOFTIGEN®.

An amphiphilic compound may be present in a hydrophobic composition used to form an admixture of the present invention at a concentration from about 0.5% to about 30% by weight of the hydrophobic composition or any range and/or individual value therein, such as, but not limited to, from about 0.5% to about 10% by weight, about 2% to about 20% by weight, about 1% to about 10% by weight, about 1% to about 5% by weight, or about 5% to about 15% by weight of the hydrophobic composition. In certain embodiments, an amphiphilic compound may be present in a hydrophobic composition used to form an admixture of the present invention at a concentration of about 10% by weight of the hydrophobic composition. In some embodiments, an amphiphilic compound may be present in a hydrophobic composition used to form an admixture of the present invention at a concentration of from about 0.5% to about 10% by weight of the hydrophobic composition.

An admixture of the present invention may further comprise one or more excipients. In some embodiments, one or more excipients may be present in a hydrophobic composition that may be used to form an admixture of the present invention. Excipients for use in pharmaceutical compositions are well-known in the art and examples may be found in the Handbook of Pharmaceutical Excipients (Rowe, R. C. et al., APhA Publications; 5th ed., 2005). Classes of excipients may include, but are not limited to, an emollient, a humectant, a cosolvent, a pH modifier, a water repelling agent, an anti-foaming agent, a surfactant, a solubilizer, an emulsifying agent, a wetting agent, a penetration enhancer, an antioxidant, and/or a solvent. The excipients may be present in an admixture of the present invention at any suitable concentration. In some embodiments, an excipient may be present in a hydrophobic composition used to form an admixture of the present invention at a concentration from about 1% to about 30% by weight of the hydrophobic composition or any range and/or individual value therein, such as, but not limited to, from about 1% to about 15% by weight, about 1% to about 10% by weight, about 1% to about 20%, about 5% to about 15%, or about 5% to about 10% by weight of the hydrophobic composition.

In some embodiments, a hydrophobic composition may comprise a cosolvent. A cosolvent may be present in a hydrophobic composition used to from an admixture of the present invention at a concentration from about 1% to about 30% by weight of the hydrophobic composition or any range and/or individual value therein, such as, but not limited to, from about 1% to about 15% by weight, about 1% to about 20% by weight, about 2% to about 20% by weight, about 5% to about 25% by weight, or about 5% to about 15% by weight of the hydrophobic composition. In certain embodiments of the present invention, a cosolvent may be present in a hydrophobic composition used to form an admixture of the present invention at a concentration from about 10% to about 15% by weight of the hydrophobic composition. In some embodiments, a cosolvent may be present in a hydrophobic composition used to form an admixture of the present invention at a concentration of from about 1% to about 15% by weight of the hydrophobic composition.

Example cosolvents include, but are not limited to, a fatty acid ester, propylene glycol, glycerol, polyethylene glycol, a silicone such as cyclomethicone, and any combination thereof. In some embodiments, a cosolvent may comprise a neutral oil. In certain embodiments, a cosolvent comprises a caprylic and/or capric fatty acid ester, such as a caprylic and/or capric triglyceride. Example cosolvents include, but are not limited to, those commercially available from Sasol of Hamburg, Germany under the trademark MIGLYOL®.

An admixture may comprise a humectant. Any suitable humectant or combination of humectants may be used. A humectant may be present in a hydrophobic composition used to form an admixture of the present invention at a concentration from about 1% to about 25% by weight of the hydrophobic composition or any range and/or individual value therein, such as, but not limited to, from about 1% to about 15% by weight, about 2% to about 20% by weight, about 5% to about 10% by weight, or about 5% to about 15% by weight of the hydrophobic composition. In certain embodiments, a humectant may be present in a hydrophobic composition used to form an admixture of the present invention at a concentration from about 10% to about 15% by weight of the hydrophobic composition.

Example humectants include, but are not limited to, polyhydric alcohols, such as glycols such as diethylene glycol monoethyl ether and methoxypolyethyleneglycol; glycerols such as propylene glycol, glycerol, isopropanol, ethanol, ethylene glycol, polyethylene glycol, ethoxydiglycol or mixtures thereof; sugar polyols, such as sorbitol, xylitol and maltitol; polyols such as polydextroses; dimethyl isosorbide; *quillaia*; urea; and any combination thereof. In particular embodiments of the present invention, a humectant comprises an alkylene glycol, such as hexylene glycol, butylene glycol, pentylene glycol, and any combination thereof.

An admixture may comprise an emulsifying agent. Any suitable emulsifying agent or combination of emulsifying agents may be used. An emulsifying agent may be present in a hydrophobic composition used to form an admixture of the present invention at a concentration from about 1% to about 30% by weight of the hydrophobic composition or any range and/or individual value therein, such as, but not limited to, from about 2% to about 20% by weight, about 5% to about 15% by weight, about 10% to about 30%, by weight, about 25% to about 30% by weight, or about 5% to about 30% by weight of the hydrophobic composition. In certain embodiments, an emulsifying agent may be present in a hydrophobic composition used to form an admixture of the present invention at a concentration from about 5% to about 15% by weight of the hydrophobic composition.

Example emulsifying agents include, but are not limited to, glycerol monostearate; mono/di glycerides; phosphatidyl cholines; lecithin; surfactants such as polyethoxylated compounds including tween 80 polysorbate 20, 21, 40, 60, 61, 65, 81, 85, 120 and other polyoxyethylene adducts of sorbitan esters, fatty acids, fatty alcohols, lanolin, lanolin alcohols, castor oil (natural or hydrogenated), or alkylbenzenes; emulsifier 10 commercially available from DOW CORNING®; fatty alcohols such as cetyl alcohol, stearyl alcohol, behenyl alcohol, myristyl alcohol, and cetostearyl alcohol; fatty acid esters such as those commercially available from Sasol of Hamburg, Germany under the trademark MIGLYOL®; and any combination thereof.

According to some embodiments, a hydrophobic composition of the present invention may comprise an API, such as, but not limited to, a nitric oxide-releasing API, a hydrophobic base, an amphiphilic compound, and an emulsifying agent. In some embodiments, the API may be a NO-releasing API, the hydrophobic base may be a hydrophobic polymer comprising a combination of mineral oil and polyethylene, the amphiphilic compound may be a PEG-6-caprylic/capric glyceride, and the emulsifying agent may be cetyl alcohol. In some embodiments, the API may be a NO-releasing API, the hydrophobic base may be a hydrophobic polymer comprising a combination of mineral oil and polyethylene, the amphiphilic compound may be a PEG-6-caprylic/capric glyceride, and the emulsifying agent may be glycerol monostearate. The API may be present in an amount of about 0.1% to about 30% by weight of the hydrophobic composition, the hydrophobic base may be present in an amount of about 50% to about 95% by weight of the hydrophobic composition, the amphiphilic compound may be present in an amount of about 1% to about 20% by weight of the hydrophobic composition, and the emulsifying agent may be present in an amount of about 1% to about 20% by weight of the hydrophobic composition. In some embodiments, the hydrophobic composition may be in the form of an ointment.

According to some embodiments, a hydrophobic composition of the present invention may comprise an API, such as, but not limited to, a nitric oxide-releasing API, a hydrophobic base, an amphiphilic compound, and a silicon containing compound. In some embodiments, the API may be a NO-releasing API, the hydrophobic base may be a hydrophobic polymer comprising a combination of mineral oil and polyethylene, the amphiphilic compound may be a PEG-6-caprylic/capric glyceride, and the silicon containing compound may be cyclomethicone and/or a silicone elastomer (e.g., ST-Elastomer 10). In some embodiments, the hydrophobic composition comprises cyclomethicone and a silicone elastomer (e.g., ST-Elastomer 10). The API may be present in an amount of about 0.1% to about 30% by weight of the hydrophobic composition, the hydrophobic base may be present in an amount of about 50% to about 95% by weight of the hydrophobic composition, the amphiphilic compound may be present in an amount of about 1% to about 20% by weight of the hydrophobic composition, and the silicon containing compound may be present in an amount of about 1% to about 30% by weight of the hydrophobic composition. In some embodiments, the hydrophobic composition may be in the form of an ointment.

A hydrogel of the present invention may be configured to modulate the release of an API present in the hydrophobic composition such as, but not limited to, an NO releasing API. In some embodiments, when an admixture is formed comprising the hydrophobic composition and the hydrogel, water present in the hydrogel may contact the hydrophobic composition to modulate the release of the API present in the hydrophobic composition, such as, but not limited to, an NO releasing API. Alternatively or in addition, in some embodiments, the hydrogel in an admixture may modulate the pH of the hydrophobic composition in the admixture, thereby modulating the release of an API present in the hydrophobic composition, such as, but not limited to, an NO releasing API. In some embodiments, when a hydrogel of the present invention and/or hydrophobic composition of the present invention are in admixture, the hydrogel may supply water to the hydrophobic composition and/or modulate the pH of the hydrophobic composition. In some embodiments, an admixture of the present invention may increase the solubility of an API (e.g., an NO-releasing API) and/or may increase the bioavailability of an API or an active component of an API (e.g., NO).

"Hydrogel," as used herein, refers to a hydrophilic gel comprising a gel matrix and water. Water may be present in a hydrogel in an amount of about 50% to about 99% by weight of the hydrogel, or any range and/or individual value therein, such as, but not limited to, about 55% to about 95%, about 65% to about 95%, about 70% to about 99%, about 75% to about 95%, about 80% to about 90%, or about 80% to about 85% by weight of the hydrogel.

The hydrogel may comprise means for maintaining and/or stabilizing the pH of an admixture of the present invention. The means for maintaining and/or stabilizing the pH of an admixture may be configured to control the pH of the admixture within a desired pH range. Example means for maintaining and/or stabilizing the pH of an admixture include, but are not limited to, buffers. Examples of buffers that may be used in a hydrogel include, but are not limited to, acetic acid/acetate buffers; hydrochloric acid/citrate buffers; citro-phosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, NaCl, Tween buffered saline (TNT), phosphate buffered saline, Triton X-100 (PBT) and mixtures thereof; cacodylate buffers; barbital buffers; tris buffers; and any combination thereof.

A buffering agent may be present in the hydrogel at a concentration of about 5 mmol to about 3 moles or any range and/or individual value therein, such as, but not limited to about 10 mmol to about 1 mole, about 1.5 moles to about 2.5 moles, about 100 mmol to about 750 mmol, or about 200 mmol to about 500 mmol. In some embodiments, a buffering agent may be present in the hydrogel at a concentration in a range of about 0.5M to about 5M (e.g., about 1, 1.5, 2, 2.5, 3, 3.5, 4, 4.5, or 5M) with the molarity calculated based on the amount of water present in the hydrogel. In some embodiments, a buffering agent may be present in the hydrogel in an amount of about 0.1% to about 20% by weight of the hydrogel, such as, but not limited to, about 0.1% to about 10%, about 1% to about 15%, about 10% to about 20%, about 5% to about 15%, or about 1% to about 5% by weight of the hydrogel. In some embodiments, at least two buffering agents (e.g., 2, 3, 4, or more) may be present in a hydrogel of the present invention.

In some embodiments, the hydrogel may comprise a phosphate buffer. Example phosphate buffers may include at least one phosphate salt such as, but not limited to, sodium phosphate (e.g., sodium dihydrogen phosphate, disodium hydrogen phosphate, trisodium phosphate and sodium aluminum phosphate), potassium phosphate (e.g., potassium phosphate monobasic and potassium phosphate dibasic), rubidium phosphate, caesium phosphate, and ammonium phosphate, and/or at least one phosphoric acid such as, but not limited to, pyrophosphoric acid, triphosphoric acid, and orthophosphoric acid. The hydrogel may have a total phosphate concentration of about 5 mmol to about 1 mole of phosphate, such as, but not limited to, about 10 mmol to about 750 mmol, about 150 mmol to about 500 mmol, or about 200 mmol to about 400 mmol. In certain embodiments, the hydrogel may comprise a phosphate buffer present in an amount of about 1% to about 20% by weight of the hydrogel, such as, but not limited to about 1% to about 15% by weight, about 5% to about 15% by weight, about 10% to about 20%, about 5% to about 10% by weight, about 1% to about 5%, or about 4% to about 8% by weight of the hydrogel.

Additional example buffering agents include, but are not limited to, citric acid, acetic acid, lactic acid, boric acid, succinic acid, malic acid, sodium hydroxide, potassium hydroxide, and any combination thereof. In some embodiments, the hydrogel may comprise an acetate buffer. Example acetate buffers may include acetic acid and/or at least one acetate salt such as, but not limited to, sodium acetate and potassium acetate. In some embodiments, a hydrogel of the present invention may comprise a buffering agent having a pKa in a range of 4 to 6.5, such as, for example, in a range of 4-5 or 5.5-6.5. In some embodiments, the hydrogel may comprise a buffering agent having a pKa of about 4, 4.5, 5, 5.5, 6, or 6.5.

In some embodiments, hydrogel does not comprise or is substantially devoid of a buffer and/or a buffering agent. In some embodiments, the hydrogel is unbuffered (i.e., the pH of the hydrogel is not stabilized with a buffer and/or a buffering agent).

The hydrogel may be pH dependent. In some embodiments, the hydrogel may be configured to have a buffer capacity of at least about 4 to about 8, or any range and/or individual value therein, such as, but not limited to, about 4 to about 7, about 5 to about 6, about 5 to about 8, or about 6 to about 8. The hydrogel may be configured to maintain and/or stabilize the pH of an admixture within about 0.5 or more pH units such as, for example, about 1, 2, or 3 pH units, of the pH of the hydrogel. The pH of the admixture may be maintained and/or stabilized when the admixture is formed and/or at the site of application (e.g., the skin of a subject and/or a wound bed) for the admixture. For example, when an admixture comprising a hydrogel having a pH of about 4 is formed with a hydrophobic composition of the present invention and applied to the skin of a subject, the hydrogel may be configured to maintain and/or stabilize the pH of the admixture within about 0.5 pH units of the hydrogel pH (i.e., the hydrogel may maintain the pH of the admixture in a pH range of about 4.5 to 5.5). In some embodiments, a hydrogel may be configured to maintain and/or stabilize the pH of an admixture in a pH range of about pH 3 to about pH 6, about pH 3 to about pH 5, about pH 3 to about pH 4, about pH 4 to about pH 8, about pH 4 to about pH 7, about pH 4 to about pH 6, about pH 5 to about pH 7, about pH 5 to about pH 6, about pH 6 to about pH 7, or any other range therein. The admixture may thus provide a particular pH to the site of application (e.g., skin), which may increase or decrease the pH of the site of application in the absence of the admixture.

A hydrogel of the present invention may have any suitable pH, such as a pH of about 3 to about 8 or any range and/or individual value therein, such as about 3 to about 4, about 4 to about 5, about 4.5 to about 6.5, or about 4 to about 6. In certain embodiments, the hydrogel may have a pH of about 4 or about 4.5. In some embodiments, the hydrogel may be buffered and/or may not contain a preservative.

A hydrogel may comprise a natural and/or synthetic polymer. Example polymers include, but are not limited to, polysaccharides such as chitosan and chitin; charged celluloses and pharmaceutically acceptable salts thereof; acrylic acids such as polyacrylic polymers such as polyacrylic acid, polyacrylate polymers, cross-linked polyacrylate polymers, cross-linked polyacrylic acids, polyacrylic acid polymers commercially available from Lubrizol of Wickliffe, Ohio under the trademark CARBOPOL®, and mixtures thereof; and any combination thereof. In some embodiments, a hydrogel comprises a charged cellulose or a pharmaceutically acceptable salt thereof. Example charged celluloses or pharmaceutically acceptable salts thereof include, but are not limited to, ionic celluloses, carboxymethyl cellulose and salts thereof, hydroxyethyl carboxymethyl cellulose, hydroxypropyl carboxymethyl cellulose, sulfoethyl cellulose, hydroxyethyl sulfoethyl cellulose, hydroxypropyl sulfoethyl cellulose, hydroxyethyl cellulose ethoxylate, hydroxypropylmethyl cellulose, methyl cellulose, ethyl cellulose, hydroxyethyl cellulose, hydroxyethylmethyl cellulose, carrageenan, chitosan, xanthan gum, sodium alginate, propylene glycol aginate, alginic acid and its salts, and any combination thereof. In some embodiments, a hydrogel may comprise carboxymethyl cellulose and/or a salt thereof. In some embodiments, a hydrogel may comprise hydroxyethyl cellulose ethoxylate, quaternized. In some embodiments, a hydrogel may comprise chitosan.

A polymer, such as, but not limited to, charged cellulose or a pharmaceutically acceptable salt thereof, may be present in a hydrogel in an amount of about 0.1% to about 15% by weight of the hydrogel or any range and/or individual value therein, such as, but not limited to, about 0.3% to about 10%, about 0.5% to about 10%, about 1% to about 10% or about 1% to about 5% by weight of the hydrogel. In certain embodiments, a polymer, such as, but not limited to, charged cellulose and/or a pharmaceutically acceptable salt thereof (e.g., carboxymethyl cellulose and salts thereof), may be present in a hydrogel in an amount of about 0.1%, 0.3%, 0.5%, 1%, 2%, 3%, 4%, 5%, 6%, 7%, 8%, 9%, 10%, 11%, 12%, 13%, 14%, or 15% by weight of the hydrogel or any range and/or individual value therein.

A hydrogel may comprise a polyhydric alcohol. Example polyhydric alcohols include, but are not limited to, glycerol, glycols, propylene glycol, hexylene glycol, polyethylene glycol, polypropylene glycol, triethylene glycol, neopental glycols, triethanolamine, diethanolamine, ethanolamione, butylene glycol, polyethylene glycol, n-methyl diethanolamine, isopropanolamine, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, a hydrogel may comprise glycerol. In some embodiments, a hydrogel may comprise a glycol, such as hexylene glycol.

A polyhydric alcohol may be present in a hydrogel in an amount of about 1% to about 30% by weight of the hydrogel or any range and/or individual value therein, such as, but not limited to, about 1% to about 25%, about 5% to about 15%, about 5% to about 20%, about 10% to about 30%, or about 15% to about 25% by weight of the hydrogel. In certain embodiments, a polyhydric alcohol may be present in a hydrogel in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the hydrogel or any range and/or individual value therein.

A hydrogel may comprise a preservative. A preservative may be present in a hydrogel in an amount of about 0.01% to about 2% by weight of the composition or any range and/or individual value therein, such as, but not limited to, about 0.05% to about 1%, about 0.05% to about 0.5%, or about 0.1% to about 1% by weight of the hydrogel. In certain embodiments, a preservative is present in a hydrogel in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the hydrogel or any range and/or individual value therein. In some embodiments, a hydrogel of the present invention does not comprise a preservative.

Example preservatives that may be present in a hydrogel of the present invention include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A hydrogel may comprise a neutralizing agent. A neutralizing agent may be present in a hydrogel in an amount sufficient to provide the hydrogel with a pH of about 3 to about 8, or any range and/or individual value therein, such as, but not limited to, about 4 to about 7 or about 6 to about 7. In some embodiments, a neutralizing agent adjusts the pH of the hydrogel. In certain embodiments of the present invention, a neutralizing agent may be present in a hydrogel of the present invention in an amount sufficient for the hydrogel to have a pH of about 3, 3.5, 4, 4.5, 5, 5.5, 6, 6.5, 7, 7.5, or 8 or any range and/or individual value therein. Example neutralizing agents that may be present in a hydrogel include, but are not limited to, bases such as sodium hydroxide, potassium hydroxide, and mixtures thereof; acids such as hydrochloric acid, citric acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

In some embodiments, a hydrogel of the present invention comprises water, a polymer, a buffering agent, and a humectant. Water may be present in an amount of about 50% to about 90% by weight of the hydrogel, the polymer may be present in an amount of about 0.5% to about 5% by weight of the hydrogel, the buffering agent may be present in an amount of about 1% to about 20% by weight of the hydrogel, and the humectant may be present in an amount of about 1% to about 20% by weight of the hydrogel. The buffering agent may comprise at least two buffering agents. In some embodiments, the polymer is carboxymethylcellulose or a salt thereof, the buffering agent is an acetate (e.g., sodium acetate) and/or acetic acid, and the humectant is glycerin. In some embodiments, the hydrogel does not comprise a preservative. In some embodiments, the hydrogel comprises a preservative (e.g., benzoic acid) in an amount of about 0.01% to about 1% by weight of the hydrogel.

According to some embodiments, a composition of the present invention (e.g., hydrogel and/or admixture) may be antimicrobial. A hydrogel and/or admixture of the present invention may be cosmetically elegant. "Cosmetically elegant" as used herein, refers to a composition that is attractive for application to the skin, which may include mucosa. In some embodiments, a composition of the present invention may be cosmetically elegant for the skin and/or mucosa. A cosmetically elegant composition of the present invention may have one or more of the following properties: suitable consistency or viscosity for topical application (e.g., easy to spread onto the skin and does not run), suitable texture for topical application (e.g., a smooth or soft composition that is not gritty), ability to absorb and/or permeate the skin, non-sticky or not tacky, does not leave a residue, leaves the skin feeling good, and after application does not leave the skin oily or dry.

In some embodiments, a hydrogel may have a viscosity of about 5,000 cP (centipoise) to about 100,000 cP, or any range and/or individual value therein, such as, but not limited to, about 10,000 cP to about 50,000 cP, about 20,000 cP to about 40,000 cP, about 30,000 cP to about 50,000 cP, about 50,000 cP to about 100,000 cP, or about 30,000 cP to about 75,000 cP.

A hydrogel, of the present invention may be suitable in an admixture of the present invention with one or more, such as, but not limited to, 2, 3, 4, or more, different compositions. A hydrogel, of the present invention may be used as a drug delivery system and/or a drug release system when in an admixture of the present invention. For example, a hydrogel may be configured to modulate the release of an active pharmaceutical ingredient (API) in a hydrophobic composition when an admixture comprising the hydrogel and hydrophobic composition is formed and/or administered. Alternatively or in addition, a hydrogel may be configured to modulate the pH of a hydrophobic composition when an admixture comprising the hydrogel and hydrophobic composition is formed and/or administered. In some embodiments, a hydrogel may be configured to modulate the pH of a hydrophobic composition comprising a nitric oxide (NO) releasing API and/or the rate of NO release from a NO releasing API when an admixture comprising the hydrogel and hydrophobic composition is formed and/or administered.

In some embodiments, an admixture of the present invention may be self-emulsifying. A self-emulsifying admixture may form a spontaneous emulsion (e.g., with the application of minimal or no mechanical energy) upon combining the at least two compositions of the admixture. In some embodiments, the self-emulsifying admixture may not require and/or need heat in order to form a spontaneous emulsion. In some embodiments, a self-emulsifying admixture may emulsify spontaneously via a chemical reaction under minimal or no mechanical and/or external force to form a spontaneous emulsion. For example, the self-emulsifying admixture may be formed by a subject and/or third party by mixing the at least two compositions of the admixture with their hands. In some embodiments, the minimal mechanical force may provide sufficient shear to emulsify the at least two compositions of the admixture. In some embodiments, the minimal mechanical force to emulsify the at least two compositions of the admixture may have a shear rate in a range of about $1$ $s^{-1}$ to about $5,000$ $s^{-1}$, such as, for example, about $10$ $s^{-1}$ to about $200$ $s^{-1}$, about $100$ $s^{-1}$ to about $1000$ $s^{-1}$, about $500$ $s^{-1}$ to about $3000$ $s^{-1}$, or about $10$ $s^{-1}$ to about $2500$ $s^{-1}$.

The self-emulsifying admixture upon forming an emulsion may contain and/or be a single phase. In some embodiments, the self-emulsifying admixture may be a coarse emulsion, a microemulsion or a nanoemulsion. In some embodiments, the self-emulsifying admixture may be a non-separating or continuous emulsion and/or a homogeneous composition. In some embodiments, a self-emulsifying admixture may encapsulate a hydrophobic component in a hydrophilic component. In some embodiments, a self-emulsifying admixture may contain droplets of an oil or a hydrophobic phase with water or a hydrophilic phase surrounding the droplets, and the droplets may encapsulate an API. A self-emulsifying admixture of the present invention may be a water-in-oil emulsion or an oil-in-water emulsion. In some embodiments, a self-emulsifying admixture may be formed upon combining a hydrophobic composition and a hydrophilic composition (e.g., a hydrogel) of the present invention. In some embodiments, the hydrophobic composition may be determinative as to whether the composition is a self-emulsifying composition.

In some embodiments, the admixture is a continuous emulsion (i.e., a non-separating emulsion). In some embodiments, the admixture may remain as a continuous emulsion and/or may stay together as a single phase for at least 1, 2, 3, 4, 5, 6, or more days, or 1, 2, 3, 4, 5, 6, or more weeks, or 1, 2, 3, 4, 5, 6, or more months. In some embodiments, the admixture may be a continuous emulsion for a period of time sufficient to apply the composition to a subject. A composition that separates out into two or more phases within 1 day of combination of two or more parts of the composition is not considered to be a self-emulsifying admixture and/or a continuous emulsion.

In some embodiments, a self-emulsifying admixture may have a droplet size (e.g., diameter) of greater than 100 µm. In some embodiments, the self-emulsifying admixture may form or produce an emulsion that may have a droplet size of about 100 µm or less, such as, but not limited to, about 90 µm, 70 µm, 50 µm, 30 µm or less, or any range and/or individual value therein. In some embodiments, the self-emulsifying admixture may form or produce an emulsion that may have a droplet size of greater than 1 µm. In some embodiments self-emulsifying admixture may form or produce a nanoemulsion that may have a droplet size of about 400 nm or less, such as, but not limited to, about 300 nm, 200 nm, 100 nm, 50 nm or less, or any range and/or individual value therein. In some embodiments, a self-emulsifying admixture may comprise droplets that are substantially uniform in size.

An admixture of the present invention may provide a particular release pattern for an API present in the admixture. The API release pattern may be determined by comparing the amount or concentration of API released over a period of time and/or the rate of release of an API from the admixture over a period of time. In some embodiments, the at least two different compositions present in the admixture are selected to provide a particular API release pattern. The API release pattern may be desirable for a particular inflammatory condition. In some embodiments, the admixture may be configured to provide a particular release pattern of an API present in the admixture.

An admixture of the present invention may provide for immediate release of the API from the admixture and/or sustained release of the API from the admixture. As used herein, immediate release refers to the release of 50% or more of the API within 4 hours of mixing and sustained release refers to the release of less than 50% of the API within 4 hours of mixing. In some embodiments, an admixture of the present invention may increase the amount of API released and/or the potency of an API present in at least one composition in the admixture by maintaining the pH of the admixture in a particular pH range compared to the release and/or potency of the API in the composition in the absence of the admixture.

The API present in the admixture may be released substantially continuously from the admixture over a period of time. "Substantially continuously," and grammatical variants thereof as used herein refer to a release of an API from the admixture for all or part of the time such that on average the release of the API confers an overall beneficial effect on the subject. Thus, there may be one or more short, intermittent and/or regular time periods in which the API is not being released, but the overall beneficial effect of the API on the subject remains. In some embodiments, the admixture may provide an API release pattern that is substantially continuous over a period of time and provide a therapeutically effective amount of the API over the period of time. In some embodiments, the amount of API released and/or the API release rate may vary over a period of time. In certain embodiments, the admixture may comprise two or more (e.g., 2, 3, 4, 5 or more) release rates for the API.

The admixture may provide an API release pattern that is substantially constant over a period of time. "Substantially constant" as used herein refers to a measurable value, such as the amount of API or the API release rate, on average, varying less than about 20%, 15%, 10%, 5%, 1% or less over a period of time. In some embodiments, the API release rate may be substantially constant for a period of time and vary over another consecutive or nonconsecutive period of time and vice versa.

In some embodiments, the admixture may provide an API release pattern having a rapid release portion and a substantially constant release portion. The rapid release portion may comprise the amount of API released from administration (i.e., t=0) to 2 hours after administration or any range therein, such as, but not limited to, 0 to 1 hour or 0 to 30 minutes after administration. The substantially constant release portion may comprise the amount of API released from immediately after the rapid release portion to the final amount of API is released. An API may be released from an admixture of the present invention for any period of time. In some embodiments, an API may be released from the admixture for at least about 4 hours, 6 hours, 12 hours, 24 hours, 2 days, 3, days, 4 days, 5, days, 6 days, 7 days, or more, or any range and/or individual value therein. The API released from the admixture may be released in an amount that overall provides a beneficial effect on the subject and/or provides a therapeutically effective amount of the API over the period of time.

In some embodiments, a greater amount or concentration of the API may be released during the rapid release portion compared to the substantially constant release portion or vice versa. In some embodiments, the amount of API released from the admixture during the rapid release portion may be about 10%, 20%, 30%, 40%, 50%, 60%, 70%, 80%, 90%, 100%, 150%, 200%, 300%, 400%, 500%, or more, or any range and/or individual value therein, than the amount of API released during the substantially constant release portion. In other embodiments, the amount of API released from the admixture during the substantially constant release portion may be about 10%, 20%, 30%, 40%, 50%, 60%, 70%, 80%, 90%, 100%, 150%, 200%, 300%, 400%, 500%, or more, or any range and/or individual value therein, than the amount of API released during the rapid release portion.

An admixture of the present invention may be suitable for topical administration. The admixture may comprise a single phase even though it may be prepared or formed from two or more different compositions. The admixture may be buffered. In some embodiments, the admixture may comprise a hydrophobic composition and a hydrogel as described herein. In some embodiments, an admixture may comprise a hydrogel and an ointment. The hydrogel and ointment may form an admixture having a single phase that is buffered. In some embodiments, the admixture comprises a hydrogel and an ointment, and the admixture may be in the form of a cream. In some embodiments, the admixture may be a self-emulsifying admixture and may comprise a hydrogel and an ointment.

An admixture of the present invention may have a pH in a range of about 4 to about 9. In some embodiments, the admixture may have a pH of about 4, 4.5, 5, 5.5, 6, 6.5, 7, 7.5, 8, 8.5, or 9. In some embodiments, the admixture may be configured to have a pH in a range of about pH 4 to about pH 8, about pH 4 to about pH 7, about pH 4 to about pH 6, about pH 4 to about pH 5, about pH 5 to about pH 7, about pH 5 to about pH 6, about pH 6 to about pH 7, or about pH 5 to about pH 8, or any other range therein.

In some embodiments, the hydrogel, the hydrophobic composition, and/or the admixture may be sterilized. Some embodiments include that the hydrogel is sterilized and does not comprise a preservative.

In some embodiments, an admixture of the present invention may release at least about 100 nmol of NO/mg of the admixture at 24, 23, 22, 21, 20, 19, 18, 17, 16, 15, 14, 13, 12, 11, 10, 9, 8, 7, 6, 5, 4, 3, 2, or 1 hour(s), or 45, 30, 15, 5, 4, 3, 2, or 1 minute(s) after administration and/or combination (e.g., where a nitric oxide-releasing pharmaceutical composition comprises at least two compositions that are admixed together, such as a hydrophobic composition and hydrogel as described herein) as measured by in vitro release. In some embodiments, the admixture may release, on average, about 100, 120, 140, 160, 180, 200, 220, 240, 260, 280, 300, 320, 340, 360, 380, 400, 420, 440, 460, 480, 500 or more nmol of NO/mg of the admixture at 24, 23, 22, 21, 20, 19, 18, 17, 16, 15, 14, 13, 12, 11, 10, 9, 8, 7, 6, 5, 4, 3, 2, or 1 hour(s), or 45, 30, 15, 5, 4, 3, 2, or 1 minute(s) after administration and/or combination as measured by in vitro release. The amount of nitric oxide (NO) released from the admixture may be determined using real time in vitro release testing. In some embodiments, nitric oxide release may be determined using a chemiluminescent nitric oxide analyzer. The amount of NO released may be determined after the admixture is formed (e.g., after a hydrophobic composition and hydrogel as described herein are combined), such as, for example, immediately upon combination/contact or 1, 2, 4, 6, 8, 10, 12, 14, 16, 18, or 20 minutes after the admixture is formed. As described above, when a composition (e.g., an admixture) is measured in vitro, formation of the composition (e.g., combination of two or more compositions to form an admixture) may be used as equivalent or comparative in time to administration of the composition to a subject.

In some embodiments, an admixture of the present invention may provide for a maximum concentration (Cmax) of NO release of at least about 1200 pmol of NO/mg of the admixture at about 1 to about 20 minutes after the admixture is administered and/or formed (e.g., about 1, 2, 4, 6, 8, 10, 12, 14, 16, 18, or 20 minutes after the admixture is administered and/or formed) as measured by in vitro release. In some embodiments, the Cmax and Tmax may be determined based on an instantaneous NO release or total NO release determined over 24, 12, 6, 2, or 1 hour(s) or 45, 30, 15, or 10 minutes. In some embodiments, the admixture may provide a Cmax of NO release of about 1200, 1400, 1600, 1800, 2000, 2200, 2400, 2600, 2800, 3000, 3200, 3400, 3600, 3800, 4000, 4200, 4400, 4600, 4800, 5000 pmol of NO/mg or more at about 1, 2, 3, 4, 5, 6, 7, 8, 9, 10, 11, 12, 13, 14, 15, 16, 17, 18, 19 or 20 minutes after the admixture is administered and/or formed. In some embodiments, an admixture of the present invention may provide a maximum concentration of NO released in a range of about 1300 pmol of NO/mg to about 2000 pmol of NO/mg or about 2000 pmol of NO/mg to about 4000 pmol of NO/mg. In some embodiments, an admixture of the present invention may provide a maximum concentration of NO released at about 1 to about 5 minutes after the admixture is administered and/or formed.

In some embodiments, a packaged composition of the present invention may have a stability of at least 1 year (e.g., 1, 2, 3, or 4 years or more) at 5° C., optionally with intermittent temperatures up to 25° C. In some embodiments, a packaged composition of the present invention may have a stability of at least 2 years at 5° C., optionally with intermittent temperatures up to 25° C. In some embodiments, stability may be determined and/or defined by the composition comprising at least 90% of the NO-releasing compound or at least 90% of the initial amount of nitric oxide that the composition may release when packaged, such as, e.g., at least 91%, 92%, 93%, 94%, 95%, 96%, 97%, 98%, 99%, or more. In some embodiments, a packaged composition of the present invention may have a stability of at least 1 or 2 years at 5° C., optionally with intermittent temperatures up to 25° C., with the composition comprising at least 90% or 95% of the NO-releasing compound. In some embodiments, a packaged composition of the present invention may have a stability of at least 1 or 2 years at 5° C., optionally with intermittent temperatures up to 25° C., with the composition able to and/or maintaining the ability to release at least 90% or 95% of the initial amount of nitric oxide that the composition may release when packaged.

In some embodiments, a packaged composition of the present invention may be safe and/or effective upon opening for at least 30 days, such as, e.g., at least 35, 40, 45, 50, 55, 60, 65, 70, 75, 80, 85, 90, 95, or 100 days or more. Thus, 30 days or more (e.g., 60 or 90 days) after opening the packaged composition, the composition may be able to release a therapeutically effective amount of nitric oxide and/or be safe (e.g., no detrimental side effects). As one skilled in the art will recognize, the rate of release of nitric oxide in a composition under packaged and/or stored conditions may be different (i.e., faster or slower) than the rate of release of nitric oxide when the package is open and/or when the composition is in use. In some embodiments, the rate of release of nitric oxide may be faster when a composition is in use and/or open compared to the rate of release of nitric oxide when the composition was packaged and/or stored.

As discussed above, provided according to some embodiments of the present invention are methods of treating an inflammatory condition of the skin, mucosa, and/or eye in a subject, such as, but not limited to, by decreasing inflammation in the skin, mucosa, and/or eye of the subject by applying a nitric-oxide releasing pharmaceutical composition as described herein. Treatment and/or decrease of inflammation may be detected by a visual reduction in the amount or severity of the inflammation and/or by a decrease in discomfort associated with the inflammation, as identified by the subject.

Any portion of a subject's skin may be treated. "Skin," as used herein, refers to any layer(s) of the skin in which an inflammatory condition and/or inflammation may occur, extend to and/or reside, including that on limbs, trunk, head, etc. Thus, the word "skin" is intended to include, but not be limited to, the epidermal and/or dermal layers, and may also include the underlying subcutaneous tissue. Mucosa (e.g., mouth, nasal, vaginal, etc.) and/or a surface of a subject's eye may also be treated. However, in some embodiments of the present invention, one or more of the subject's appendages are treated by a method described herein. In some embodiments, the subject's face and/or scalp is treated. Furthermore, in some embodiments, the subject's trunk is treated by a method described herein. In some embodiments, a method of the present invention locally delivers and/or administers (e.g., topically locally delivers and/or administers) nitric oxide to a site of inflammation for a subject. Additionally, in some embodiments, a nitric oxide-releasing pharmaceutical composition according to embodiments of the present invention may be applied in another manner, such as, but not limited to, systemic application.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent or adult.

Illustrative avians according to the present invention include chickens, ducks, turkeys, geese, quail, pheasant, ratites (e.g., ostrich) and domesticated birds (e.g., parrots and *canaries*), and birds in ovo.

The methods of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" the methods of the present invention, e.g., the subject has been diagnosed with a disease or disorder associated with inflammation, the subject is at risk for a disease or disorder associated with inflammation, or it is believed that the subject has a disease or disorder associated with inflammation. In some embodiments of the present invention, the subject has been diagnosed with a disease or disorder associated with inflammation. In certain embodiments of the present invention, the subject has been diagnosed with a skin disease or disorder associated with inflammation.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom (e.g., a bacterial infection, such as a *Staphylococcus aureus* infection) is achieved and/or there is a delay in the progression of the disease or disorder. In particular embodiments of the present invention, the severity of the inflammation is reduced in a subject compared to the severity of the inflammation in the absence of the methods of the present invention.

In some embodiments, a composition of the present invention is administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount of a composition of the present invention may be administered and may include administering a treatment effective amount of a nitric oxide-releasing active pharmaceutical ingredient. In some embodiments, a treatment effective amount of nitric oxide may be administered and/or applied in a method of the present invention. In some embodiments, a method of the present invention is carried out in a manner such that the administration of a composition comprising a nitric oxide-releasing active pharmaceutical ingredient does not produce systemic effects from the administration of nitric oxide, such as, for example, in a treatment effective amount.

The terms "prevent," "preventing" and "prevention" (and grammatical variations thereof) refer to avoidance, reduction and/or delay of the onset of inflammation and/or a clinical symptom associated therewith in a subject and/or a reduction in the severity of the onset of the inflammation and/or clinical symptom relative to what would occur in the absence of a method of the present invention. The prevention can be complete, e.g., the total absence of inflammation and/or clinical symptom in the subject. The prevention can also be partial, such that the occurrence of inflammation and/or clinical symptom in the subject and/or the severity of onset is less than what would occur in the absence of a method of the present invention. In certain embodiments, a method of the present invention prevents inflammation in a subject, such as inflammation that affects the skin of the subject.

In some embodiments, a composition of the present invention is administered in a prevention effective amount. A "prevention effective" amount as used herein is an amount that is sufficient to prevent (as defined herein) inflammation and/or clinical symptom in a subject. Those skilled in the art will appreciate that the level of prevention need not be complete, as long as some benefit is provided to the subject. In some embodiments, a prevention effective amount of a composition of the present invention may be administered and may include administering a prevention effective amount of a nitric oxide-releasing active pharmaceutical ingredient. In some embodiments, a prevention effective amount of nitric oxide may be administered and/or applied in a method of the present invention. In some embodiments, a method of the present invention is carried out in a manner such that the administration of a composition comprising a nitric oxide-releasing active pharmaceutical ingredient does not produce systemic effects from the administration of nitric oxide, such as, for example, in a prevention effective amount.

A composition of the present invention may be topically applied to a subject using any method known to those of skill in the art. In some embodiments, the composition may be topically applied to the subject at least 1, 2, 3, or more times per day. In some embodiments, the composition may be topically applied to the subject at least 1, 2, 3, 4, 5, 6, 7, 8, or more times per week and/or month. In certain embodiments, the composition may be topically applied to the subject once daily, twice daily, every other day, every third day, once per week, or twice per week. In some embodiments, the composition may be applied to a subject at least once daily for an extended period of time (e.g., a week, month, 2 months, etc.) and/or until inflammation and/or clinical symptom associated therewith has been treated and/or prevented in the subject. In some embodiments, the composition may be applied on an as needed basis.

In some embodiments, a subject may see a decrease and/or reduction in inflammation and/or at least one clinical symptom associated with therewith within about 1, 2, 3, 4, 5, 6, 7, 8, 9, 10, 11, 12, 13, or more day(s) and/or week(s). In some embodiments, a composition and/or method of the present invention may treat inflammation and/or a clinical symptom associated therewith for a given period of time (e.g., 1, 2, 3, 4, 5, or 6 day(s), or 1, 2, 3, 4, or more weeks, or 1, 2, 3, 4, 5, 6, or more months, etc.).

In some embodiments, methods of decreasing inflammation may include using a method described herein in combination with another therapeutic regimen and/or in combination with other medicaments, such as those that have antimicrobial, anti-inflammatory, pain-relieving, immunosuppressant, vasodilating properties, and/or anti-acne properties. For example, other anti-acne agents such as retinoids, may be used in conjunction (prior, concurrently or after) with the application of the gaseous nitric oxide and/or at least one nitric oxide source. As such, in some embodiments of the present invention, a patient may be treated with a pharmaceutical composition described herein in combination with an additional therapeutic agent when the additional therapeutic agent is not in the same composition. For example, in some embodiments, an additional therapeutic agent may be administered (e.g., topically, systemically, parenterally, orally, buccally, subcutaneously, via inhalation, intratracheally, surgically, transdermally, etc.), either concurrently and/or sequentially with a pharmaceutical composition described herein.

In some embodiments, a pharmaceutically acceptable composition may be administered to the skin via spray delivery. A non-aqueous delivery propellant may be used for water sensitive NO-releasing compounds such as diazeniumdiolate-modified compounds. Further, in some embodiments, particular components of the medicaments may be separated at some point prior to application of the medicament. For example, a water reactive NO-releasing compound may be stored separately (e.g., in a dual chamber pump) from an aqueous component or propellant until application (e.g., via spraying or applying a gel). In some embodiments of the present invention, the NO-releasing compounds may be combined with an aqueous constituent prior to application or the NO-releasing compounds and an aqueous constituent may be applied to the skin sequentially.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention will be further illustrated by the following non-limiting examples.

EXAMPLES

Example 1

A nitric oxide releasing macromolecular compound (Nitricil™ NVN1) comprising MAP3 was fabricated as described in United States Patent Application Publication No. 2009/0214618 and in PCT Patent Application Number PCT/US12/22048, filed Jan. 20, 2012, entitled "Temperature Controlled Sol-Gel Co-Condensation," the disclosures of which are incorporated herein by reference as if set forth in their entirety. The resulting macromolecular particles were ball milled to provide an average particle size of from 8 to 10 μm to provide an active pharmaceutical ingredient (API).

FIG. 1 is a graph of the release profiles for Nitricil™ NVN1 and NVN4 at pH 7.4 and 37° C. for the first 200 minutes of release. Nitricil™ NVN4 is a nitric oxide releasing macromolecular compound comprising AEP3/TEOS in a 1:1 ratio, and was fabricated as described in United States Patent Application Publication No. 2009/0214618 and in PCT Patent Application Number PCT/US12/22048, filed Jan. 20, 2012, entitled "Temperature Controlled Sol-Gel Co-Condensation" to provide an API. The overall release kinetics of Nitricil™ NVN1 are provided in Table 1 below.

TABLE 1

| Half Life and Potency of Nitricil ™ NVN1 at pH 7.4 and 37° C. | | |
| --- | --- | --- |
| Compound | Half Life | Potency |
| Nitricil ™ NVN1 | 2.3 minutes | 4.9 μmol/mg |

Nitricil™ NVN1 was formulated into two finished dosage forms of an ointment as set forth in Table 2.

TABLE 2

| Nitricil ™ NVN1 ointment formulations. | | |
| --- | --- | --- |
| Component | 0.2% NVN1 | 2% NVN1 |
| Mineral Oil, USP | 74.8 | 73.0 |
| Captex 300 | 10.0 | 10.0 |
| Miglyol 840 | 10.0 | 10.0 |
| Cab-o-sil M5P | 5.0 | 5.0 |
| Nitricil ™ NVN1 | 0.2 | 2.0 |
| Total | 100.0 | 100.0 |

The placebo ointment was formulated with the weight of the API being replaced by increasing the amount of mineral oil.

Example 2

BALB/c derived male mice, weighing 22±2 g, were provided by BioLasco Taiwan (under Charles River Laboratories Technology Licensee). The animals were housed in Individually Ventilated Cages Racks (IVC Racks, 36 Mini Isolator systems) under clean area throughout the experiment. Every 5 mice were kept in an animal cage (in cm, 26.7 length×20.7 width×14.0 height) sterilized with autoclave and maintained under controlled temperature (20-24° C.) and humidity (50%-80%) with 12-hour light/dark cycles. The animals were given free access to sterilized standard lab chow [MF-18 (Oriental Yeast Co., Ltd. Japan)] and sterile tap water ad libitum. All aspects of this work, i.e., housing, experimentation and disposal of animals, w performed in general accordance with the Guide for the Care and Use of Laboratory Animals (National Academy Press, Washington, D.C., 2010).

Groups of 5 BALB/c male mice weighing 22±2 g were used. The animals were sensitized by application of oxazolone (100 µL, 1.5% in acetone) to their preshaved abdominal surface. Seven days later, test substances (20 mg/ear) and vehicle (20 µL/ear) were applied topically to the anterior and posterior surfaces of the right ear 30 min before and 15 min after oxazolone (1%, 20 µL/ear) challenge. Ear swelling was measured with a Dyer model micrometer gauge at 24 hours after oxazolone challenge as an index of inflammation. Ear edema was calculated by subtracting the thickness of the left ear (normal control) from the right ear (treated ear). Percent inhibition was calculated according to the formula: (Ic −It)/Ic×100, where Ic and It refers to increase of ear thickness (mm) in control and treated mice, respectively. One-way ANOVA and Dunnett's test were used to determine statistical significance between vehicle control and treated groups. Significance is set at $P<0.05$.

Test articles (0.2% and 2% Nitricil™ NVN1 Ointment) described in Example 1 were evaluated for possible anti-inflammatory activity in the oxazolone-induced ear swelling assay in BALB/c mice, a model of allergic contact dermatitis. Test substances and vehicles were each administered topically (TOP) at 30 minutes before and 15 minutes after challenge with the second application of oxazolone. Effects of the test substances on ear swelling were measured 24 hours later and the results are summarized in Table 3 below.

TABLE 3

In vivo anti-inflammatory efficacy of NO-releasing compositions

| | | | Ear Swelling | |
| --- | --- | --- | --- | --- |
| Treatment | Route | Dose | % Inhibition (vs. Vehicle A) | % Inhibition |
| Vehicle A (acetone/ethanol: 1/1) | TOP | 20 µL/ear × 2 | — | — |
| Dexamethasone | TOP | 0.3 mg/ear × 2 | 85* | — |
| Placebo Ointment | TOP | 20 mg/ear × 2 | −17 | (vs. Placebo Ointment) |
| 2% Nitricil ™ NVN1 Ointment | TOP | 20 mg/ear × 2 | −4 | 11 |
| 0.2% Nitricil ™ NVN1 Ointment | TOP | 20 mg/ear × 2 | −11 | 5 |

Note:
Negative values indicate no inhibition or stimulation. One-way ANOVA and Dunnett's test were used to ascertain difference between vehicle control (or respective placebo control) and treated groups.
*$P < 0.05$, vs. Vehicle A or respective placebo control.

Topical administration of 0.2% and 2% Nitricil™ NVN1 Ointment were not associated with significant inhibition vs. the vehicle control A (acetone/ethanol: 1/1) and placebo ointment. Placebo ointment treatment did not exhibit a significant effect on oxazolone-induced ear swelling. Dexamethasone (0.1 mg/ear×2), the positive control, was associated with significant inhibition of the oxazolone-induced ear swelling.

Example 3

Using a cold process, ointment formulations were prepared as set forth in Table 4. These formulations were selected for scale-up.

TABLE 4

Nitricil ™ NVN1 Ointment Formulations (TO-007 and TO-008).

| | % w/w | | | | | | | | | | |
| --- | --- | --- | --- | --- | --- | --- | --- | --- | --- | --- | --- |
| Component | TO-007 | | | | | | | | TO-008 | | |
| CrodabaseSQ | 61.4 | 61.3 | 61.0 | 61.0 | 60.0 | 58.0 | 52.0 | 45.0 | 60.0 | 60.0 | 60.0 |
| Miglyol 812 | 12.0 | 12.0 | 12.0 | 12.0 | 12.0 | 12.0 | 12.0 | 12.0 | 12.0 | 12.0 | 12.0 |
| Hexylene glycol | 8.0 | 8.0 | 8.0 | 8.0 | 8.0 | 8.0 | 8.0 | 8.0 | 8.0 | 8.0 | 8.0 |
| Light Mineral Oil | 8.5 | 8.5 | 8.5 | 8.0 | 8.0 | 6.0 | 6.0 | 5.0 | 15.0 | 13.0 | 11.0 |
| Softigen 767 | 10.0 | 10.0 | 10.0 | 10.0 | 10.0 | 10.0 | 10.0 | 10.0 | 5.0 | 5.0 | 5.0 |
| Nitricil ™ NVN1 | 0.1 | 0.2 | 0.5 | 1.0 | 2.0 | 6.0 | 12.0 | 20.0 | 2.0 | 4.0 | 8.0 |

The lab-scale process used during development of the formulations provided in Table 4 was scaled-up to the 5.5-kg scale using a Ross Dual Shaft Mixer, Model No.: CDA-2 with an 8-L mixing vessel. The agitation and homogenization system contained two independently driven top-entering agitators, as described below:

1. A Three-Wing Anchor Agitator driven at a speed range of approximately 23-225 rpm. The anchor is designed with a triangular cross section and includes fixed Teflon scrapers for wiping the sidewall and bottom of mix can.

2. A High-Speed Disperser, 2" diameter blade, driven at a speed range of approximately 1,000-10,000 rpm.

Figure 2:
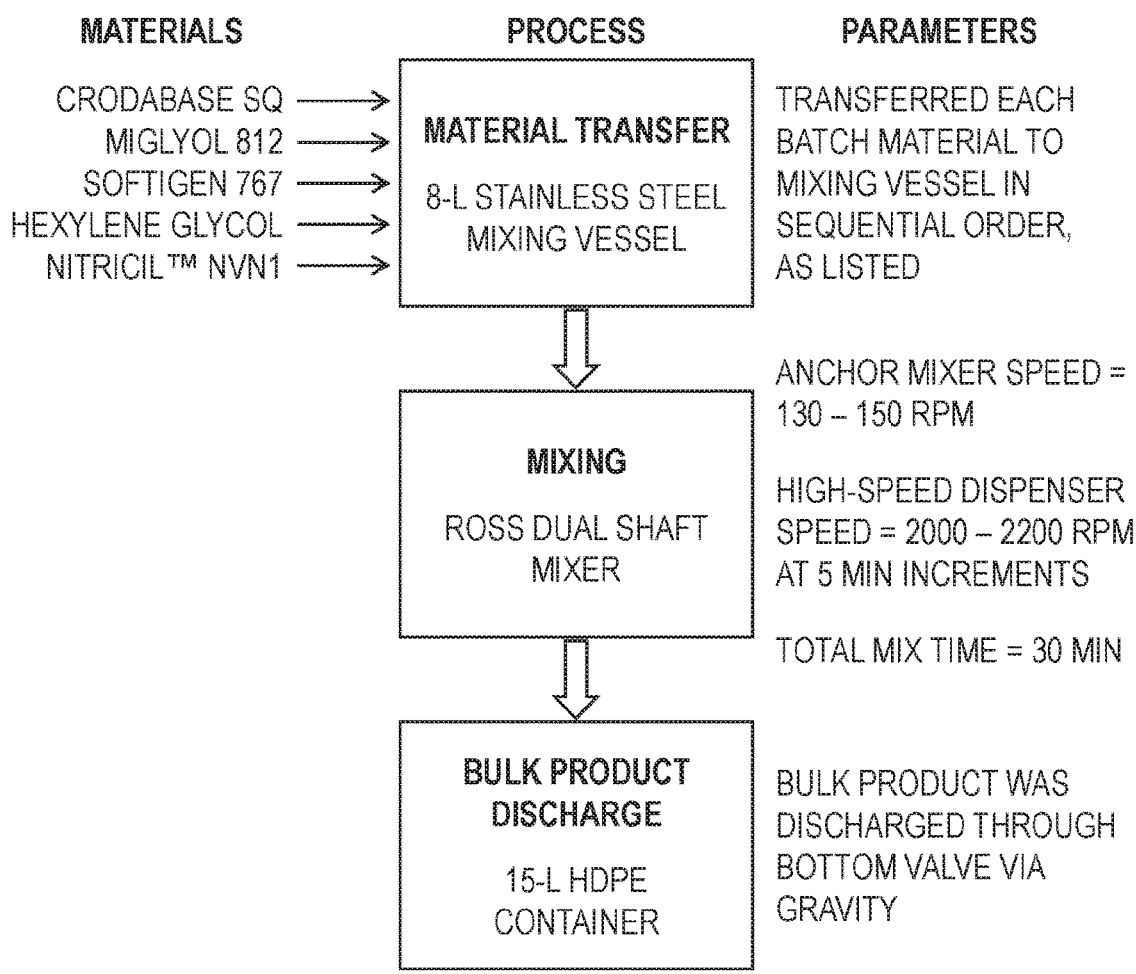
FIG. 2 shows a process flow diagram for the 5.5-kg scale manufacture of an ointment according to some embodiments of the present invention.

Four batches of ointment were manufactured to determine the order of material addition, as well as suitable mixing speeds (anchor agitator and high-speed disperser), and mixing times for the small-scale process. A summary of the development batch formulations is provided in Table 5 and the process flow diagram for the manufacture is provided in FIG. 2.

TABLE 5

Batch formulas for topical ointments.

| Component | Batch 1 Placebo Ointment % w/w | Batch 1 Placebo Ointment Batch Wt. (g) | Batch 2 2% Ointment % w/w | Batch 2 2% Ointment Batch Wt. (g) | Batch 3 2% Ointment % w/w | Batch 3 2% Ointment Batch Wt. (g) | Batch 3 20% Ointment % w/w | Batch 3 20% Ointment Batch Wt. (g) |
|---|---|---|---|---|---|---|---|---|
| Crodabase SQ Croda, Lot# 0000630349 | 60.0 | 1800.0 | 60.0 | 1800.0 | 60.0 | 1800.0 | 52.0 | 1690.0 |
| Light Mineral Oil, NF Spectrum, Lot# ZI0511 | 15.0 | 450.0 | 13.0 | 390.0 | 13.0 | 390.0 | 3.0 | 650.0 |
| Miglyol 812 Sasol, Lot# 110807 | 12.0 | 360.0 | 12.0 | 360.0 | 12.0 | 360.0 | 12.0 | 390.0 |
| Hexylene glycol, NF Hanemann, Lot# ME08T304 | 8.0 | 240.0 | 8.0 | 240.0 | 8.0 | 240.0 | 8.0 | 260.0 |
| Solligen 767 Sasol, Lot# 106445 | 5.0 | 150.0 | 5.0 | 150.0 | 5.0 | 150.0 | 5.0 | 162.5 |
| Nitricil™ NVN1 Novan, Batch# 11-23-17M | | | 2.0 | 60.0 | 2.0 | 60.0 | 20.0 | 97.5 |
| Total | 100.0 | 3000.0 | 100.0 | 3000.0 | 100.0 | 3000.0 | 100.0 | 3250.0 |

The analytical results of the batches are provided in Tables 6 and 7.

TABLE 6

Analytical results for placebo ointment.

| Test | Proposed Specification | Method Reference | Result |
|---|---|---|---|
| Appearance | Colorless to Off-white, Translucent to Opaque Ointment | METH-014 | White, opaque gel |
| Absence of NVN1 by HPLC | NVN1 is absent from the sample chromatogram | METH-058 | Conforms |
| Moisture Content | Report Value, % w/w | METH-003 | 0.2 |
| Apparent pH | Report Value | METH-006 | 6.4 |

TABLE 7

Analytical results for the 2%, 6%, 12%, and 20% Nitricil ™ NVN1 Ointments.

| Test | Proposed Specification | Method Reference | Result | | | |
|---|---|---|---|---|---|---|
| | | | 2% (1203301-15) | 6% (1203901-15) | 12% (1203401-15) | 20% (1203501-15) |
| Appearance | White to Off-white Opaque Ointment | METH-014 | Off-white, Opaque Ointment | Off-white, Opaque Ointment | Off-white, Opaque Ointment | Off-white, Opaque Ointment |
| NVN1 ID (NOA) | Conforms to presence of NVN1000 by presence of nitric oxide | METH-020 | Conforms | Conforms | Conforms | Conforms |
| NVN1 ID (HPLC) | Conforms to presence of NVN1000 by retention time comparison | METH-058 | Conforms | Conforms | Conforms | Conforms |
| NO Content (NOA) | 2% . . . 0.27-0.33% NO 6% . . . 0.77-1.04% NO 12% . . . 1.62-1.98% NO 20% . . . 2.70-3.30% NO | METH-020 | 0.29% | 0.80% | 1.68% | 3.11% |
| NVN1 Assay (HPLC) | 80.0-120.0% LC | METH-058 | 89.3% | 92.8% | 104.5% | 105.2% |
| Moisture Content | Report Result, % w/w | METH-036 | 0.3% | 0.4% | 0.7% | 0.9% |
| Apparent pH | Report Value | METH-039 | 11.4 | 11.7 | 11.7 | 11.7 |

Example 4

A Nitricil™ ointment was evaluated in BALB/c mice to determine the potential anti-inflammatory properties of the Nitricil™ ointment in vivo. BALB/c derived male mice, weighing 22±2 g, were provided by BioLasco Taiwan (under Charles River Laboratories Technology Licensee). The animals were housed in Individually Ventilated Cages Racks (IVC Racks, 36 Mini Isolator systems) under clean area throughout the experiment. Every 5 mice were kept in an animal cage (in cm, 26.7 length×20.7 width×14.0 height) sterilized with autoclave and maintained under controlled temperature (20-24° C.) and humidity (50%-80%) with 12-hour light/dark cycles. The animals were given free access to sterilized standard lab chow [MF-18 (Oriental Yeast Co., Ltd. Japan)] and sterile tap water ad libitum. All aspects of this work, i.e., housing, experimentation and disposal of animals, were performed in general accordance with the Guide for the Care and Use of Laboratory Animals (National Academy Press, Washington, D.C., 2011).

Nitricil™ topical ointment (1% and 4%) and placebo ointment were tested in this study. The composition of the Nitricil™ topical ointment formulations and placebo ointment are provided in Table 8. Dexamethasone (0.1 mg/ear) was used as a positive control. Dexamethasone is a potent glucocorticoid steroid that is used to treat various inflammatory and autoimmune disorders.

TABLE 8

Composition of ointment formulations used in this study.

| | % w/w | | |
|---|---|---|---|
| Component | Placebo | 1% | 4% |
| Mineral Oil and Polyethylene Crodabase SQ, Croda | 61.0 | 55.5 | 54.0 |
| Medium Chain Triglycerides, NF Miglyol 812, Sasol | 12.0 | 12.0 | 12.0 |

TABLE 8-continued

Composition of ointment formulations used in this study.

| | % w/w | | |
|---|---|---|---|
| Component | Placebo | 1% | 4% |
| Hexylene glycol Fluka | 8.0 | 8.0 | 8.0 |
| Light Mineral Oil, NF Spectrum | 9.0 | 13.5 | 12.0 |
| PEG-6-Capric/Caprylic Glyceride, Ph. Eur. | 10.0 | 10.0 | 10.0 |
| Softigen 767, Sasol | | | |
| Nitricil ™ NVN1 Novan, Inc., Batch# 1200601 | — | 1.0 | 4.0 |

The test system used was a 7-day oxazolone-induced ear swelling assay. Oxazolone-induced ear swelling is useful as a model of inflammation. Oxazolone is an allergen that induces delayed type hypersensitivity, and is therefore most useful as a model of inflammation driven by the adaptive immune response (e.g., allergic contact dermatitis, psoriasis, etc). In this assay, mice (5 per group) were sensitized to oxazolone (100 μL, 1.5% in acetone) through one topical application of oxazolone to their preshaved abdomen surface. Seven days later, animals were challenged with a second application of oxazolone to the ear. Test articles (20 mg/mouse) and vehicle (20 μL/ear) were administered topically (TOP) to the anterior and posterior surfaces of the right ear 30 minutes before and 15 minutes after the second oxazolone (1%, 20 μL/ear) challenge (elicitation phase). Ear swelling was measured with a Dyer model micrometer gauge at 24 hours after oxazolone challenge as an index of inflammation. Ear edema was calculated by subtracting the thickness of the left ear (normal control) from the right ear (treated ear) (Table 9). An additional group was treated with dexamethasone, a known anti-inflammatory agent, (positive control) to verify assay validity. Percent inhibition was calculated according to the formula: $(Ic-It)/Ic \times 100$, where Ic and It refer to increase of ear thickness (mm) in control and treated mice, respectively. One-way ANOVA and Dunnett's test were used to determine statistical significance between vehicle control and treated groups. Significance is set at P<0.05.

TABLE 9

Treatment information and swelling results.

| Treatment | Route | Dose | Net Swelling on Right Ear (Mean ± SEM, ×0.01 mm) |
|---|---|---|---|
| Vehicle (Acetone:Ethanol/1:1) | TOP | 20 µL/ear × 2 | 22.6 ± 1.2 |
| Dexamethasone | TOP | 0.1 mg/ear × 2 | 3.2 ± 0.4* |
| Placebo ointment | TOP | 20 mg/ear × 2 | 23.2 ± 1.5 |
| 1% Nitricil™ NVN1 Topical Ointment | TOP | 20 mg/ear × 2 | 9.8 ± 1.2*, † |
| 4% Nitricil™ NVN1 Topical Ointment | TOP | 20 mg/ear × 2 | 9.2 ± 0.6*, † |

Note:
One-way ANOVA and Dunnett's test were used to ascertain difference between placebo/vehicle control and treated groups.
*P < 0.05, vs. Vehicle (Acetone:Ethanol/1:1).
†P < 0.05, vs. Placebo ointment.

Topical administration of 1% Nitricil™ NVN1 Topical Ointment and 4% Nitricil™ NVN1 Topical Ointment were both associated with significant (P<0.05) inhibition of oxazolone-induced ear swelling versus both the vehicle control (acetone/ethanol: 1/1) and placebo ointment. The 1% Nitricil™ NVN1 Topical Ointment inhibited ear swelling by 57% versus acetone/ethanol vehicle and by 58% versus placebo ointment. The 4% Nitricil™ NVN1 Topical Ointment inhibited ear swelling by 59% versus acetone/ethanol vehicle and by 60% versus placebo ointment. The placebo ointment had no effect on ear swelling relative to the acetone/ethanol vehicle. Dexamethasone (positive control) inhibited ear swelling by 86% relative to the acetone/ethanol vehicle.

Topical administration of Nitricil™ topical ointment at 1% and 4% caused significant (P<0.05) inhibition of the oxazolone-induced ear swelling in mice compared to the placebo ointment control or vehicle (Acetone/Ethanol: 1/1). Thus, Nitricil™ topical ointment 1% and 4% both significantly inhibited inflammation in an in vivo model of allergic contact dermatitis. The 4% Nitricil™ NVN1 Topical Ointment was not significantly more effective than the 1% Nitricil™ NVN1 Topical Ointment under the conditions of this test. The placebo ointment group did not have any effect relative to vehicle control (Acetone/Ethanol: 1/1). Dexamethasone (0.1 mg/mouse×2), the positive control, was associated with significant inhibition of the oxazolone-induced ear swelling in mice. Table 10 shows a comparison of the percent inhibition of the oxazolone-induced ear swelling results from this study, the study described in Example 2, and a subsequent study with Nitricil™ ointment formulations as described in Example 3 to an ethanol/acetone vehicle formulation or a placebo formulation. For the Nitricil™ NVN4 ointment formulations, the formulations were similar to those provided in Example 3 for the Nitricil™ NVN1 ointment formulations with minor adjustments made to the light mineral oil to account for the difference in the amount of Nitricil™ in the formulation.

TABLE 10

Comparison of the percent inhibition of the oxazolone-induced ear swelling results from various studies.

| | | % inhibition of oxazolone-induced ear swelling | |
|---|---|---|---|
| Example | Test Article | vs ethanol/acetone | vs placebo formulation |
| 2 | Placebo Ointment | −17 | n/a |
| 2 | 0.2% Nitricil™ NVN1 Ointment | −11 | 5 |
| 2 | 2% Nitricil™ NVN1 Ointment | −4 | 11 |
| 4 | Placebo Ointment | −3 | n/a |
| 4 | 1% Nitricil™ NVN1 Ointment | 57* | 58* |
| 4 | 4% Nitricil™ NVN1 Ointment | 59* | 60* |
| 3 | Placebo Ointment | 33* | n/a |
| 3 | 2.8% Nitricil™ NVN4 Ointment | 43* | 14* |
| 3 | 5.6% Nitricil™ NVN4 Ointment | 55* | 32* |
| 3 | 11.2% Nitricil™ NVN4 Ointment | 61* | 42* |
| 3 | 2% Nitricil™ NVN1 Ointment | 24* | −14 |
| 3 | 4% Nitricil™ NVN1 Ointment | 57* | 36* |
| 3 | 8% Nitricil™ NVN1 Ointment | 62* | 43* |

*Significant (P < 0.05) inhibition versus ethanol/acetone vehicle or placebo formulation.

Example 5

Wound Healing Study in a Porcine Partial-Thickness Wound Model

Using Nitricil™ NVN1 ointments, such as the TO-007 ointment formulations described in Example 8, partial thickness wounds were treated in a porcine model. Partial thickness wounds were treated with the following formulations: ointment formulations containing 0.1%, 0.5%, 1%, or 4% Nitricil™ NVN1, vehicle ointment, Tegaderm for standard occlusion as a positive control, or left air exposed as a negative control.

Figure 3:
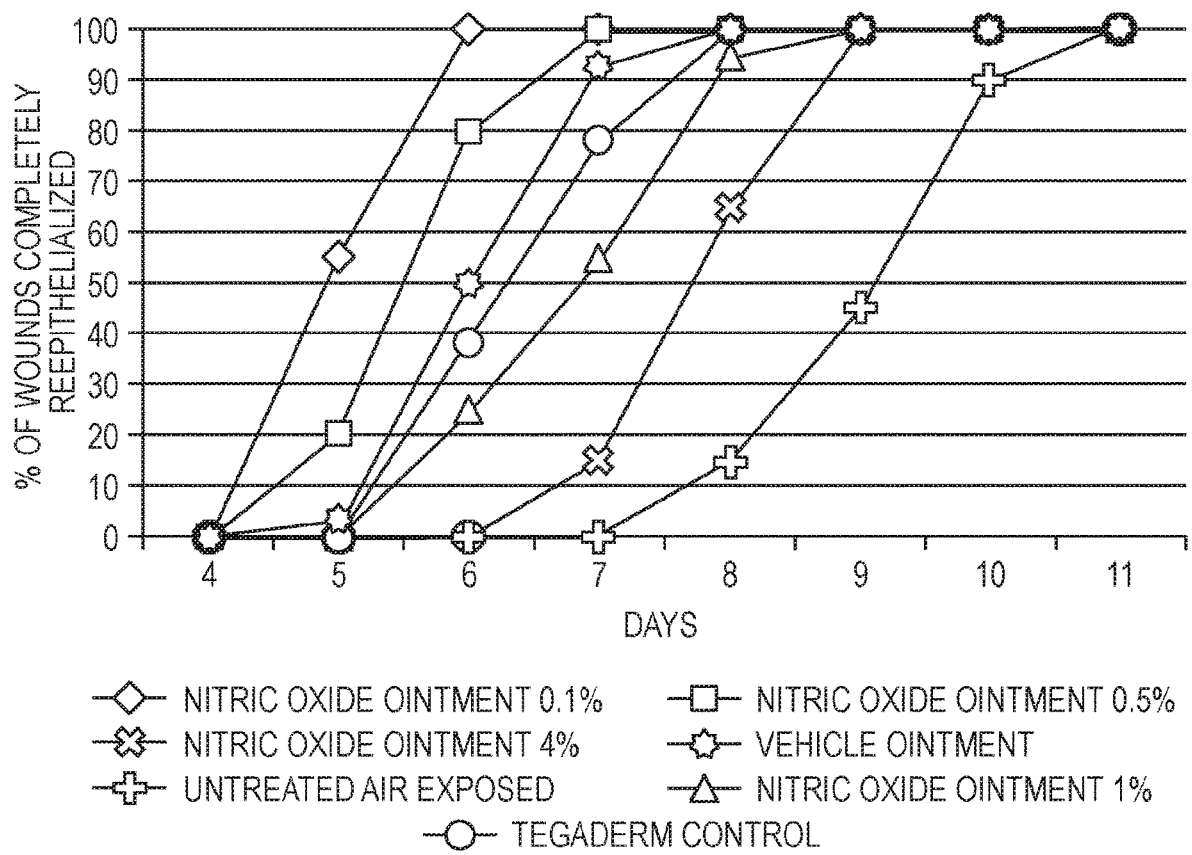
FIG. 3 shows a graph of the effect of nitric oxide-releasing Nitricil™ NVN1 ointment on wound re-epithelialization.

Results from the eight-animal wound healing study are shown in FIG. 3. The lower doses, 0.1% and 0.5% Nitricil™ NVN1 ointment, demonstrated much faster rates of re-epithelialization. All 20 wounds in the lowest dose (0.1%) were completely healed by Day 6, 2 full days faster than the corresponding ointment vehicle or the Tegaderm occlusive standard of care. Even though this data was not collected in a thermal injury model, it clearly demonstrates the ability of nitric oxide to stimulate faster healing.

Two biopsies were taken from all animals in each treatment group on Day 2, 4, and 7 post wounding. Wedge biopsies for histology were obtained through the center of the wounds including normal adjacent skin on both sides. Punch biopsies were taken from the other half of the wound for RNA isolation and subsequent RT-PCR analysis.

Figure 4:
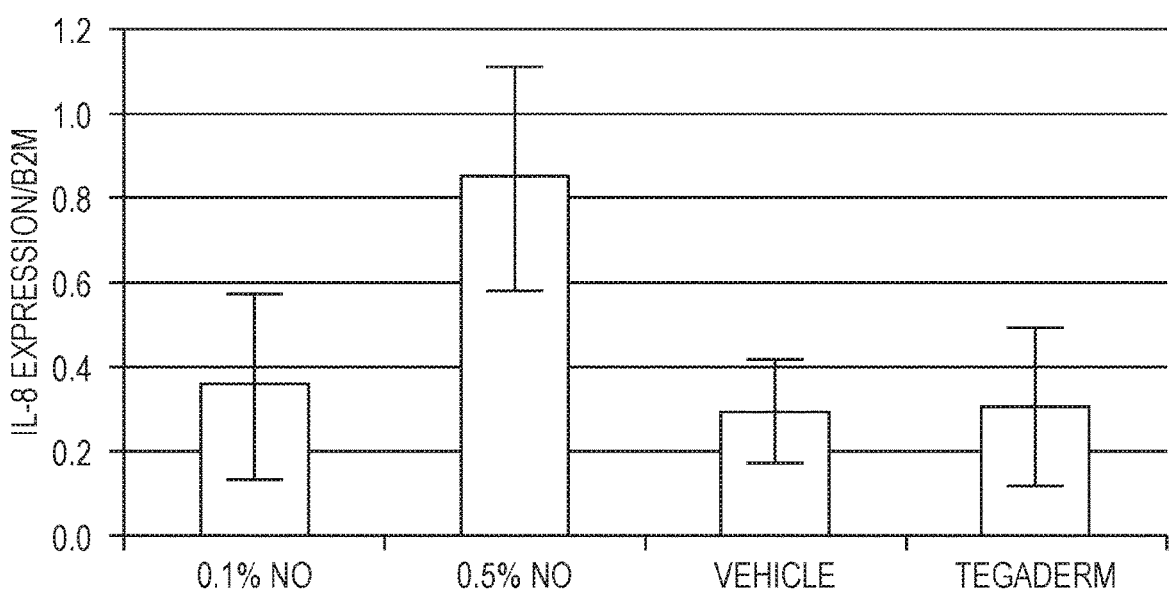
FIG. 4 shows a graph of the expression levels of IL-8 in wound tissue measured by qPCT in wounds treated with 0.1% and 0.5% Nitricil™ NVN1, vehicle, and Tegaderm.
Figure 5:
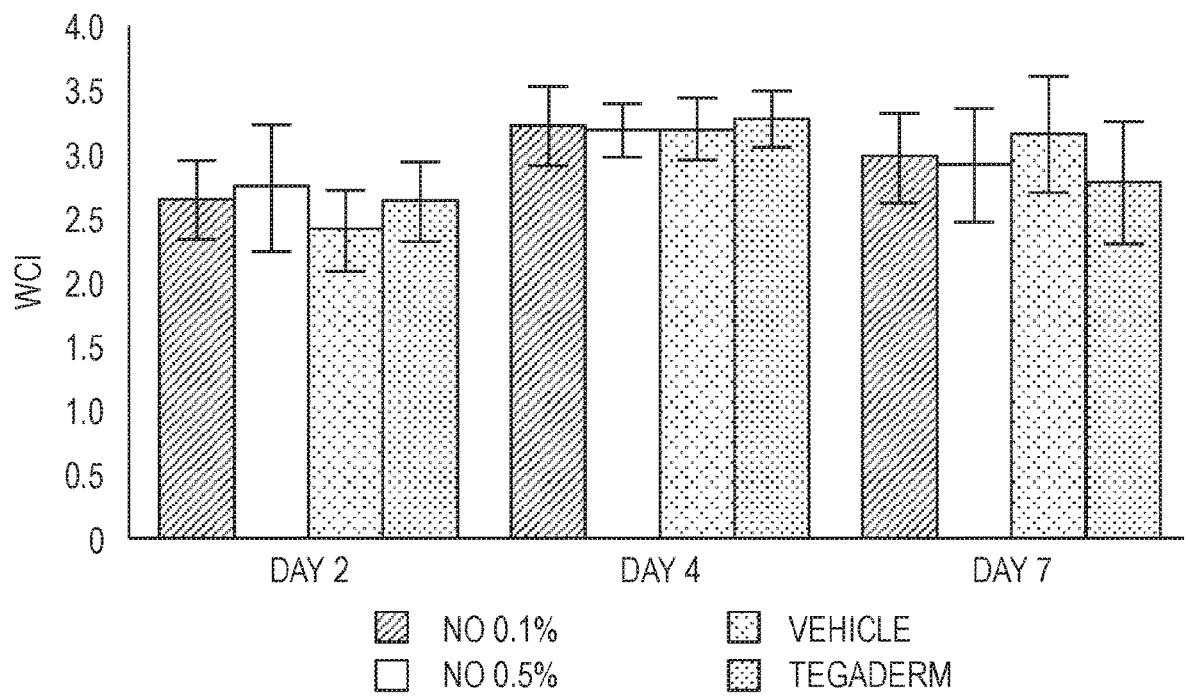
FIG. 5 shows a graph of the white cell infiltrate assessed by the presence and amount of subepithelial mixed leukocytic infiltrates.

No differences in epithelial thickness were observed for any of the treatment groups, showing a regulated healing process and no overproliferation of cells in the epithelium. Wounds treated with 0.5% Nitricil™ NVN1 ointment expressed an elevated level of IL-8 mRNA on Day 2 compared to the other treatment groups (FIG. 4). Expression of IL-8, a neutrophil chemoattractant, was significantly induced in wounds following 2 days of treatment with 0.5% Nitricil™ NVN1 ointment (p<0.05). Nitric oxide can activate the IL-8 promoter and IL-8 in turn can suppress the expression of iNOS in neutrophils. This signaling effect was enough to promote healing but did not facilitate over recruitment of neutrophils and cause a sustained inflammatory response (FIG. 5). The white cell infiltrate measured via histology was not statistically different for any of the treatments.

Example 6

Figure 6:
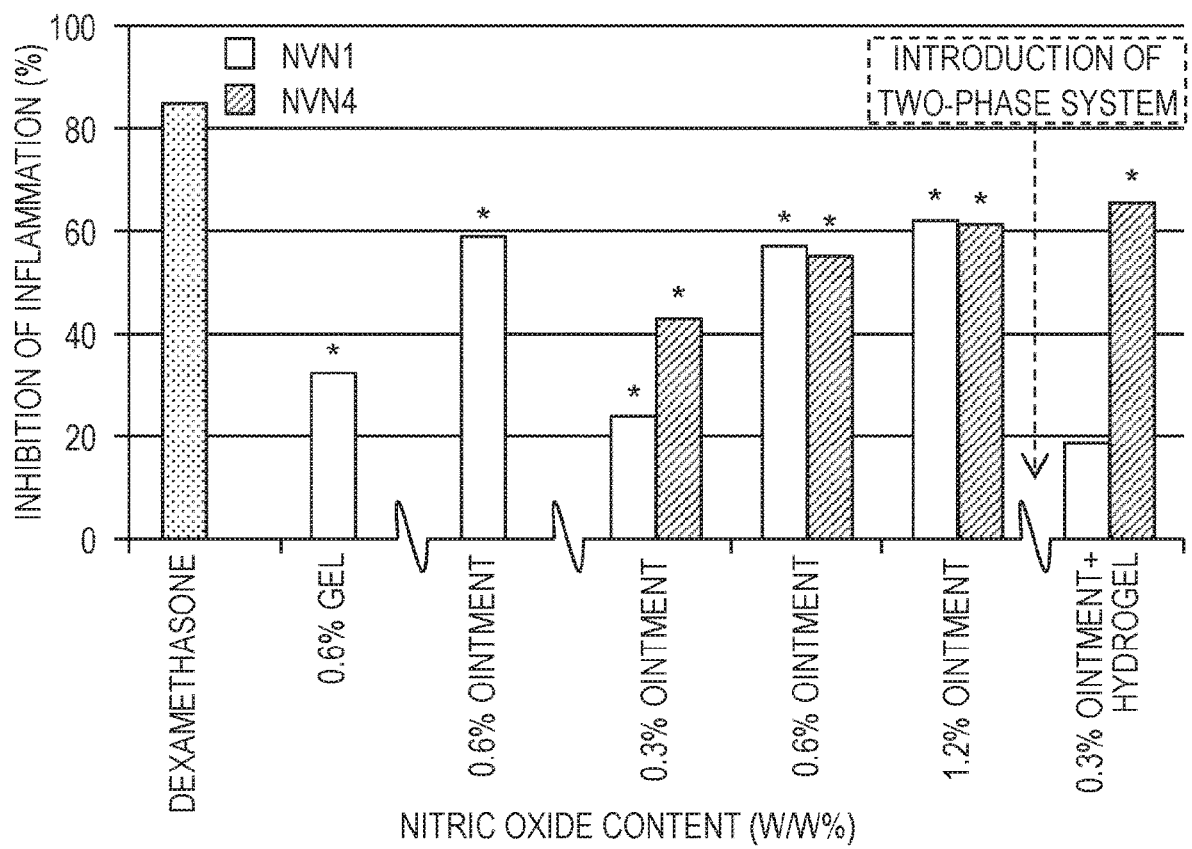
FIG. 6 shows a graph of the percent inhibition of inflammation for various test articles tested.

Oxazolone-Induced Ear Swelling in BALB/c Mice:

BALB/c mice are sensitized with oxazolone exposure to the abdomen and are subsequently challenged (7 days post-sensitization) with oxazolone application to the right ear. Anti-inflammatory test articles are applied to both ears 30 minutes prior to and 15 minutes following the oxazolone challenge. The effect of anti-inflammatory test articles is then assessed by measuring the amount of ear swelling, which is reported as a percentage in comparison to the study vehicle. Studies were performed to investigate the effect of fast versus slow release of nitric oxide as well as to screen formulation compositions. Taken together, the results from these studies have demonstrated that slow-release of nitric oxide via Nitricil™ NVN4, as an admixture composition, yields the greatest anti-inflammatory efficacy (FIG. 6).

Example 7

IL-23-Induced Psoriasis-Like Murine Model:

An IL-23-induced Psoriasis-like murine model thought to recapitulate a psoriasis-like inflammatory state was used. Mice received intradermal injections to the ear of the inflammation cytokine, IL-23, every other day over a twelve day timecourse. Test articles were applied topically once daily over the same twelve day timecourse. The effect of anti-inflammatory test articles was then assessed by measuring the amount of ear swelling, which is reported as a percentage in comparison to the study vehicle. Ear samples were obtained for both histology and cytokine analysis at the end of treatment.

Figure 7:
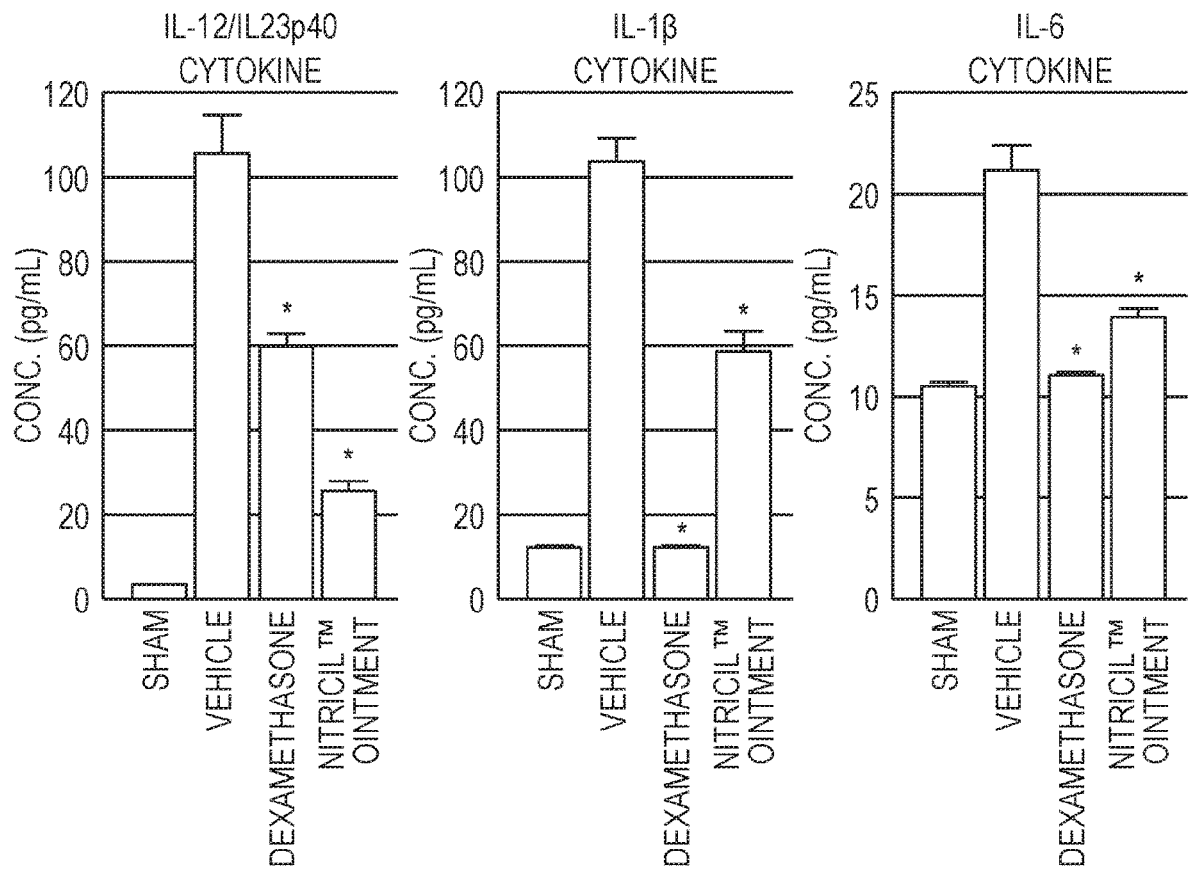
FIG. 7 shows graphs of the concentration of IL-12/IL23p40, IL-1β, and IL-6 cytokines for the Nitricil Ointment, vehicle, and dexamethasone.

As shown in FIG. 7, topical application of the TO-008 2% Nitricil™ NVN1 Ointment (Table 4) in the IL-23-induced psoriasis mouse model demonstrated statistically significant reductions of pro-inflammatory cytokines when compared to the Vehicle control. IL-23 stimulates Th17 cells to produce the cytokine IL-17 which in turn signals keratinocytes to release IL-1β and IL-6 among other cytokines. While not wishing to be bound to any particular theory, decreases in the levels of the pro-inflammatory cytokines IL-1β and IL-6 suggests that topical treatment with the Nitricil™ Ointment and compositions similar to the Nitricil™ Ointment may function as an IL-17 inhibitor. Furthermore, IL-17 normally stimulates keratinocytes to produce more IL-23 and continue the inflammatory loop important for prolonging the psoriatic lesion. While not wishing to be bound to any particular theory, the statistically significant reduction of IL23p40, observed at levels of expression lower than following treatment with dexamethasone positive control, suggests the Nitricil Ointment's potential to dampen the inflammatory loop associated with chronic psoriasis inflammation.

Example 8

LPS-Induced Cytokine Release Assay in Normal Human Skin Biopsies:

This study assesses the effects of test article formulations on LPS-stimulated cytokine release from normal healthy human skin obtained from healthy patients undergoing surgical breast reduction, reconstruction or abdominoplasty. Full-thickness 8 mm biopsies will be obtained using a biopsy punch. Biopsy samples are prepared and allowed to rest for 24 hours prior to LPS challenge. Biopsy samples are then challenged with a final concentration of 1 μg/mL LPS from *Escherichia coli*. Test article formulations are then applied topically to the epidermal surface of the biopsy and are kept in contact with the biopsy for 24 hrs. Following the 24 hour test article exposure, the culture media is collected from each well. Culture media samples will be analyzed for IL-6, IL-8, IL-10, IL-12p40, IL-1β and TNF-α by multiplex ELISA. Samples will be analyzed in duplicate and the mean value will be utilized for further analysis. The effect of Nitricil™ test article treatment versus untreated control, Placebo Cream, and a positive control (0.1% triamcinolone) will be analyzed.

Example 9

Reduction in Bacterial Counts of an Atopic Dermatitis (AD)-Specific Methicillin-Resistant *Staphylococcus aureus* Isolate in a Porcine Partial Thickness Wound Model:

This study will access the ability of Nitricil™ NVN4 Cream formulations, which include a Nitricil™ NVN4 ointment as provided in Table 11 (e.g., 20% Nitricil™ NVN4 ointment in Table 12) in admixture with the hydrogel as provided in Table 13, to reduce the microbial burden of Methicillin-Resistant *Staphylococcus aureus* (MRSA) following topical treatment to infected compromised skin. The isolate of MRSA being utilized for this study was isolated from an inflammatory flare of an atopic dermatitis patient. As the skin of AD patients is compromised, a porcine partial thickness wound model is utilized to mimic an impaired epidermal barrier with a high *S. aureus* burden, such as those observed during times of inflammatory flares in AD patients. Animals receive partial thickness wounds with a specialized electrokeratome to create wounds measuring 10 mm×7 mm×0.5 mm Immediately following wounding, all wounds are inoculated with the AD-specific MRSA isolate and covered with a polyurethane film dressing. Biofilms are allowed to establish for 48 hours prior to the application of topical treatment. Following 48 hrs, three wounds are recovered to establish baseline bacterial counts. Once daily topical treatment application commences on Day 2 and each wound is treated with enough test article (~300 mg) to cover the wounded area and surrounding unwounded skin and then covered with an occlusive dressing. Quantitative microbiology is assessed following two (Day 4) and five (Day 7) days of treatment with Nitricil™ NVN4 Cream. Three pigs are utilized in order to obtain statistics and allow for statistical assessment to be achieved for 1- or 2-log deltas between treatment groups. The average results from two of the three pigs (Pig #1 and 2) are summarized in FIG. 8.

Figure 8:
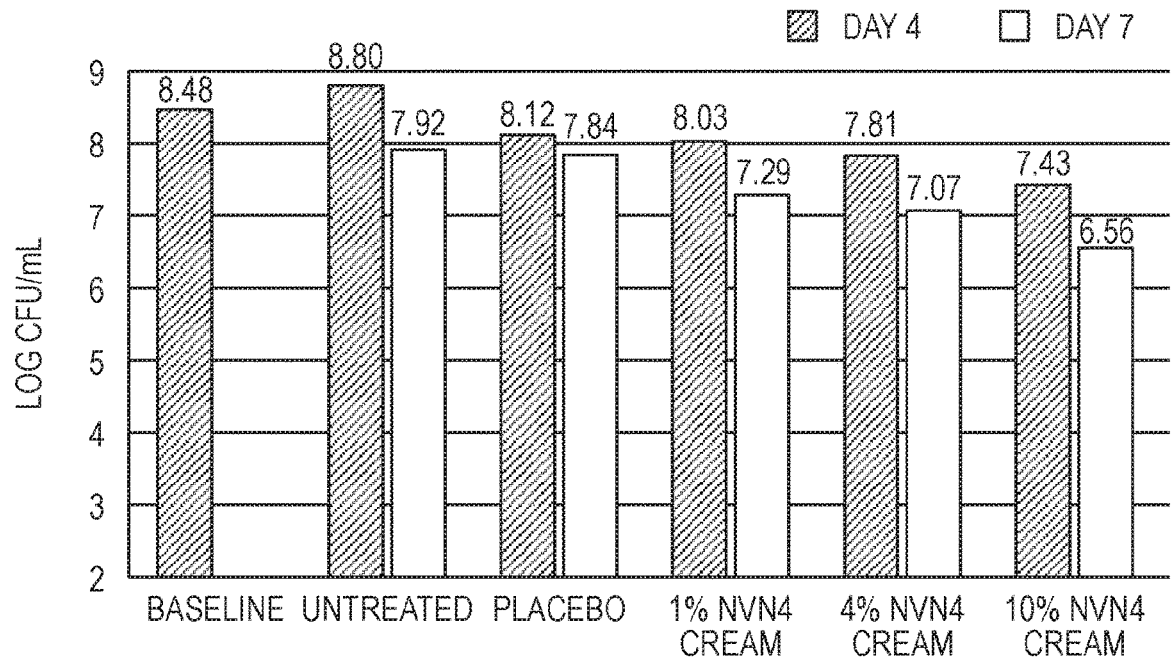
FIG. 8 shows a graph of the AD-specific MRSA counts after topical treatment.

As can be seen in FIG. 8, following five topical treatment applications (Day 7) a nearly two-log reduction in the AD-specific MRSA bacterial counts is observed when comparing treatment with 10% Nitricil NVN4 Cream to the baseline MRSA counts. Importantly, a nice dose-responsive treatment effect is observed as the efficacy increases with increasing strengths of Nitricil NVN4 Cream.

Example 10

IL-17-Induced Cytokine Assay in Normal Human Skin Biopsies:

In a manner similar to the LPS-induced cytokine release assay described above in Example 13, full-thickness skin biopsies are obtained from health human skin. To stimulate the Th17/IL-17 pathway the skin biopsies are treated with a proprietary cytokine cocktail for 48 hrs. At the end of the cytokine cocktail incubation period potent induction of IL-17 cytokine release is observed. Additionally, the expression of important IL-17 pathway genes is upregulated and includes: IL-17a, IL-17f, and IL-22. Furthermore, the secretion of other important cytokines is observed (TNF-α, GM-CSF, and IFN-γ). In this model the common psoriatic therapy calcipotriol, a vitamin D analogue, partially inhibits the IL-17a pathway as evidenced by a partial inhibition of IL-17 secretion. While not wishing to be bound by any particular theory, formulations that show efficacy in this in vitro model may have an effect on the Th17/IL-17 pathway, which is important for the pathogenesis of psoriasis.

Example 11

Cytokine Assay in Psoriatic Skin Biopsies:

In this model, patients diagnosed with severe plaque psoriasis by a qualified clinician are recruited for the study. Four plaque biopsies and one non-plaque control biopsy are obtained from each patient. Biopsies (2 mm diameter) are cultured for 72 hours (+ an overnight rest period) following removal from the patient. During this 72 hour culture, biopsies can be treated topically with test article formulations. Following exposure, the level of important cytokines can be obtained via ELISA (IL-10, IL-17, IL-22, and IFN-γ). In non-plaque biopsies, the level of these cytokines falls below the limit of quantification. However, plaque biopsies have quantifiable cytokine levels and, while not wishing to be bound by any particular theory, their reduction following test article exposure may indicate the efficacy of topical treatment.

Example 12

Imiquimod-Induced Psoriasis-Like Murine Model:

Imiquimod (IMQ) is a ligand for both toll-like receptors TLR7/TLR8 and a potent immune activator available commercially that is used for the topical treatment of genital warts, superficial basal cell carcinomas, and actinic keratosis. Topical application of imiquimod exacerbates psoriasis at both locally-treated areas as well as distal sites. The IMQ-induced psoriasis mode is recognized as a clinically-relevant model of human plaque-type psoriasis. Similar to human psoriasis, IL-23/IL-17 axis plays a pivotal role in IMQ-induced psoriasis in mice. Application of IMQ on the ears and hair-free backs of mice results in the development of psoriasis-like lesions within five days of topical administration. This results in an influx of a variety of cells (T cells, dendritic cells, macrophages) as well as epidermal hyperplasia. In this model IMQ cream is applied to the shaved back and the right ear daily for ten consecutive days. Test articles are also topically applied daily over this time course. Right ear thickness is measured with calipers at baseline, day 5, 8 and 10. All animals are also evaluated on their backs for a psoriasis disease severity score which is determined by the sum of the erythema score and plaques score (both on a scale of 0-4; 0=normal and 4=severe). Skin from the back of the animals can also be harvested terminally (day 10) and histological analysis (H&E staining) of the skin for epidermal changes is scored on a scale of 0-4. The score is a subjective evaluation of overall lesion severity based on the following parameters: extent of lesion, severity of hyperkeratosis, number and size of pustules, height of epidermal hyperplasia, and degree of inflammation in the dermis and soft tissue. Finally, tissues can be harvested from animals that are terminated on day 3 for mRNA analysis of: IL-22, IL-17a, IL-17f, TNF-α, IL-33, and IL-1β. This model can be utilized to assess disease severity in vivo through gross examination, qualitative histopathology, and cytokine mRNA expression.

Example 13

Nitricil™ formulations are developed for use in one or more of the above examples. For example, an ointment may have a composition as provided in Tables 11 and 12, below, and a hydrogel may have a composition as provided in Table 13, below. A hydrogel may have a pH in a range of 4.5-5.3.

TABLE 11

Composition of Nitricil ™ NVN4 Ointments.

| Ingredient | Weight % | Function |
| --- | --- | --- |
| Nitricil ™ NVN4 | 0.01-50 | Active Pharmaceutical Ingredient (API) |
| Crodabase SQ | 0-45 | Hydrocarbon Base |
| Petrolatum, White, USP | 0-45 | Hydrocarbon Base |
| Mineral Oil, USP | 1-10 | Solvent |
| Softigen 767 | 0-15 | Solvent |
| Miglyol 812 | 0-15 | Amphiphilic Agent/Solvent |

TABLE 12

Composition of ointments comprising 0.8%, 2%, 8%, 10%, and 20% Nitricil ™ NVN4.

| Ingredient | % w/w | | | | |
| --- | --- | --- | --- | --- | --- |
|  | 0.8% | 2% | 8% | 10% | 20% |
| Petrolatum, White | 40.10 | 39.50 | 37.00 | 36.00 | 31.00 |
| Crodabase | 40.10 | 39.50 | 37.00 | 36.00 | 31.00 |
| Miglyol 812 | 10.00 | 10.00 | 10.00 | 10.00 | 10.00 |
| Mineral Oil | 5.00 | 5.00 | 4.00 | 4.00 | 4.00 |
| Softigen 767 | 4.00 | 4.00 | 4.00 | 4.00 | 4.00 |
| NVN4 | 0.80 | 2.00 | 8.00 | 10.00 | 20.00 |
| Total | 100.0 | 100.0 | 100.0 | 100.0 | 100.0 |

TABLE 13

Composition of PHO-048 hydrogel having a pH of 4.8.

| Ingredient | % w/w |
| --- | --- |
| Purified water | 72.80 |
| Hexylene glycol | 19.00 |
| Monopotassium phosphate | 5.20 |
| Hydroxyethyl Cellulose Ethoxylatequarternized | 3.00 |
| Total | 100.0 |

Figure 9:
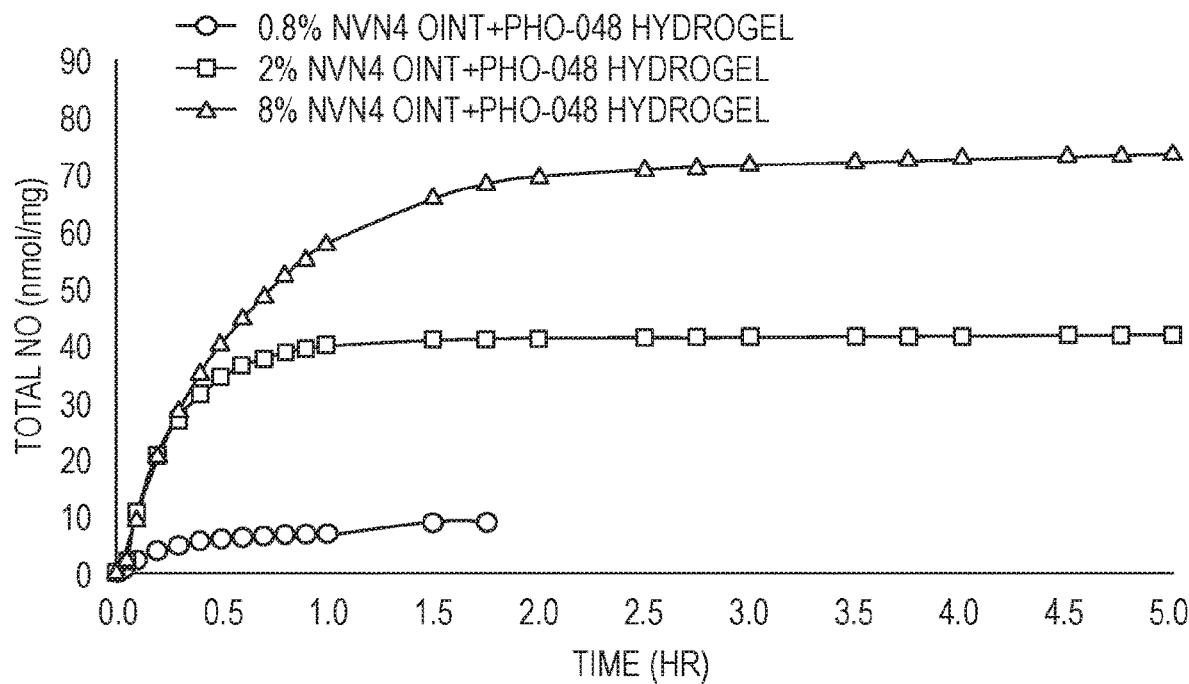
FIG. 9 shows a graph of the cumulative NO release for 0.8%, 2%, and 8% Nitricil™ NVN4 Ointments with the PHO-048 hydrogel.
Figure 10:
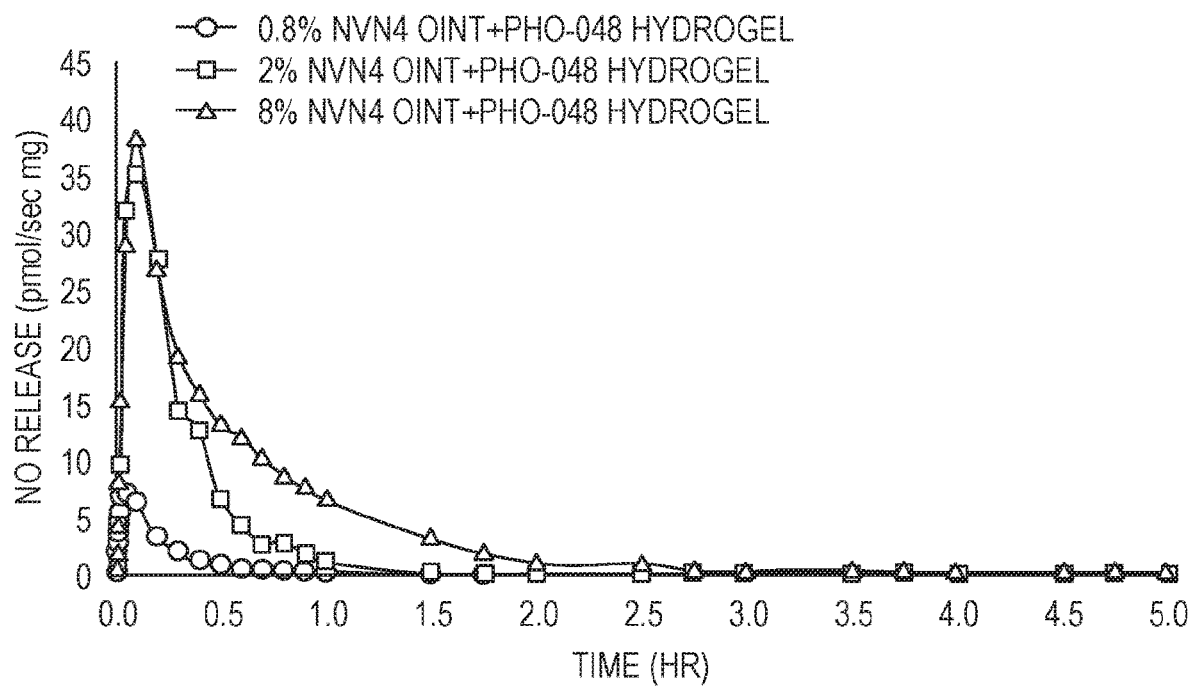
FIG. 10 shows a graph of the instantaneous NO release for 0.8%, 2%, and 8% Nitricil™ NVN4 Ointments with the PHO-048 hydrogel.

The NO release profiles/rates for the 0.8%, 2%, and 8% Nitricil™ NVN4 Ointment as provided in Table 12 with the pH 4.8 PHO-048 hydrogel of Table 13 are shown in FIGS. 9 and 10.

Example 14

An oxazolone-induced delayed-type hypersensitivity BALB/c mouse model was used to assess anti-inflammatory activity. Sensitized mice display increased scratching behavior, which is thought to mimic the intense pruritus experienced by atopic dermatitis patients. The allergic contact dermatitis induced by oxazolone results in an immune response that aims to model the chronic phase of atopic dermatitis.

Figure 11:
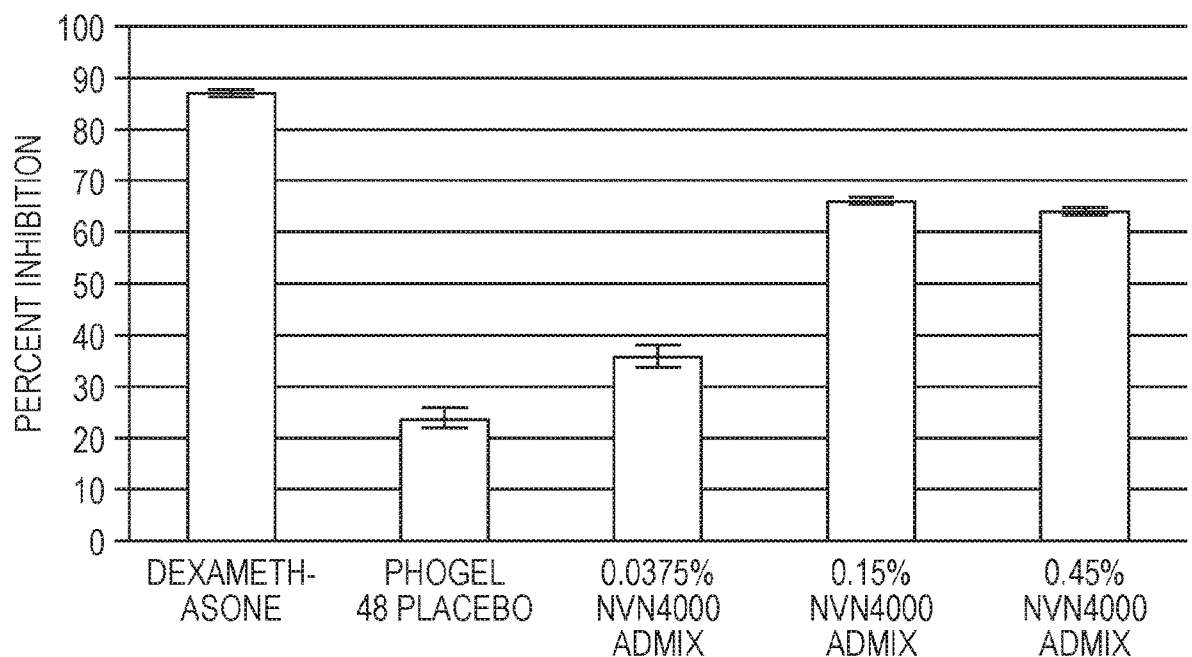
FIG. 11 shows a graph of the percent inhibition after topical application of Nitricil™ NVN4 Creams, each of which included an ointment in admixture with a hydrogel.

Dose-dependent responses have been observed with gel formulations, but, when formulated into an ointment, more favorable reductions in swelling were observed. The addition of a hydrogel to the ointment to form a cream admixture resulted in selection of the slow-releasing formulation containing the Nitricil™ NVN4 API. Preclinical studies illustrate that cream formulations that are an admixture of an ointment and hydrogel work better than the ointment alone in acute models of contact dermatitis by delivering enhanced anti-inflammatory activity at lower doses of nitric oxide. As shown in FIG. 11, topical application of Nitricil™ NVN4 Creams, each of which included an ointment as provided in Table 11 in admixture with the hydrogel provided in Table 13, showed a decrease in swelling and that one Nitricil™ NVN4 Cream showed a 66% decrease in swelling following topical administration compared to the high potency steroid dexamethasone.

Example 15

An imiquimod-induced psoriasis-like murine model as described in Example 17 was used to evaluate the effect of NO-releasing admixtures containing a hydro gel and an ointment comprising a NO-releasing compound.

Animals received an imiquimod cream application (i.e., disease stimulant) to their ears and backs daily for Days 0-9. Two hours post-imiquimod application the animals were topically dosed with test article formulations to their back and ears For application to the back, the admixture test formulations were mixed immediately prior to application to generate a homogenous mixture. A dose of 4 g/kg of the admixture (total weight of mixed ointment and hydrogel) was applied. For application to the ears, the same dosing procedure was employed as for administration to the back, but a dose of 2 g/kg was applied to the ears.

Four hours following the first test article dosing a second application of the respective test articles was applied to the back and ears of all animals The admixture test articles consisted of a hydrogel, as provided in Table 14, that was mixed with one of the ointment compositions provided in Table 15 in a 1:1 ratio. Thus, for example, the hydrogel when admixed with the 1% Nitricil™ NVN1 ointment composition provides a 0.5% Nitricil™ NVN1 admixture composition. The hydrogel had a pH in a range of about 4 to about 4.5. After an hour, the pH of the admixture composition may be in a range of about 4.5 to about 6. For example, at t=0 the pH of the 6% Nitricil™ NVN1 admixture composition was 6.1 and at t=1 hour the pH of the 6% Nitricil™ NVN1 admixture composition was 5.27.

TABLE 14

Hydrogel Composition (AC-004).

| Component | Function | % w/w |
|---|---|---|
| Sodium carboxymethyl cellulose | viscosity-modifying agent | 2.8 |
| Benzoic Acid | preservative | 0.1 |

TABLE 14-continued

Hydrogel Composition (AC-004).

| Component | Function | % w/w |
|---|---|---|
| 2M Acetic Acid | buffering agent | 38.4 |
| 2M Sodium Acetate | buffering agent | 48.7 |
| Glycerin | Solvent/humectant | 10.0 |

TABLE 15

Ointment Compositions.

| | % w/w | | | |
|---|---|---|---|---|
| Component | Placebo | 1% | 4% | 12% |
| Mineral Oil and Polyethylene Crodabase SQ, Croda | 84.0 | 83.16 | 80.64 | 73.92 |
| Cetyl Alcohol, NF | 4.0 | 3.96 | 3.84 | 3.52 |
| Mineral Oil, NF Spectrum | 8.0 | 7.92 | 7.68 | 7.04 |
| PEG-6-Capric/Caprylic Glyceride, Ph. Eur. Softigen 767, Sasol | 4.0 | 3.96 | 3.84 | 3.52 |
| Nitricil ™ NVN1 Novan, Inc. | — | 1.0 | 4.0 | 12.0 |

Topical treatment with all doses of the Nitricil™ NVN1 admixture compositions (i.e., 0.5%, 2%, and 6% Nitricil™ NVN1 admixture compositions) resulted in moderate reductions in the composite psoriasis scores observed on the animals' backs following 10 days of topical dosing. The 6% Nitricil™ NVN1 admixture composition resulted in the greatest reduction in psoriasis disease severity as measured by a statistically significant reduction in both the scaling score and the composite psoriasis score when compared to treatment with the Placebo admixture composition. In addition, treatment with a Nitricil™ NVN1 admixture composition, particularly at 0.5% and 2% Nitricil™ NVN1, resulted in inhibition of proinflammatory cytokines assessed from ear punch biopsies taken at Day 4. Treatment with the lower admixture doses (0.5% and 2% Nitricil™ NVN1) resulted in a 75% or greater reduction in IL-17A and IL-17F, the two cytokines most frequently associated with the psoriasis phenotype, when compared to the disease-only control animals. At these lower doses a greater than 50% reduction in IL-1β cytokine levels was also observed versus the disease only controls.

Figure 12:
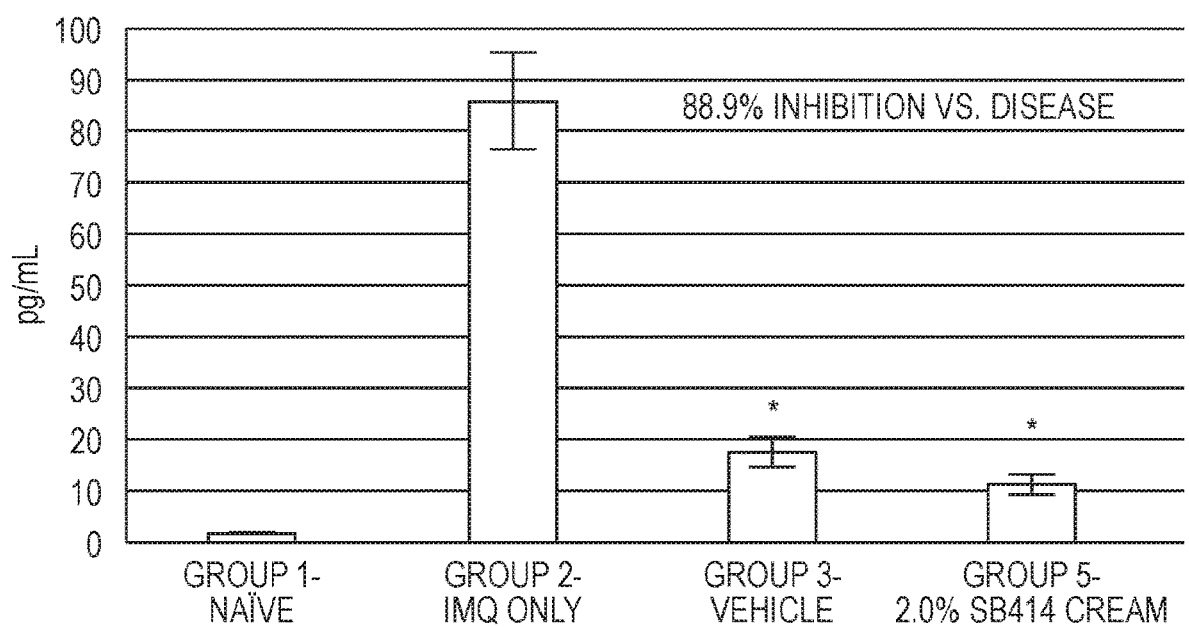
FIG. 12 is a graph showing the amount of IL-17A for groups receiving no treatment, imiquimod cream application (disease induction), vehicle treatment (i.e., the Placebo admixture composition), or the 2% Nitricil™ NVN1 admixture composition (i.e., 2% SB414 Cream). *$p<0.05$ vs. IMQ-only.
Figure 13:
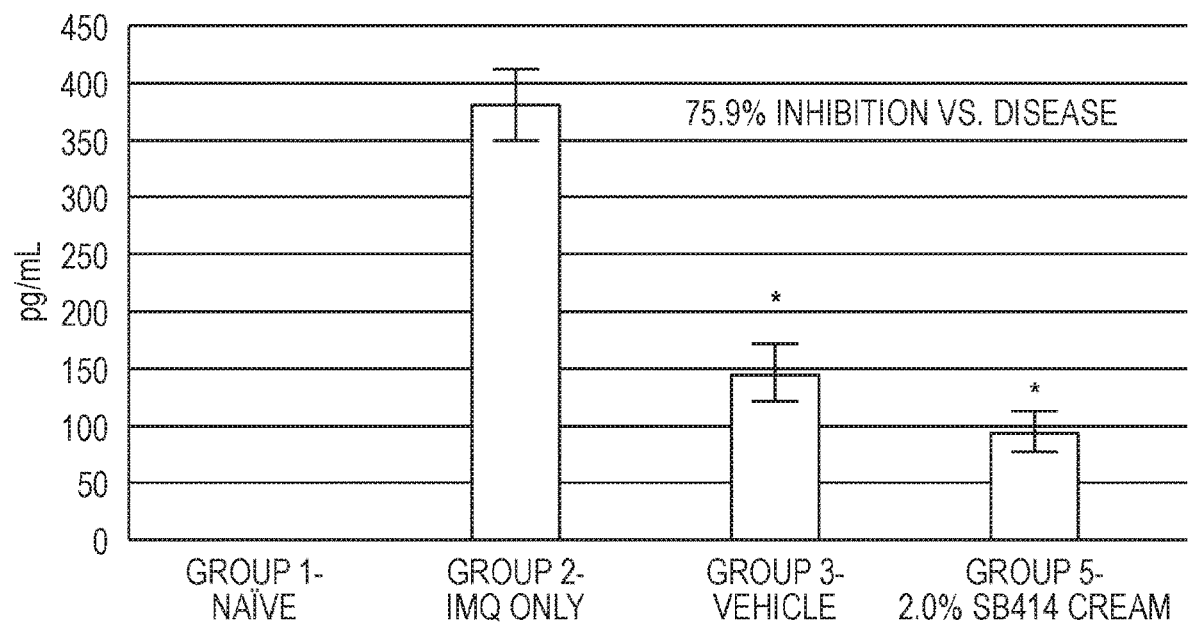
FIG. 13 is a graph showing the amount of IL-17F for groups receiving no treatment, imiquimod cream application (disease induction), vehicle treatment (i.e., the Placebo admixture composition), or the 2% Nitricil™ NVN1 admixture composition (i.e., 2% SB414 Cream). *$p<0.05$ vs. IMQ-only.
Figure 14:
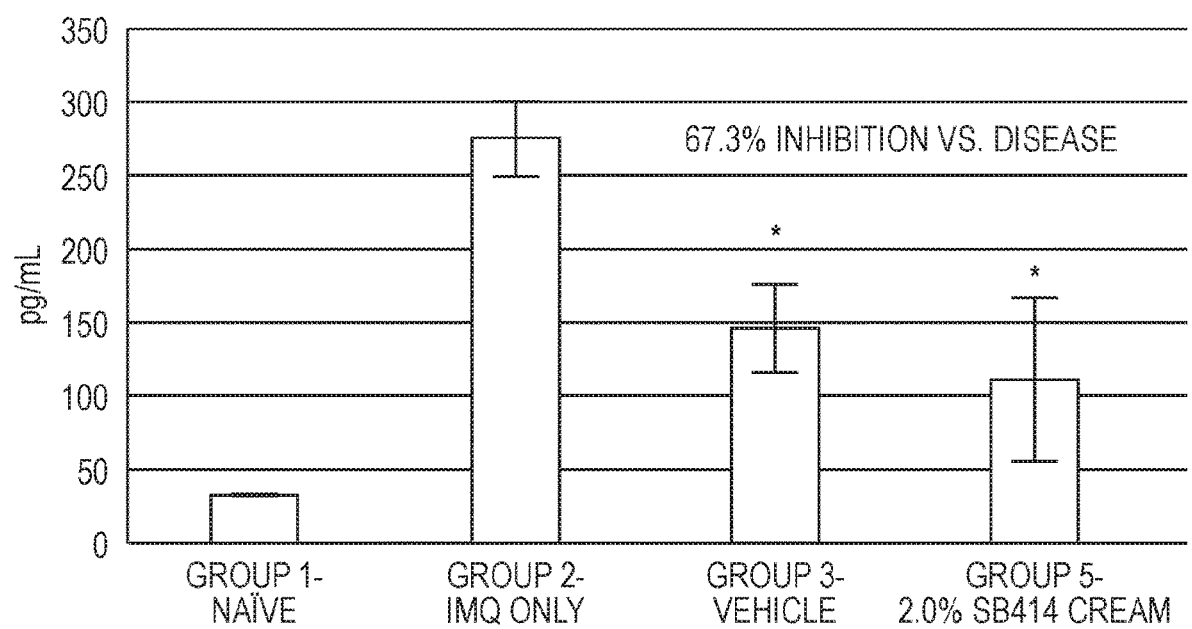
FIG. 14 is a graph showing the amount of IL-1β for groups receiving no treatment, imiquimod cream application, vehicle treatment (i.e., the Placebo admixture composition), or the 2% Nitricil™ NVN1 admixture composition (i.e., 2% SB414 Cream). *$p<0.05$ vs. IMQ-only.

FIGS. 12-14 show ear cytokine assessments for IL-17A, IL-17F, and IL-1β, respectively, for groups receiving no treatment, imiquimod cream application, vehicle treatment (i.e., the Placebo admixture composition), or the 2% Nitricil™ NVN1 admixture composition (i.e., 2% SB414 Cream) with *p<0.05 vs. IMQ-only.

Table 16 provides data from the back assessments for administration with the placebo admixture composition and the 6% Nitricil™ NVN1 admixture composition.

TABLE 16

Comparison of results from the placebo admixture composition and the 6% Nitricil™ NVN1 admixture composition.

| Treatment | Erythema (% Reduction) | | Scaling (% Reduction) | | Composite Score (% Reduction) | |
|---|---|---|---|---|---|---|
| Placebo Admixture | vs. Disease 31.25%* | | vs. Disease 11.11%* | | vs. Disease 16.39%* | |
| SB414 Cream | vs. Disease 39.60%* | vs. Vehicle 12.15% | vs. Disease 28.14%* | vs. Vehicle 19.16%* | vs. Disease 31.15%* | vs. Vehicle 17.65%* |

*$p < 0.05$

Treatment with the 6% Nitricil™ NVN1 admixture composition resulted in a statistically significant reduction in the composite psoriasis score, which includes erythema and plaque scores, indicating an effect on the gross disease pathology. All doses of the Nitricil™ NVN1 admixture compositions decreased key proinflammatory cytokines integral to the underlying inflammation associated with psoriasis.

Overall, Nitricil™ NVN1 admixture compositions demonstrated an anti-inflammatory effect in a relevant mouse model of psoriasis. Results from this study showed an inhibition of key cytokines (IL-17A, IL-17F, and IL-1β), inhibition of gross clinical psoriasis score, and comparable efficacy with approved psoriasis drugs.

Example 16

Topical application of imiquimod exacerbates psoriasis at both locally-treated areas as well as distal sites. The IMQ-induced psoriasis model is recognized as a clinically-relevant model of human plaque-type psoriasis. Similar to human psoriasis, IL-23/IL-17 axis plays a pivotal role in IMQ-induced psoriasis in mice. Application of IMQ on the ears and hair-free backs of mice results in the development of psoriasis-like lesions within five days of topical administration. This results in an influx of a variety of cells (T-cells, dendritic cells, macrophages) as well as epidermal hyperplasia.

In this model, IMQ cream was applied to the shaved back and both ears of mice daily for ten consecutive days. Test articles were also topically applied daily over this time course with the first test article application occurring 2 hours following IMQ dosing. In this study, a second topical test article application was applied 4 hrs after the initial daily test article application to achieve twice daily topical dosing of all test articles. Ear thickness was measured with calipers at baseline, day 3, 5, 8 and 10. All animals were evaluated on their backs for a psoriasis disease severity score, which was determined by the sum of the erythema score and plaques score (erythema on a 0-4 scale; 0=normal and 4=severe and plaques on a 0-7 scale; 0=normal and 7=50-100% of back involvement). Skin from the back of the animals was also harvested terminally (day 10) and histological analysis (H&E staining) of the skin for epidermal changes is scored on a scale of 0-4. The score is a subjective evaluation of overall lesion severity based and assesses each of the following parameters: hyperkeratosis, subacute dermal inflammation, and epidermal exudates (scale=0-4; 0=normal and 4=marked). In addition, epidermal thickening is also scored (score 0-4; 0=<30 µm, 1=30-50 µm, 2=50-80 µm, 3=80-110 µm, and 4=>110 µm. Finally, tissues can be harvested from the left ear of study animals on day 4 for protein analysis of: IL-22, IL-17a, IL-17f, TNF-α, IL-33, and IL-1β. This model can be utilized to assess disease severity in vivo through gross examination, qualitative histopathology, and cytokine protein expression.

Twice daily topical application of 6% SB414 Cream (12% NVN1 Ointment (Table 15)+AC-004 Hydrogel (Table 14)) resulted in a reduction in the clinical composite psoriasis score compared to the vehicle only (Placebo Cream (Placebo (Table 15)+AC-004 Hydrogel (Table 14)) that was significant by study day 3 and continued throughout the study. Compared to untreated controls, the 6% SB414 Cream demonstrated a statistically significant reduction in the psoriasis back pathology starting at day 3 and was maintained until the end of the experiment showing a 31% decrease in composite psoriasis score. At study termination, a mean 39.6% reduction in erythema versus untreated control animals was observed for the 6% SB414 Cream. Similarly, a mean statistically significant 28.1% reduction in psoriasis scaling was observed for the 6% SB414 Cream when compared to untreated disease-only animals on Study Day 10. In this model, pro-inflammatory cytokines associated with the IL-23/IL-17 axis are significantly upregulated in ear tissue after IMQ application with peak levels observed on Day 4. Compared to untreated disease controls, 6% SB414 treatment reduced ear tissue levels of pro-inflammatory cytokines: IL-1β, IL-6, IL-22, IL-17A, IL-17F and IL-33 by 84%, 55%, 64%, 87%, 71% and 71%, respectively.

While not wishing to be bound to any particular theory, twice daily topical application of 6% SB414 Cream is believed to achieve efficacy in this model in part due to the enhanced pH control of the formulation which may be attributed to the buffering system (acetic acid and sodium acetate). This buffering system may allow for the pH of higher strength NVN1 Admixtures (e.g., those containing Nitricil™ NVN1 in an amount ≥2.0%) to be buffered to an acid to neutral range (e.g., pH between 4.5 and 6).

Example 17

SB414 Cream was tested in two in vivo models that probe components of atopic dermatitis (AD) pathology. The complex etiology of AD involves defects in skin barrier function, cutaneous hypersensitivity to environmental triggers, and both systemic and local immunologic responses. To assess gross anti-inflammatory activity, ear swelling was quantified in an oxazolone-induced murine model of contact hypersensitivity as described in Examples 2 and 4. Following a single topical treatment, a dose-dependent effect was observed, with the highest dose 6% SB414 Cream, resulting in a statistically significant (SS) 76% reduction in ear swelling as compared to untreated animals, which compared favorably to the 80% reduction achieved with 0.05% betamethasone cream.

The admixture test articles consisted of a hydrogel, as provided in Table 14, that was mixed with one of the ointment compositions provided in Table 15 in a 1:1 ratio. The percent inhibition of ear swelling for each of the test articles tested and a 0.05% betamethasone cream are provided in Table 17.

TABLE 17

Percent inhibition of ear swelling compared to untreated.

| Treatment Group | % Inhibition vs. Untreated |
| --- | --- |
| 0.05% Betamethasone Cream | 80% |
| Placebo Cream (placebo ointment + AC-004) | 55% |
| 0.5% SB414 Cream (1% Nitricil ™ NVN1 ointment + AC-004) | 48% |
| 2% SB414 Cream (4% Nitricil ™ NVN1 ointment + AC-004) | 67% |
| 6% SB414 Cream (12% Nitricil ™ NVN1 ointment + AC-004) | 76% |

While not wishing to be bound to any particular theory, the decreased expression of antimicrobial peptides and skin barrier defects in AD patients may contribute to their enhanced susceptibility to secondary skin infections. In AD patients, *S. aureus* colonization has been shown to correlate with severity of lesions and cutaneous inflammation. The ability of topical SB414 Cream to reduce *S. aureus* bacterial counts was assessed in a porcine infected skin wound model. Dermatomed partial thickness skin defects were infected with *S. aureus* and biofilms developed for 2 days, followed by either 2 or 5 days of once daily topical dosing. Results demonstrated a SS and dose-dependent reduction of *S. aureus* bacterial counts with SB414 as compared to untreated baseline wounds. The greatest efficacy was achieved with the highest dose after 5 days of treatment exhibiting a greater than 3-log reduction (3.46±0.03 Log CFU/mL) when compared to baseline.

Example 18

The pH of admixture test articles was tested at 1 hour and at 24 hours and the pH at these two time points is provided in Table 18. The admixture test articles consisted of a hydrogel, as provided in Table 14, that was mixed in a 1:1 ratio with one of the ointment compositions provided in Table 15 or a 20% Nitricil™ NVN1 ointment (Table 19). The pH of each admixture was determined by weighing out about 1 gram of ointment into a container and adding about 1 gram of hydrogel. Then, mixing the mixture with a spatula for about 30 seconds. Covering the container with a screw top lid and loosening the screw top lid by about ¼ turn to allow for gas evolution during incubation period. At specified time points (generally t=1 hr post mixing and t=24 hrs post mixing) measuring the pH of the admixture with a flat end pH probe and corresponding meter. Three different locations within the admixture are read for pH value and these 3 replicates are averaged to determine the time point pH value.

TABLE 18

Test article pH.

| Test Article | pH at 1 hour | pH at 24 hours |
| --- | --- | --- |
| Placebo Ointment + AC-004 | 4.70 | 4.70 |
| 0.5% SB414 Cream (1% Nitricil ™ NVN1 ointment + AC-004) | 4.74 | 4.73 |
| 2% SB414 Cream (4% Nitricil ™ NVN1 ointment + AC-004) | 4.90 | 4.95 |
| 6% SB414 Cream (12% Nitricil ™ NVN1 ointment + AC-004) | 5.55 | 5.65 |
| 10% SB414 Cream (20% Nitricil ™ NVN1 ointment + AC-004) | 5.36 | 5.48 |

TABLE 19

20% Nitricil ™ NVN1 ointment formulation.

| Ingredient | % w/w |
| --- | --- |
| Crodabase SQ | 68.0 |
| NVN1000 | 20.0 |
| Cetyl Alcohol, NF | 4.0 |
| Mineral Oil, USP | 4.0 |
| Softigen 767 | 4.0 |
| Total: | 100.0 |

Example 19

Figure 15:
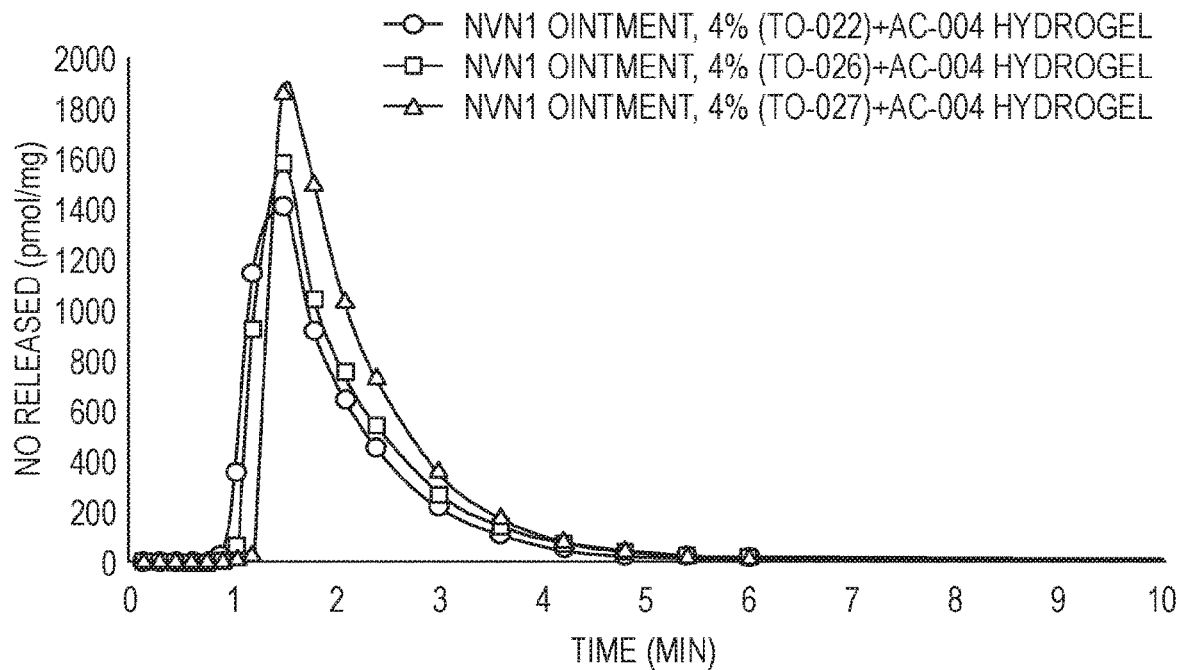
FIG. 15 shows a graph of the instantaneous NO release over time for three different admixtures.
Figure 16:
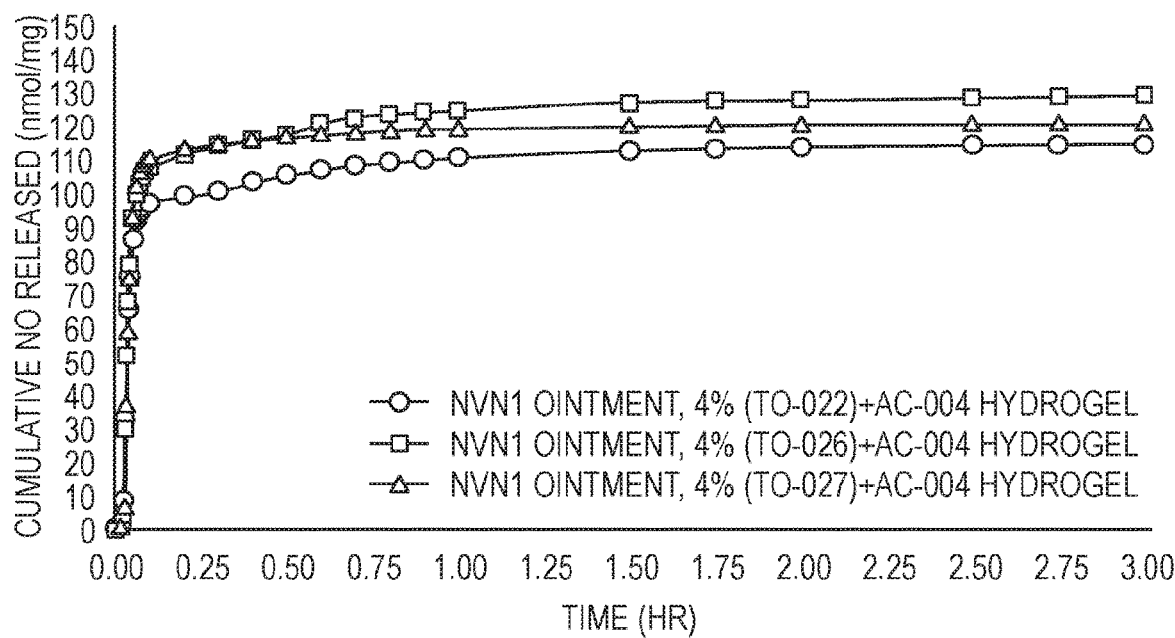
FIG. 16 shows a graph of the cumulative NO release for the three different admixtures.

Nitric oxide release was evaluated for three formulations (Table 20) upon admixture with a hydrogel (Table 14) in a 1:1 ratio. The instantaneous NO release over time for the three different admixtures is shown in FIG. 15 and the cumulative NO release for the three different admixtures is shown in FIG. 16. The Cmax, Tmax, and amount of total NO at different time points for the three different admixtures is provided in Table 21.

TABLE 20

Formulations for the NO release evaluation (i.e., TO-022, TO-026, and TO-027).

| | | % w/w | | |
| --- | --- | --- | --- | --- |
| Component | Function | TO-022 | TO-026 | TO-027 |
| Crodabase SQ | Ointment Base | 42.0 | 85.0 | 87.0 |
| Petrolatum | Ointment Base | 42.0 | — | — |
| Mineral Oil | Diluent/Solvent | 8.0 | 3.0 | — |
| Softigen 767 | Emollient/Emulsifier | 4.0 | 4.0 | 4.0 |
| Cetyl Alcohol | Thickener/Emulsifier | — | 4.0 | — |
| Mono/Di Glycerides | Thickener/Emulsifier | — | — | 5.0 |
| NVN1 | Active Ingredient | 4.0 | 4.0 | 4.0 |

TABLE 21

Cmax, Tmax, and total NO at various time points.

| Product | TO-027 Ointment, 4% + AC-004 Hydrogel | TO-026 Ointment, 4% + AC-004 Hydrogel | TO-022 Ointment, 4% + AC-004 Hydrogel |
| --- | --- | --- | --- |
| Cmax (pmoles/mg) | 1855.5 | 1574.7 | 1406.1 |
| Total NO (nmol/mg) | | | |
| 1 hr | 119.4 | 125.0 | 110.8 |
| 2 hr | 120.5 | 128.2 | 114.2 |

TABLE 21-continued

Cmax, Tmax, and total NO at various time points.

| Product | TO-027 Ointment, 4% + AC-004 Hydrogel | TO-026 Ointment, 4% + AC-004 Hydrogel | TO-022 Ointment, 4% + AC-004 Hydrogel |
|---|---|---|---|
| 4 hr | 121.4 | 130.2 | 115.1 |
| 6 hr | 121.5 | 130.3 | 115.1 |
| Tmax (min) | 2 | 2 | 2 |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of treating an inflammatory condition of the skin, mucosa, and/or eye in a subject, the method comprising topically administering to the skin, mucosa, and/or eye of said subject a nitric oxide-releasing pharmaceutical composition comprising at least one nitric oxide releasing compound comprising a diazeniumdiolate functional group in an amount effective to treat said inflammatory condition of the skin, mucosa, and/or eye,
    wherein the nitric oxide-releasing pharmaceutical composition comprises a first composition in admixture with a second composition,
    wherein the first composition is a hydrophobic composition that is in the form of an ointment and the first composition comprises the at least one nitric oxide releasing compound and a hydrophobic base,
    wherein the hydrophobic base is present in an amount of about 50% to about 95% by weight of the first composition,
    wherein the hydrophobic base a natural and/or synthetic fat, a natural and/or synthetic wax, and/or natural and/or synthetic oil,
    wherein the second composition is a hydrogel comprising a buffering agent, and
    wherein said nitric oxide-releasing pharmaceutical composition has a pH in a range from 4 to 6.5, as measured in vitro, at about 1 hour after administration.

2. The method of claim 1, wherein the nitric oxide releasing compound comprises NO-releasing co-condensed silica particles.

3. The method of claim 1, wherein the nitric oxide-releasing pharmaceutical composition comprises two or more active pharmaceutical ingredients.

4. The method of claim 1, wherein said nitric oxide-releasing pharmaceutical composition is topically administered in an amount effective to decrease inflammatory cells in the skin, mucosa, and/or eye of said subject.

5. The method of claim 1, wherein said nitric oxide-releasing pharmaceutical composition is configured and/or formulated to deliver nitric oxide to an endothelial cell in the skin, mucosa, and/or eye of said subject.

6. The method of claim 1, wherein said nitric oxide-releasing pharmaceutical composition is topically administered in an amount effective to modulate and/or inhibit at least one cytokine selected from the group consisting of TNFα, IL-1, IL-1α, IL-10, IL-2, IL-4, IL-5, IL-6, IL-8, IL-10, IL-12, IL-13, IL-17, IL-17a, IL-17f, IL-22, IL-23, IL-12/IL-23p40, KC/Gro, and any combination thereof.

7. The method of claim 1, wherein said inflammatory condition is an infection in said skin, mucosa, and/or eye of said subject.

8. The method of claim 1, wherein said nitric oxide-releasing pharmaceutical composition is topically administered in an amount effective to reduce the amount of IL-17A, IL-17F, and/or IL-1β in the subject.

9. The method of claim 1, wherein the topical administration of said nitric oxide-releasing pharmaceutical composition does not produce systemic effects from the administration of nitric oxide.

10. The method of claim 1, wherein the at least one nitric oxide releasing compound comprising the diazeniumdiolate functional group is present in the first composition in an amount of about 0.1% to about 30% by weight of the first composition.

11. The method of claim 1, wherein said nitric oxide-releasing pharmaceutical composition has a pH of less than about 7, as measured in vitro.

12. The method of claim 1, wherein said nitric oxide-releasing pharmaceutical composition has a pH in a range from 4 to 6.5, as measured in vitro, at about 24 hours after administration.

13. The method of claim 1, wherein the pH at about 1 hour after administration and at about 24 hours after administration varies by less than ±0.2.

14. The method of claim 1, wherein said nitric oxide-releasing pharmaceutical composition is administered in an amount sufficient to provide at least a 2-log reduction in bacterial counts at about 1, 2, 3, 4, 5, 6, 7, 8, 9, or 10 days after administration of the composition.

15. The method of claim 1, wherein said nitric oxide-releasing pharmaceutical composition is administered once daily.

16. The method of claim 1, wherein said nitric oxide-releasing pharmaceutical composition is administered twice daily.

17. The method of claim 1, wherein the nitric oxide-releasing pharmaceutical composition releases at least about 100 nmol of NO/mg of the composition at 1 hour after administration, as measured by in vitro release.

18. The method of claim 1, wherein the nitric oxide-releasing pharmaceutical composition has a maximum concentration (Cmax) of NO release of at least about 1200 pmol of NO/mg of the composition at about 1 to about 20 minutes after administration, as measured by in vitro release.

* * * * *

UNITED STATES PATENT AND TRADEMARK OFFICE
CERTIFICATE OF CORRECTION

PATENT NO. : 10,912,743 B2
APPLICATION NO. : 16/081708
DATED : February 9, 2021
INVENTOR(S) : Stasko et al.

Page 1 of 1

It is certified that error appears in the above-identified patent and that said Letters Patent is hereby corrected as shown below:

In the Specification

Column 10, Lines 19-20: Please correct ".$NO_2$ and/or .OH" to read -- ·$NO_2$ and/or ·OH --

Column 11, Line 10: Please correct ".$NO_2$ and .OH" to read -- ·$NO_2$ and ·OH --

Column 11, Line 11: Please correct ".$NO_2$ and .OH" to read -- ·$NO_2$ and ·OH --

In the Claims

Column 58, Line 7, Claim 6: Please correct "IL-10, IL-2" to read -- IL-1β, IL-2 --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*